(12) United States Patent
Mack et al.

(10) Patent No.: US 8,043,075 B2
(45) Date of Patent: Oct. 25, 2011

(54) PROGRESSIVE CAVITY PROPAGATION PUMP

(75) Inventors: Stanley Paul Mack, Suwanee, GA (US);
Joseph Amley, Suwanee, GA (US);
Steven LaCross, Norcross, GA (US);
Danny Lincoln, Commerce, GA (US);
Charles R. Patzer, Columbus, OH (US);
Stephen L. Vick, Norcross, GA (US)

(73) Assignee: Smiths Medical ASD, Inc., Rockland, MA (US)

( * ) Notice: Subject to any disclaimer, the term of this patent is extended or adjusted under 35 U.S.C. 154(b) by 1160 days.

(21) Appl. No.: 11/765,121

(22) Filed: Jun. 19, 2007

(65) Prior Publication Data

US 2008/0317605 A1    Dec. 25, 2008

(51) Int. Cl.
*F04B 43/08* (2006.01)
*F01C 1/02* (2006.01)

(52) U.S. Cl. ............ 417/476; 417/479; 418/54; 418/56; 418/58

(58) Field of Classification Search .................. 417/476, 417/479; 418/56, 66, 54, 58
See application file for complete search history.

(56) References Cited

U.S. PATENT DOCUMENTS

| | | | |
|---|---|---|---|
| 2,311,851 A | 2/1943 | McClure | |
| 2,902,935 A * | 9/1959 | Dean et al. | 418/149 |
| 3,073,332 A | 1/1963 | Strader | |
| 3,161,141 A * | 12/1964 | Henry | 418/56 |
| 3,227,158 A * | 1/1966 | Mattingly | 601/162 |
| 3,782,865 A * | 1/1974 | Braun | 418/56 |
| 3,922,119 A | 11/1975 | Rosenquist | |
| 4,084,606 A | 4/1978 | Mittleman | |
| 4,596,558 A | 6/1986 | Smith et al. | |
| 4,666,429 A | 5/1987 | Stone | |
| 4,819,684 A | 4/1989 | Zaugg et al. | |
| 5,147,333 A | 9/1992 | Raines | |
| 5,176,658 A | 1/1993 | Ranford | |
| 5,573,515 A | 11/1996 | Wilson et al. | |
| 5,593,290 A | 1/1997 | Greisch et al. | |
| 5,800,397 A | 9/1998 | Wilson et al. | |
| 5,882,343 A | 3/1999 | Wilson et al. | |
| 5,961,298 A * | 10/1999 | Bar-Cohen et al. | 417/322 |
| 6,059,747 A | 5/2000 | Bruggeman et al. | |
| 6,074,179 A | 6/2000 | Jokela et al. | |
| 6,095,776 A * | 8/2000 | Maki | 418/45 |
| 6,099,511 A | 8/2000 | Devos et al. | |

(Continued)

FOREIGN PATENT DOCUMENTS

DE     68411204.2     8/1988

(Continued)

*Primary Examiner* — Charles Freay
(74) *Attorney, Agent, or Firm* — Wood, Herron & Evans, LLP

(57) ABSTRACT

A pump is provided that includes a body made at least partially of an elastomeric material and an inlet port and an outlet port, with each port being coupled to the body. The pump further includes a flow passage formed in the body and extending between the inlet port and the outlet port, with at least a portion of the flow passage being normally closed and with the inlet port being fluidicly uncoupled with the outlet port when the pump is in a free-state condition. An actuating device is coupled to the body and is operable for sequentially deforming the body to create a cavity within the normally closed portion of the flow passage, the cavity being in fluid communication with the inlet port, thereby drawing a packet of fluid from the inlet port into the cavity and propagating the cavity and the packet of fluid contained therein toward the outlet port.

71 Claims, 31 Drawing Sheets

U.S. PATENT DOCUMENTS

| | | |
|---|---|---|
| 6,221,045 B1 | 4/2001 | Duchon et al. |
| 6,293,926 B1 * | 9/2001 | Sorensen et al. ............... 604/153 |
| 6,344,030 B1 | 2/2002 | Duchon et al. |
| 6,609,901 B2 * | 8/2003 | Bussmann .................... 417/572 |
| 6,626,862 B1 | 9/2003 | Duchon et al. |
| 6,656,157 B1 | 12/2003 | Duchon et al. |
| 6,866,654 B2 | 3/2005 | Callan et al. |
| 2002/0057972 A1 * | 5/2002 | Baringa et al. ........... 417/413.3 |
| 2002/0183616 A1 | 12/2002 | Toews et al. |
| 2003/0181866 A1 | 9/2003 | Abrahamson et al. |
| 2004/0143212 A1 | 7/2004 | Trombley et al. |
| 2005/0096627 A1 | 5/2005 | Howard |

FOREIGN PATENT DOCUMENTS

| | | |
|---|---|---|
| DE | 29805173 U1 | 8/1998 |
| DE | 19856744 A1 | 6/2000 |
| FR | 1498254 | 10/1967 |
| FR | 2444177 | 7/1980 |
| FR | 2451477 | 10/1980 |
| WO | 0136026 | 5/2001 |
| WO | 0158506 | 8/2001 |
| WO | 02/23043 A1 | 3/2002 |
| WO | 2005/111423 A1 | 11/2005 |
| WO | 2006/056986 A1 | 6/2006 |

* cited by examiner

PROGRESSIVE CAVITY PROPAGATION PUMP

FIELD

The present invention relates generally to pumps, and more particularly to progressive cavity propagation pumps.

BACKGROUND

Peristaltic pumps are known and have been utilized in systems for dispensing medical fluid intravenously to a patient. Peristaltic pumps include a normally open fluid flow path, typically defined by a hollow section of tubing, and a plurality of spaced apart "fingers" that sequentially deform the tubing. The sequential deformation of the tubing pressurizes the fluid within the flow cavity and propagates the fluid in a wave-like motion between the inlet and outlet ports of the pump.

While peristaltic pumps have been utilized in the medical art, they are subject to various disadvantages. For example, since the fluid flow cavity is normally open, fluid can be inadvertently supplied to the patient. This can occur if the tubing leading from a source of fluid, such as an IV bag, to the inlet port of the pump is not clamped. Also, the continuous compression of the tubing defining the normally open flow path, can result in tube fatigue, thereby necessitating replacement of the tube that adds to the operational cost of the system.

Peristaltic pumps are affected by the hydraulic head height, resulting from the position of the source of fluid above the pump, which can result in further inaccuracies with the flow rate from the pump. Additionally, peristaltic pumps are typically complex in nature, due to the number of parts required, which is directly related to the cost of the pump.

It is therefore desirable to provide a pump for dispensing medical fluid intravenously to a patient, which overcomes the disadvantages associated with peristaltic pumps.

SUMMARY

In view of the foregoing, a progressive cavity propagation pump is provided comprising a body made at least partially of an elastomeric material, an inlet port and an outlet port, each port being coupled to the body, and a flow passage formed in the body and extending between the inlet port and the outlet port. At least a portion of the flow passage is normally closed. The inlet port is fluidicly uncoupled with the outlet port when the pump is in a free-state condition. The pump further includes an actuating device coupled to the body, the actuating device operable for sequentially deforming the body to create a cavity within the normally closed portion of the flow passage, the cavity being in fluid communication with the inlet port, thereby drawing a packet of fluid from the inlet port into the cavity, and propagating the cavity and the packet of fluid contained therein toward the outlet port.

The flow passage can be normally closed and extend from the inlet port to the outlet port. The normally closed flow passage can extend along a substantially linear path between the inlet port and the outlet port and can be disposed laterally between first and second longitudinally extending elastomeric portions of the body, with the first and second portions of the body being disposed in abutting relationship with one another when the flow passage is closed and being locally separable from one another during operation of the pump to create the cavity and propagate the cavity and the fluid therein to the outlet port.

The first portion of the body can include a flange adapted to be mounted to a stationary structure to resist movement of the first portion of the body. The second portion of the body can include a plurality of longitudinally spaced tabs. The actuating device can include a plurality of linear actuators, with each of the linear actuators being coupled to one of the tabs. The linear actuators can be programmed to push and pull on the tabs to propagate the cavity and the packet of fluid therein to the outlet port. Each of the linear actuators can include a stepper motor, a block made of an electro-active polymer or a cam. The actuating device can further include a plurality of actuating members, each coupled at one end to the body and coupled at the other end to one of the linear actuators.

In another embodiment, the body of the pump can include a frame made of a thermoplastic material and an elastomeric member overmolded onto the frame. The normally closed flow passage can be disposed laterally between the frame and the elastomeric member. The actuating device can be coupled to the frame and the elastomeric member and can be operably effective for sequentially pulling the elastomeric member away from the frame at a plurality of longitudinally spaced locations, wherein the cavity is created and the cavity and the packet of fluid therein are propagated to the outlet port.

The flow passage can be normally closed and can extend along a circular path between the inlet port and the outlet port. The body can be adapted to be mounted to a stationary structure and can include a centrally disposed aperture formed therein. The actuating device can include a driven axle disposed within the aperture and the driven axle can orbit in a circular motion that is offset relative to the aperture during operation of the pump wherein the cavity is created and propagated, with the fluid contained therein, to the outlet port.

The driven axle can include a first longitudinal centerline axis and the actuating device can further include a motor having an output shaft that is rotatable about a second longitudinal centerline axis. The output shaft can be coupled to the driven axle and the second longitudinal centerline axis can be offset relative to the first longitudinal centerline axis, wherein the driven axle orbits around the second longitudinal centerline axis during operation of the pump thereby creating the cavity and propagating the cavity and the packet of fluid therein to the outlet port.

In another embodiment, the flow passage can comprise a first normally closed flow passage and the pump further comprises a second normally closed flow passage. The pump can further include first and second open conduits, each disposed within the body and each having proximal and distal ends. A proximal end of the first flow passage can be disposed proximate the inlet port, with a distal end disposed proximate the proximal end of the first open conduit. The distal end of the first open conduit can be disposed proximate the outlet port.

A proximal end of the second open conduit can be disposed proximate the inlet port, with the distal end being disposed proximate the proximal end of the second normally closed flow passage. The distal end of the second normally closed flow passage can be disposed proximate the outlet port.

In this embodiment, the body can be adapted to be mounted to a stationary structure and can include a centrally disposed aperture formed therein. The actuating device can include a driven axle disposed within the aperture. During operation of the pump, the driven axle orbits in a circular motion that is offset relative to the aperture, wherein during a first portion of any revolution of the driven axle, the cavity, which comprises a first cavity, is created and propagated, with the packet of fluid contained therein, to the outlet port. During a second portion of any revolution of the driven axle a second cavity is created within the second normally closed flow passage, drawing a second packet of fluid into the second cavity, and the second cavity and second packet of fluid are propagated to the outlet port. In this embodiment, the first and second flow passages extend along arcuate paths.

In another embodiment, the body can include an outer frame made of a first thermoplastic material and an elastomeric member, with the elastomeric member being overmolded onto the outer frame. The body can further include an inner frame made of a second thermoplastic material, with the inner frame engaging the elastomeric member. The flow passage is normally closed, is disposed between the elastomeric member and the outer frame and extends along an arcuate path between the inlet and outlet ports. The arcuate path can be a circular path. The elastomeric member can include an inner hub defining a centrally disposed aperture extending through the elastomeric member.

In this embodiment, the elastomeric member can include a rim and a plurality of circumferentially spaced spokes that extend between the hub and the rim. The hub, spokes and rim define a plurality of circumferentially spaced cavities having a first shape. The inner frame can include a plurality of circumferentially spaced engaging members having a second shape that is complimentary with the first shape of the cavities. Each of the engaging members is disposed in one of the cavities. The engaging members of the inner frame can define a discontinuous cylindrical surface having a first diameter and the rim can include a discontinuous inner surface having a second diameter, with the first diameter being greater than the second diameter.

In this embodiment, the normally closed flow passage is disposed between the elastomeric member and the outer frame and extends along an arcuate path between the inlet and outlet ports. The inner frame includes a centrally disposed aperture formed therein and the actuating device can include a driven axle disposed within the aperture. The driven axle orbits in a circular motion that is offset relative to the aperture of the inner frame and the driven axle is in contacting engagement with the inner frame during operation of the pump, wherein the elastomeric member is pulled away from the outer frame at a position proximate the inlet port, creating the cavity and drawing the packet of fluid from the inlet port into the cavity, and wherein the cavity and the packet of fluid contained therein are propagated along a circular path to the outlet port.

In another embodiment, the body comprises an outer frame made of a first thermoplastic material and an inner frame made of a second thermoplastic material, with the outer frame being disposed in surrounding relationship with the inner frame. The body can further comprise an elastomeric member overmolded onto the outer frame and the inner frame. The flow passage is normally closed, is disposed between the elastomeric member and the outer frame and extends along an arcuate path between the inlet and outlet ports. The inner frame can include a centrally disposed aperture formed therein and the actuating device can include a driven axle disposed within the aperture of the inner frame. During operation of the pump, the driven axle orbits in a circular motion that is offset relative to the aperture of the frame, with the driven axle being in contacting engagement with the inner frame, wherein the elastomeric member is pulled away from the outer frame at a position proximate the inlet port creating the cavity and drawing the packet of fluid from the inlet port into the cavity, and wherein the cavity and the packet of fluid contained therein are propagated along a circular path to the outlet port.

In another embodiment, the body of the pump includes a first sub-assembly having an inner-frame made of a thermoplastic material and a first elastomeric member overmolded onto the inner frame. The body further includes a second sub-assembly including an outer frame having a centrally disposed aperture formed therein and extending therethrough. The second sub-assembly further includes the first sub-assembly, wherein the first sub-assembly is disposed within the aperture formed in the outer frame and is in contact engagement with the outer frame. The flow passage is normally closed and extends between the first elastomeric member and the outer frame along an arcuate path between the inlet port and the outlet port.

The body further includes a second elastomeric member overmolded onto the second sub-assembly. The second elastomeric member prevents fluid from leaking from the normally closed flow passage exterior of the body of the pump. The outer frame can include a plurality of relatively smaller apertures disposed outward of the centrally disposed aperture and the second elastomeric member can extend into the plurality of relatively smaller apertures.

In this embodiment, the inner frame can include a centrally disposed aperture extending therethrough, and the actuating device can include a driven axle disposed within the aperture of the inner frame. The driven axle can orbit in a circular motion that is offset relative to the aperture of the inner frame, with the driven axle in contacting engagement with the inner frame during operation of the pump, wherein the first elastomeric member is pulled away from the outer frame at a position proximate the inlet port creating the cavity and drawing the packet of fluid from the inlet port into the cavity, and wherein the cavity and the packet of fluid contained therein are propagated along a circular path to the outlet port.

In another embodiment, the body comprises an outer frame made of a first thermoplastic material, with the outer frame having a channel formed therein, and with the inlet port and outlet port being in fluid communication with the channel. The channel extends in a circular path between the inlet and outlet ports. The body further includes an inner frame made of a second thermoplastic material, with the inner frame including a base member, a tower integral with the base member and extending longitudinally away from the base member and a protruding portion integral with and extending away from the base member. The protruding portion is disposed within the channel of the frame. The body further includes an elastomeric member overmolded onto the inner and outer frames, wherein the elastomeric member is disposed between the protruding portion of the inner frame and the channel of the outer frame. The flow passage normally closed, is disposed between the elastomeric member and the channel of the outer frame and extends in a circular path between the inlet and outlet ports.

In this embodiment, the tower is hollow and includes an inner surface. The actuating device includes a driven axle extending into the tower and engaging the inner surface of the tower. The engagement of the driven axle with the inner surface of the tower during operation of the pump causes the protruding portion to wobble within the channel of the outer frame and causes the elastomeric member disposed between the protruding portion and the channel to pull away from the channel, wherein the cavity is created and the cavity and the packet of fluid contained therein are propagated to the outlet port.

According to a second aspect of the present invention, a method of pumping a fluid is provided comprising providing a flow passage in a pump body with at least a portion of the flow passage being normally closed. The method further comprises coupling fluid inlet and outlet ports to the pump body, and sequentially deforming the pump body to create a cavity within the normally closed portion of the flow passage to draw fluid from the inlet port into the cavity and to propagate the cavity and the fluid contained therein toward the outlet port.

The method can further comprise separating a first elastomeric portion of the body from a second elastomeric portion of the body to create the cavity and to propagate the cavity and the fluid contained therein toward the outlet port.

Alternatively, the method can further comprise sequentially separating an elastomeric portion of the body from a thermoplastic portion of the body to create the cavity and the propagate the cavity and the fluid contained therein toward the outlet port.

The flow passage is normally closed and can extend along a substantially linear path and the method can further comprise propagating the cavity and the fluid contained therein through the normally closed flow passage along the substantially linear path from the inlet port to the outlet port. Alternatively, the flow passage is normally closed and can extend along an arcuate path and the method can further comprise propagating the cavity and the fluid contained therein through the normally closed flow passage along the arcuate path from the inlet port to the outlet port.

The method can further comprise fluidicly coupling a source of fluid to the inlet port, fluidicly coupling the outlet port to a tubing system coupled to the patient and pumping the fluid to the patient.

DRAWINGS

These and other features, aspects and advantages of the present invention will become better understood with regard to the following description, appended claims and accompanying drawings wherein:

Figure 4A:
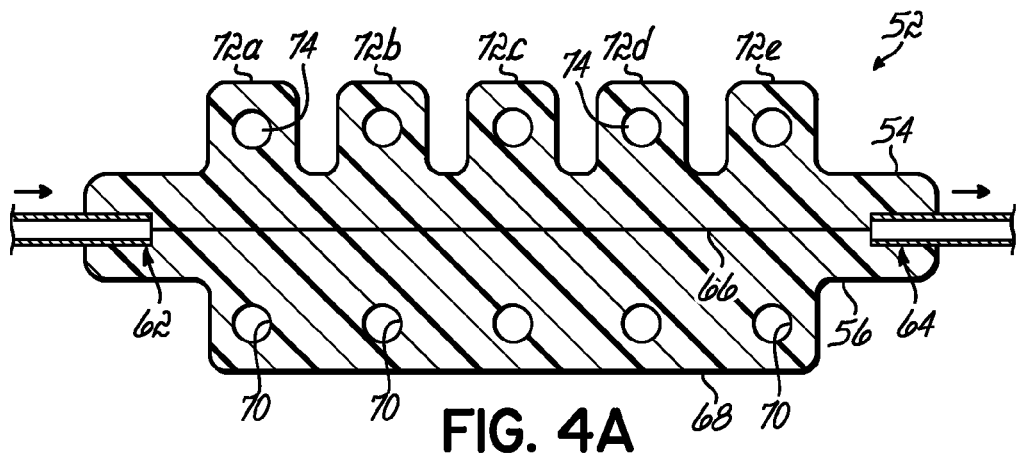
FIG. 4A is a cross-sectional view of the pump shown in FIGS. 2 and 3 taking along line 4A-4A in FIG. 3, with the included flow passage of the pump shown in a closed position.
Figure 4B:
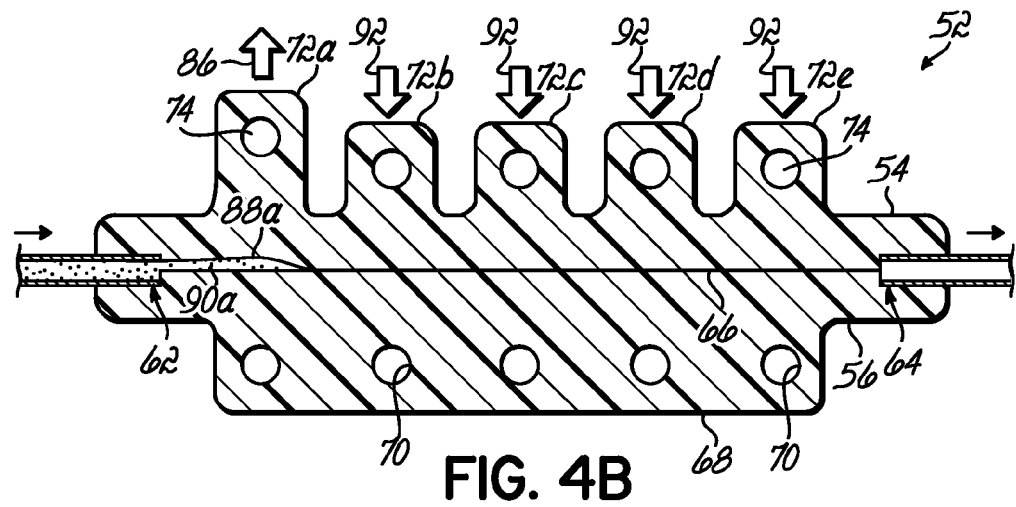
FIG. 4B is a cross-sectional view similar to FIG. 4A, but with the pump body deformed to create a cavity in the flow passage at a location proximate the inlet port, with fluid drawn into the cavity, as a result of forces exerted by the actuating device on the pump body.
Figure 4C:
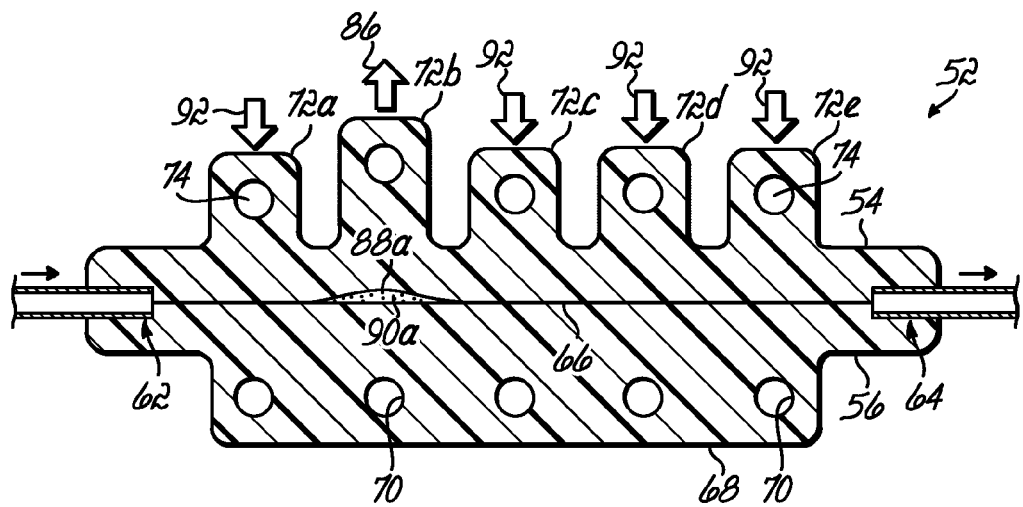
FIG. 4C is a cross-sectional view similar to FIGS. 4A and 4B, but with the cavity and the fluid therein shown in FIG. 4B propagated toward the outlet port as a result of forces exerted by the actuating device on the pump body.
Figure 4D:
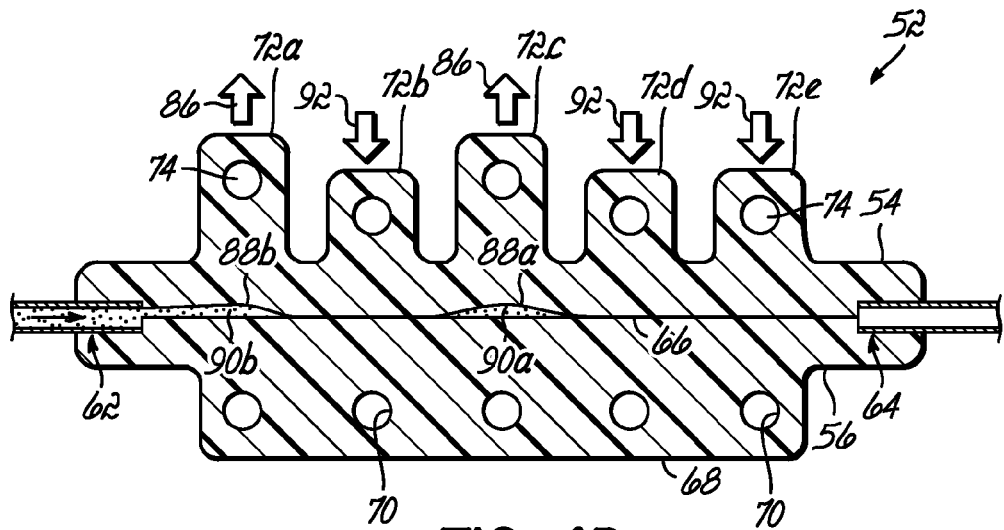
FIG. 4D is a cross-sectional view similar to FIGS. 4A-4C, but with the cavity and the fluid therein shown in FIGS. 4B and 4C propagated farther toward the outlet port and a second cavity created proximate the inlet port, with fluid drawn into the cavity, as a result of forces exerted by the actuating device on the pump body.
Figure 4E:
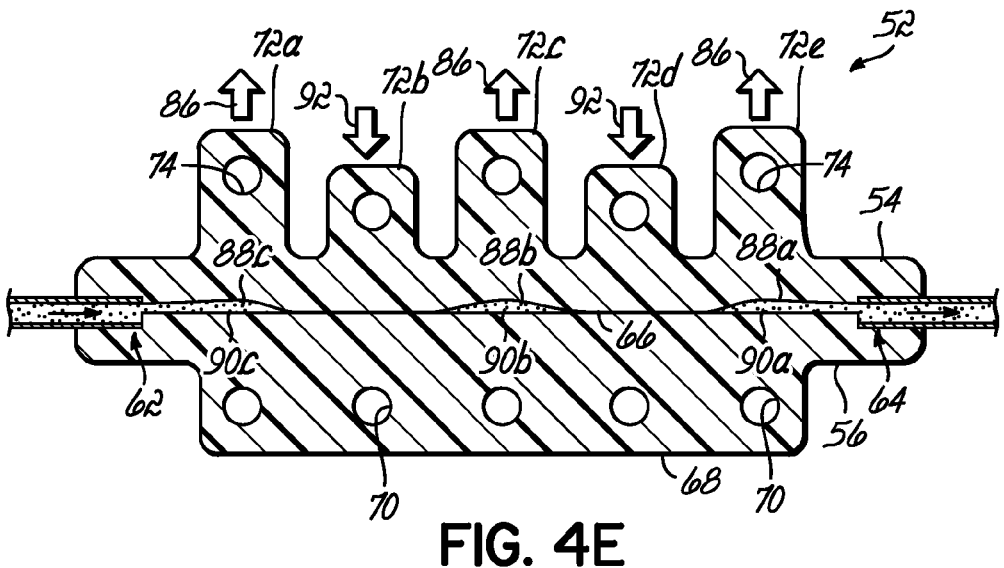
Figure 5:
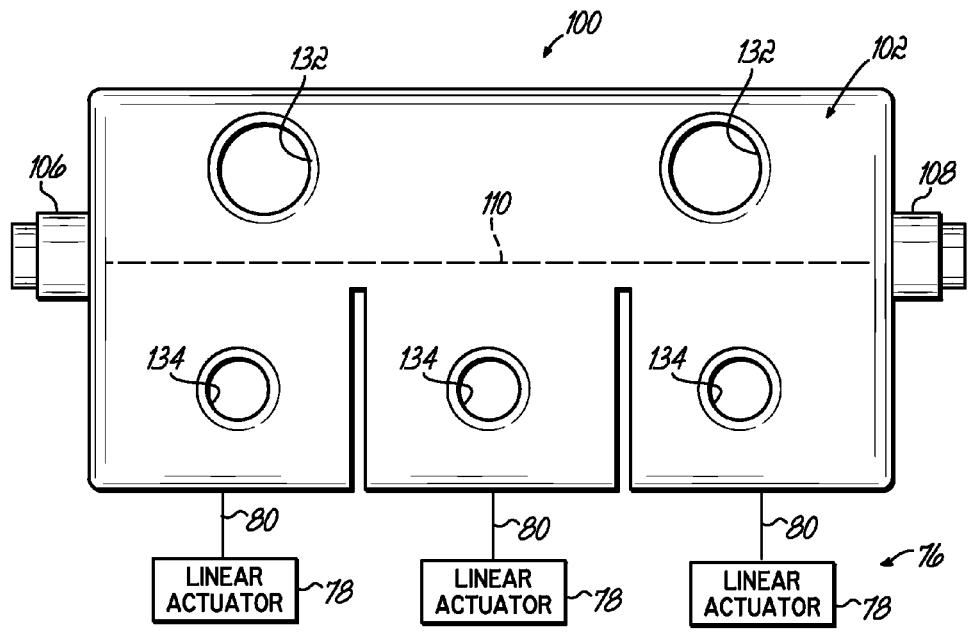
Figure 6:
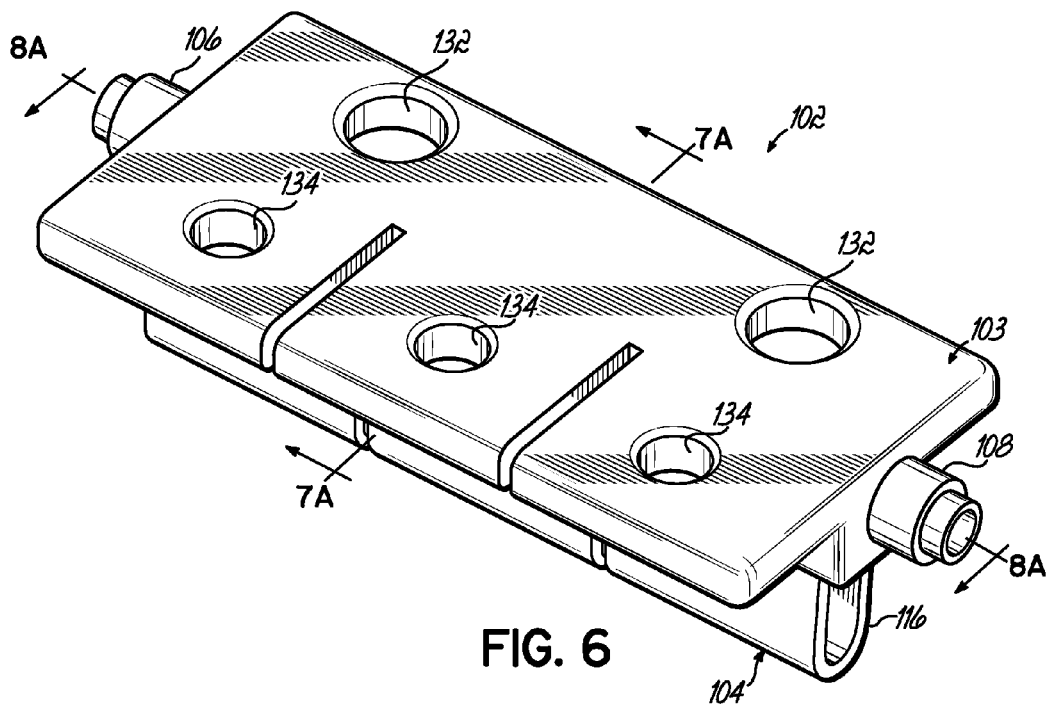
Figure 7A:
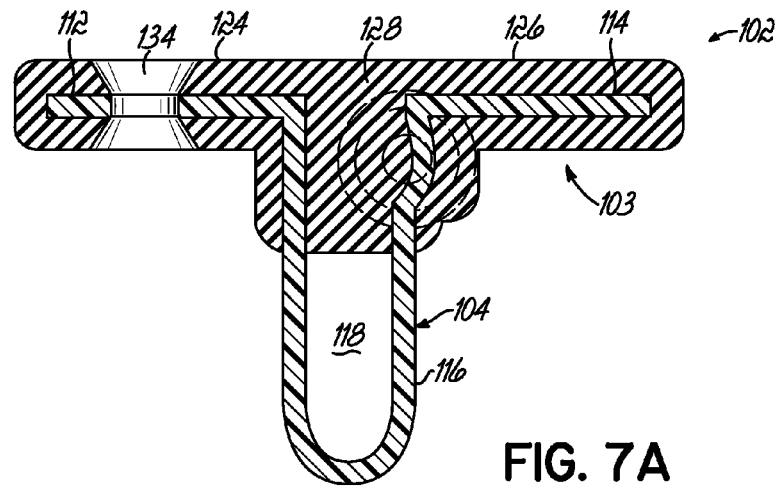
Figure 7B:
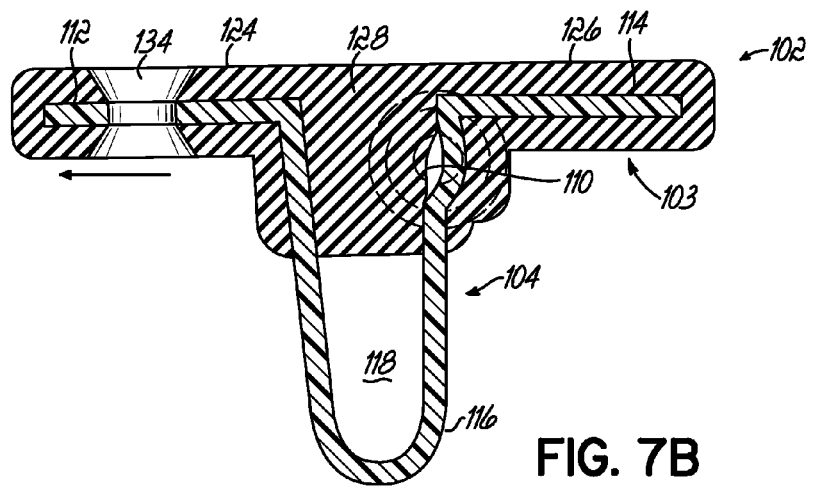
Figure 8A:
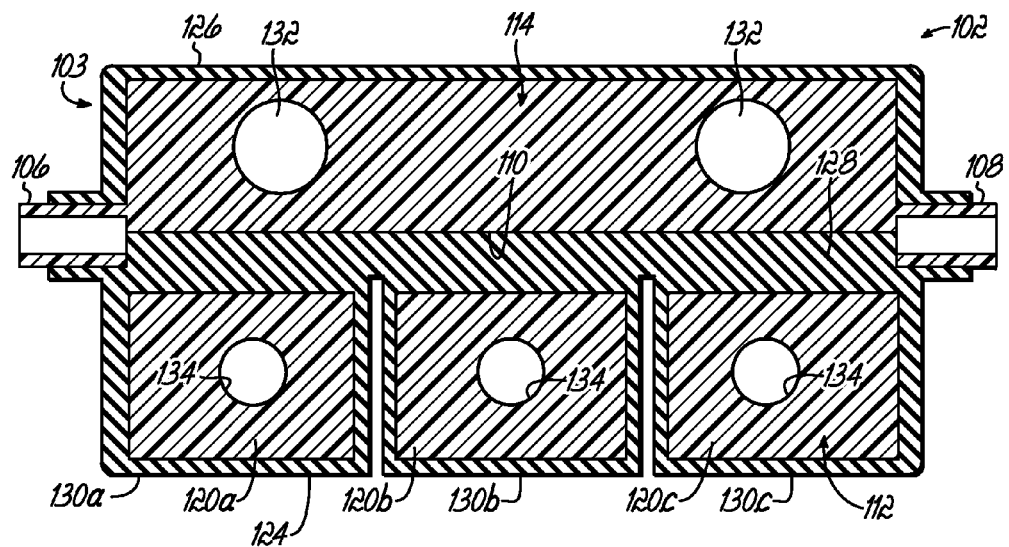
Figure 8B:
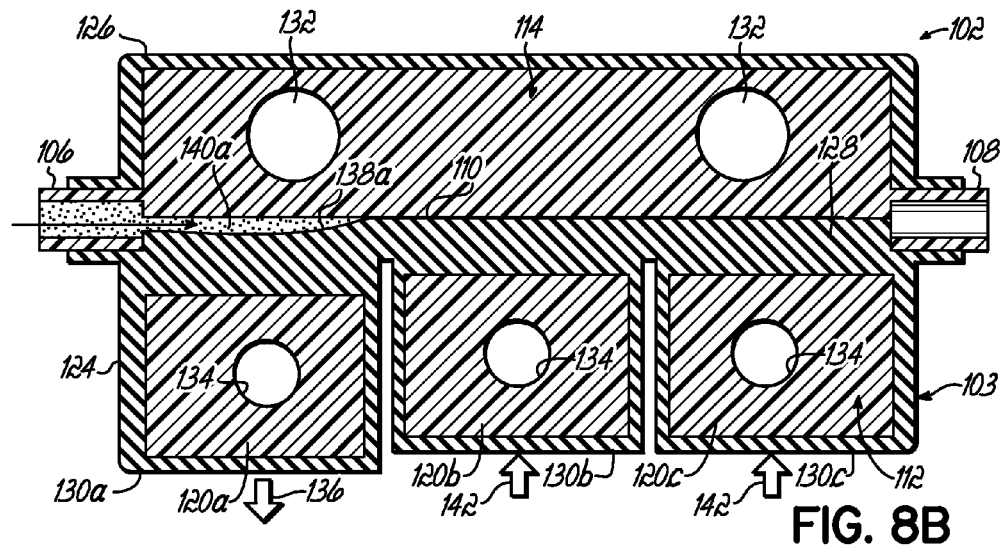
Figure 8C:
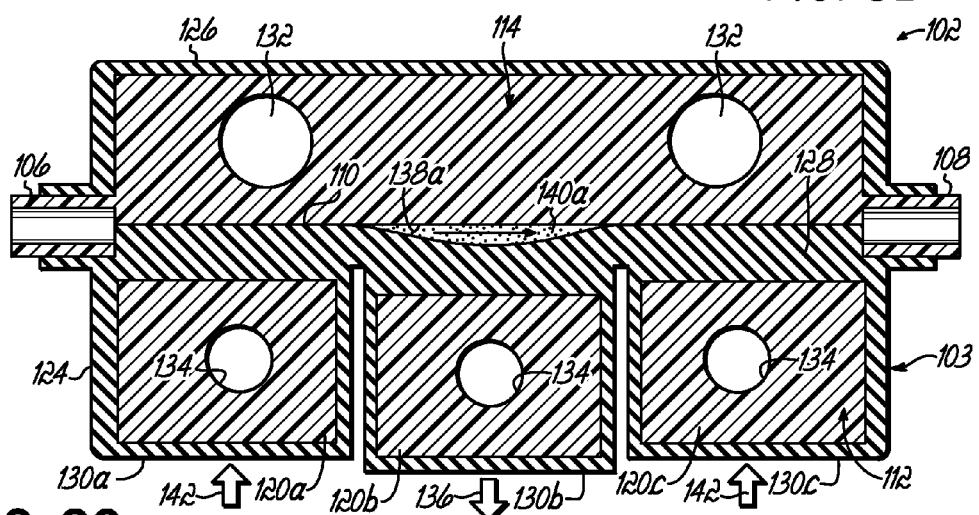
Figure 8D:
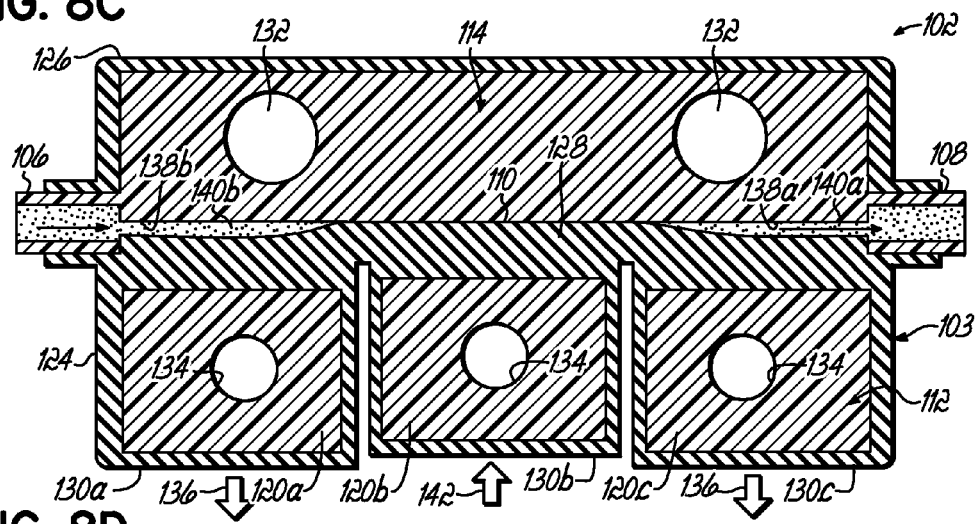
Figure 9:
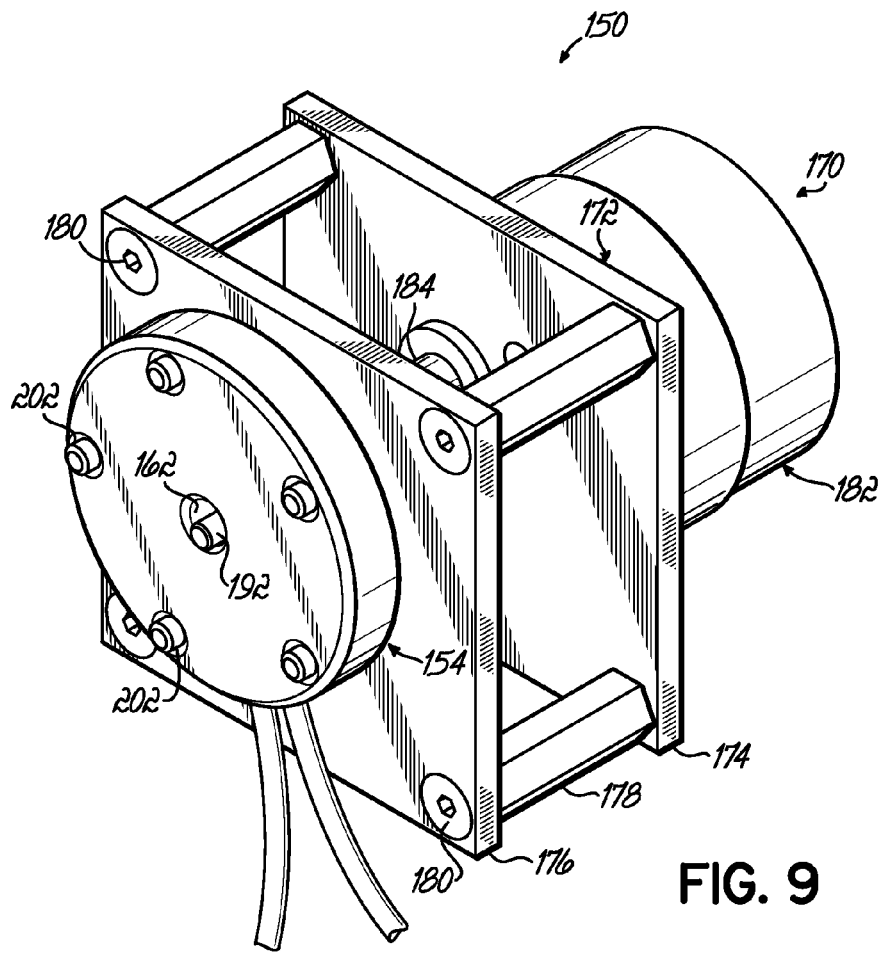
Figure 10:
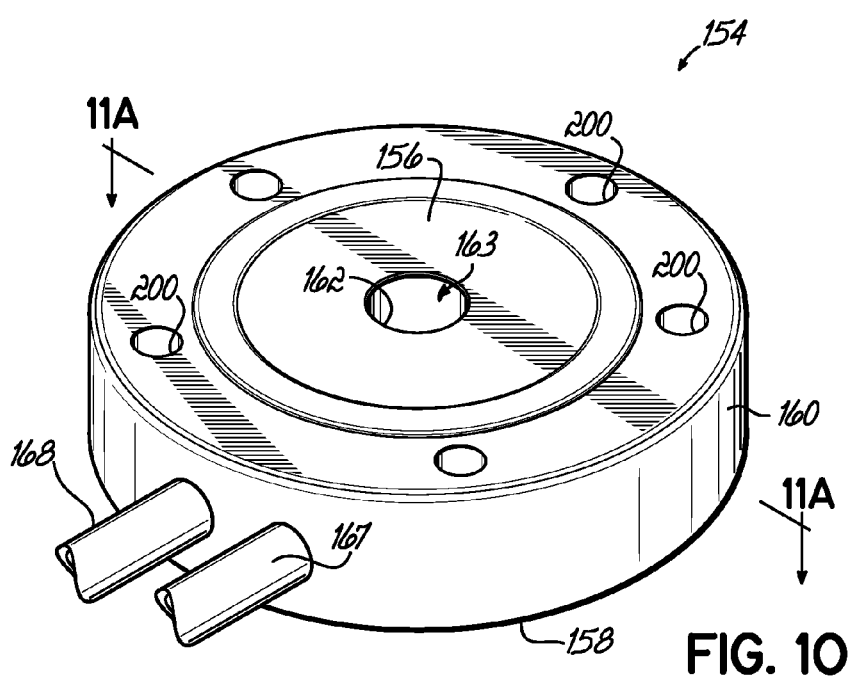
Figure 11A:
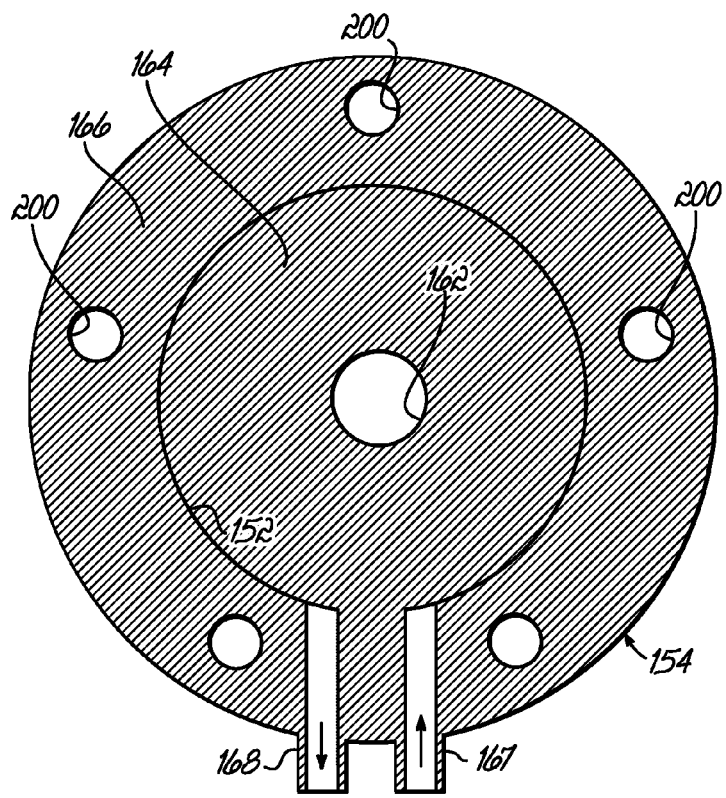
Figure 11B:
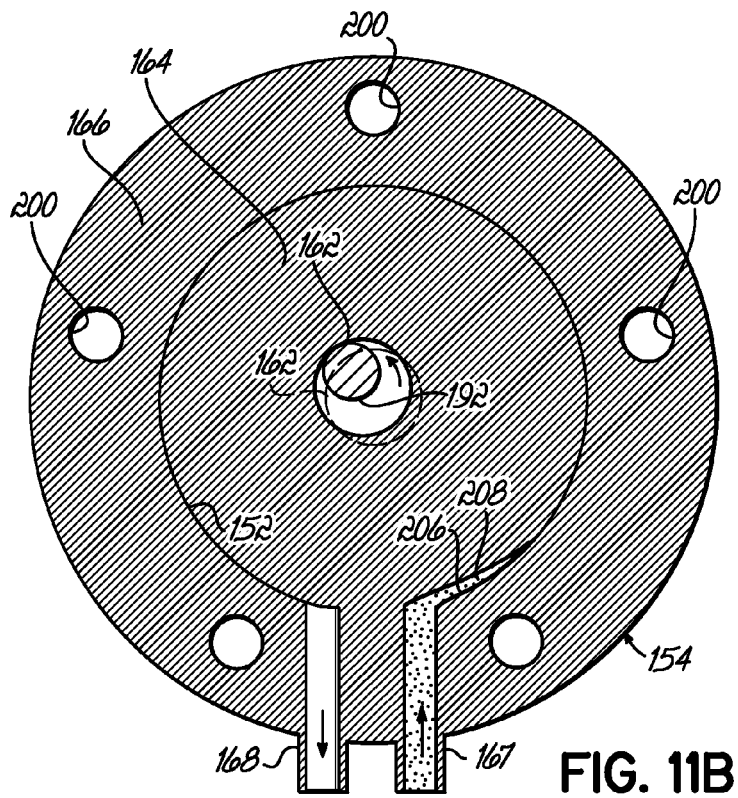
Figure 11C:
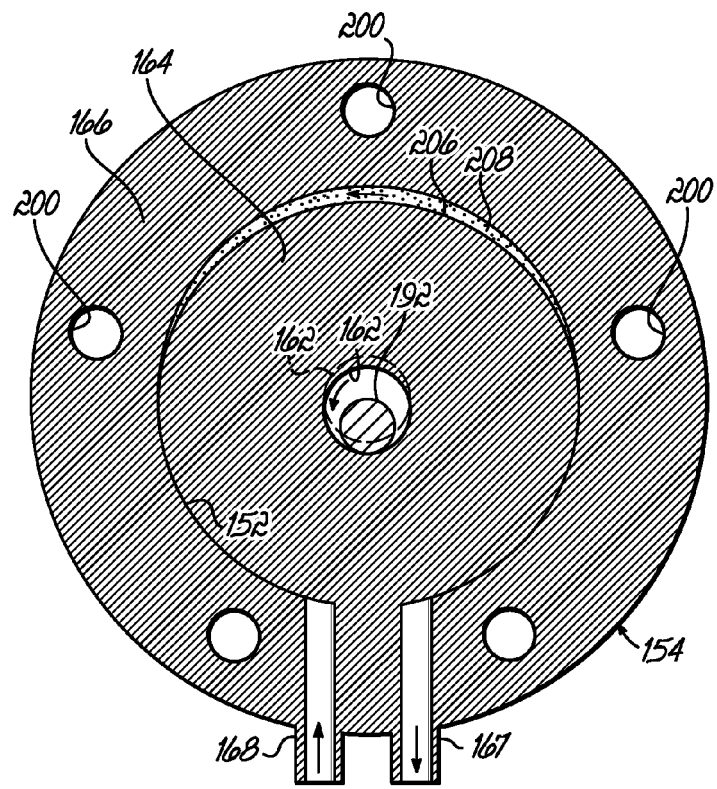
Figure 11D:
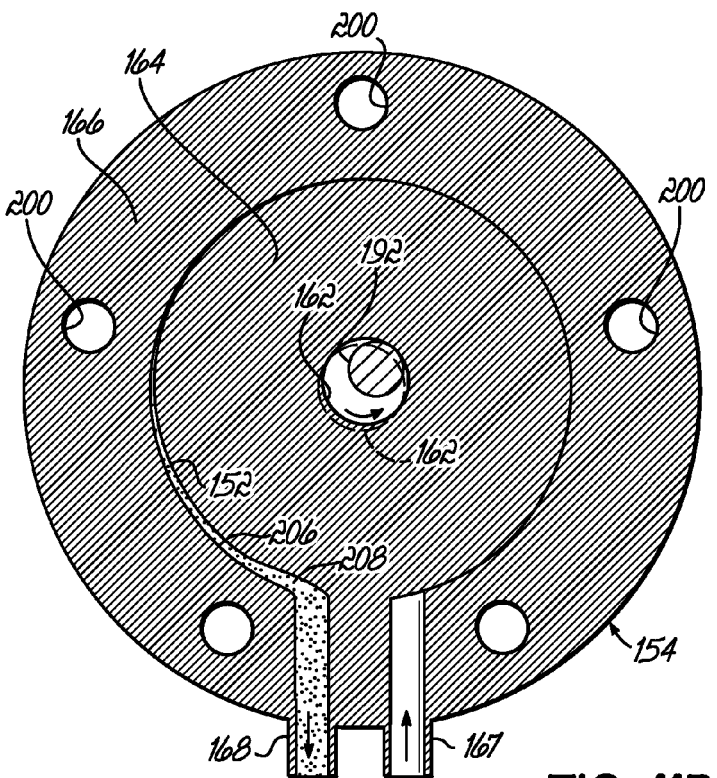
Figure 12:
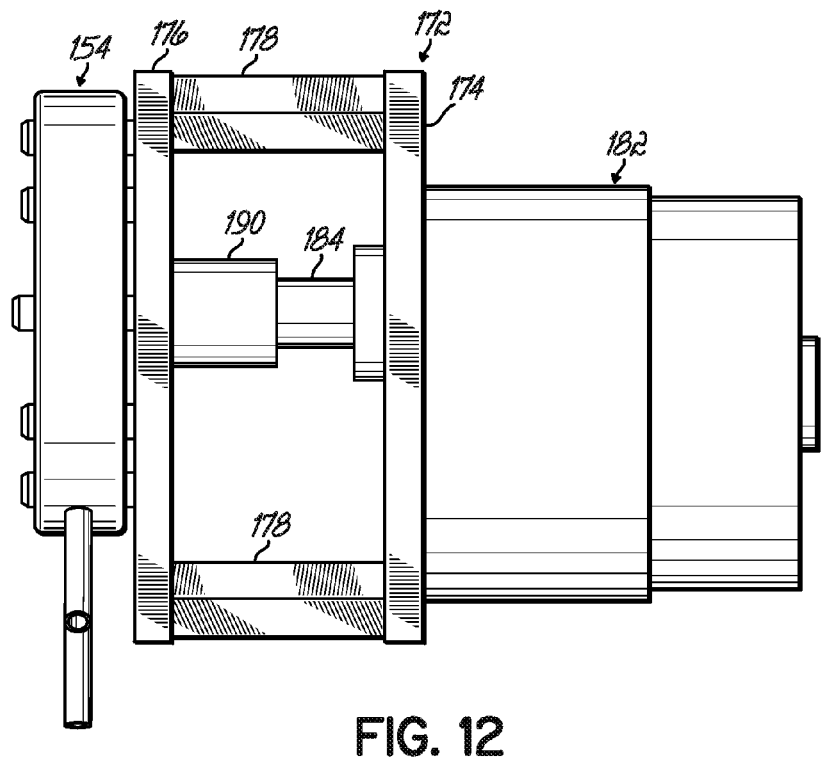
Figure 13:
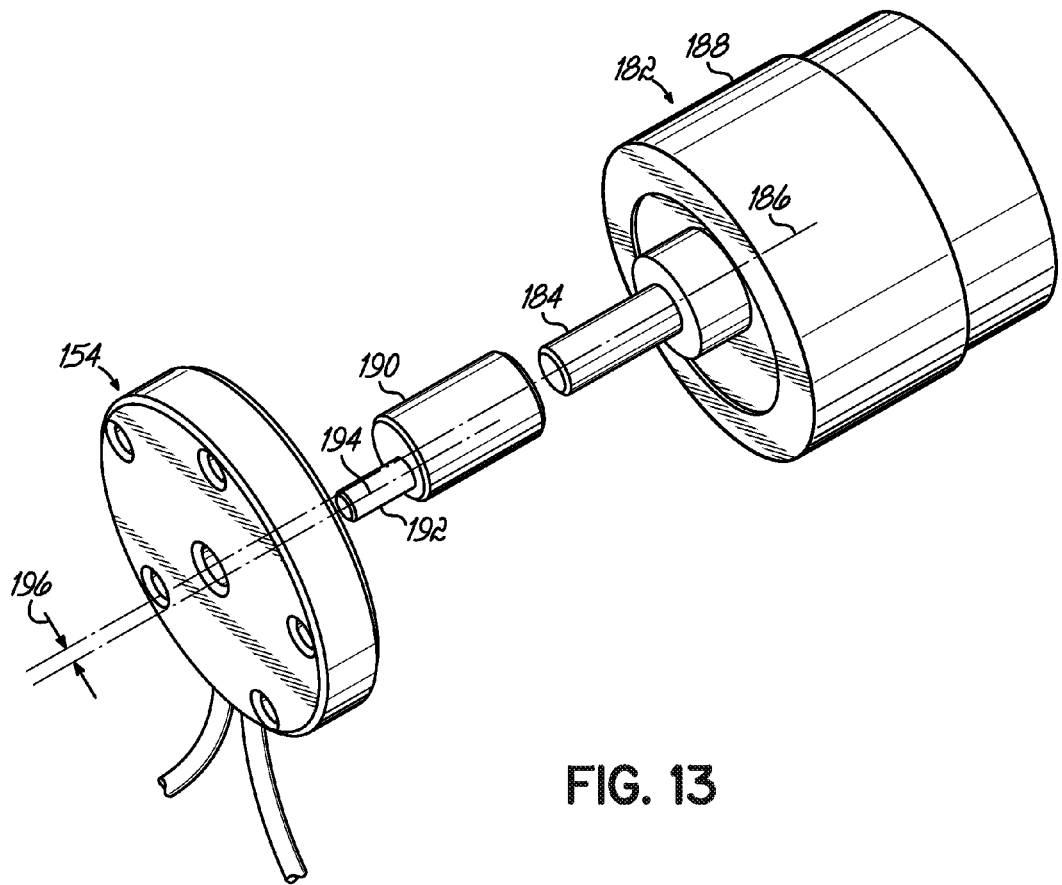
Figure 14:
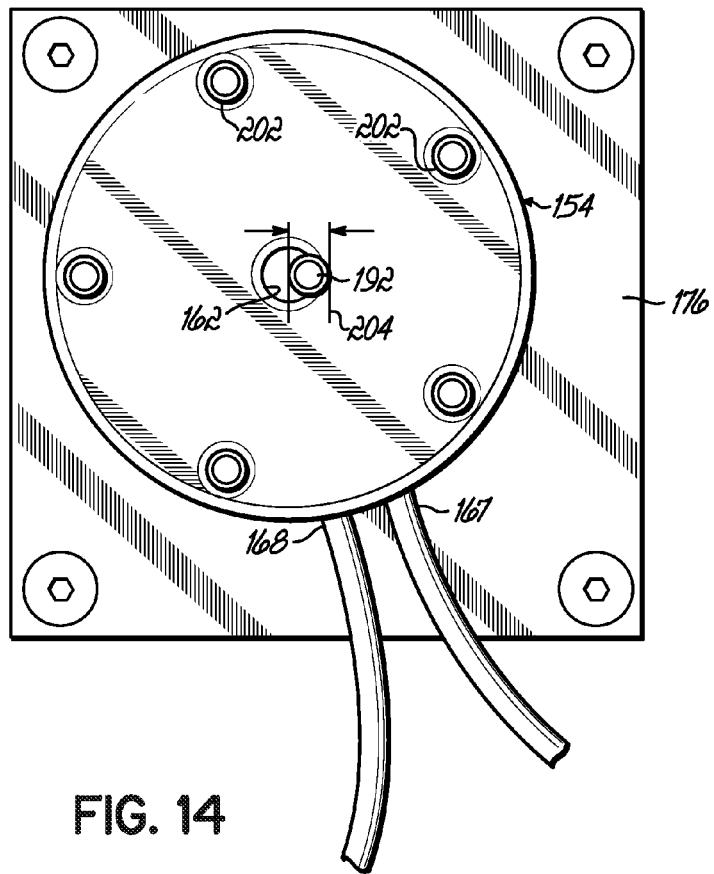
Figure 15:
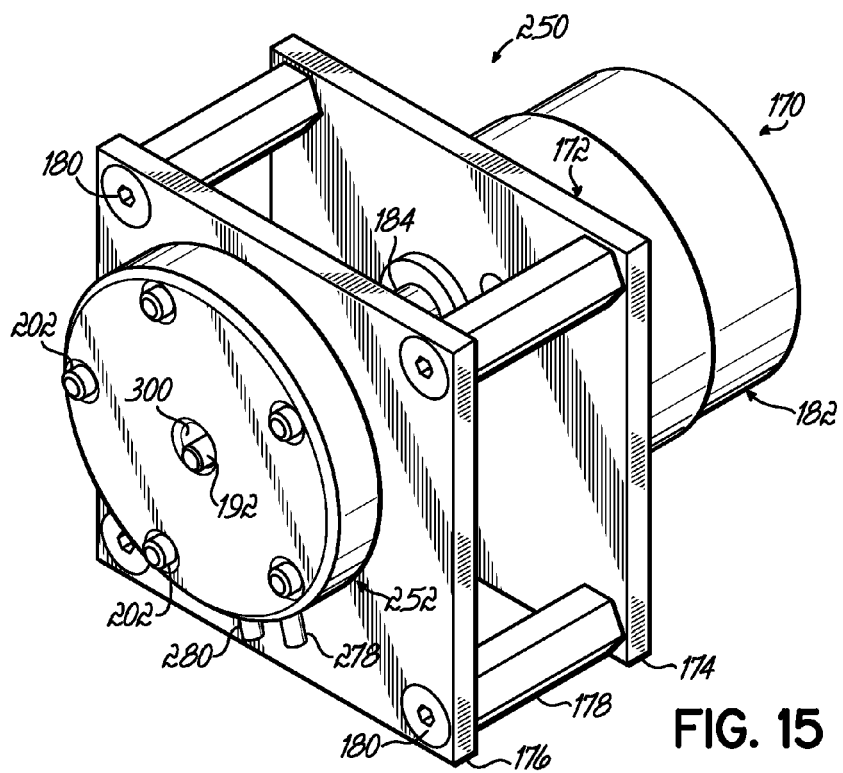
Figure 16:
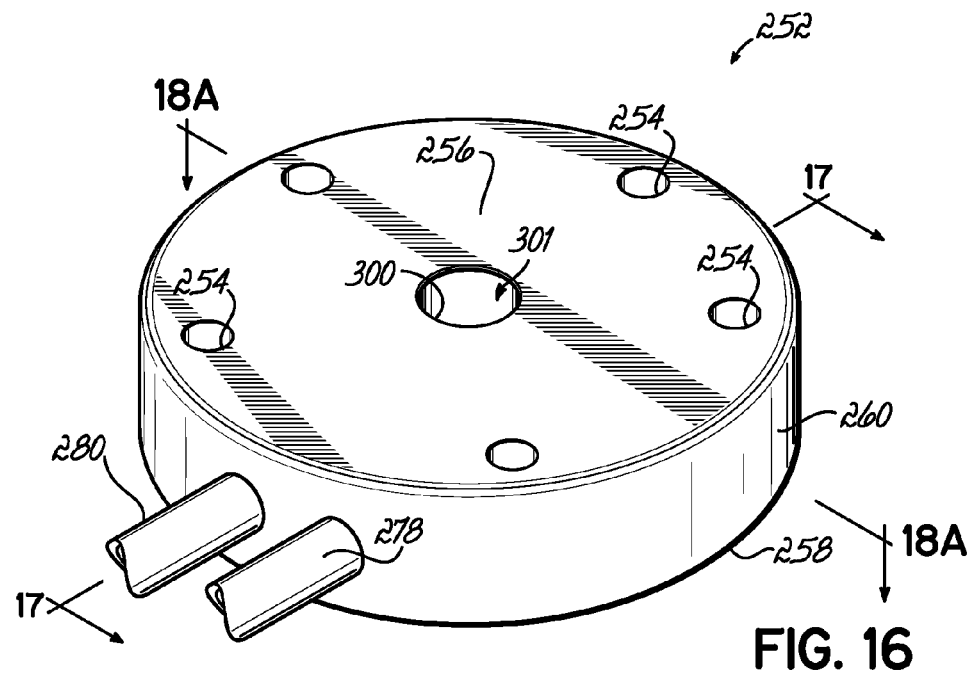
Figure 17:
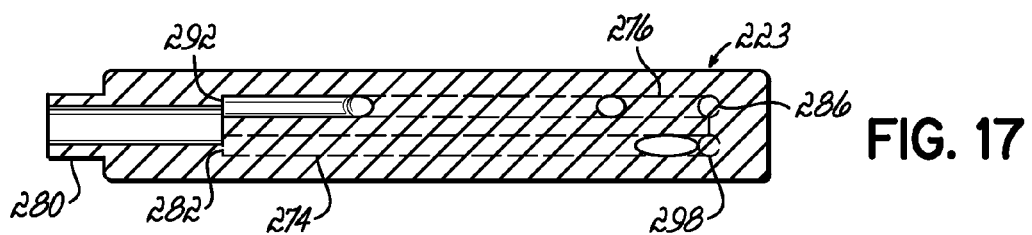
Figure 18A:
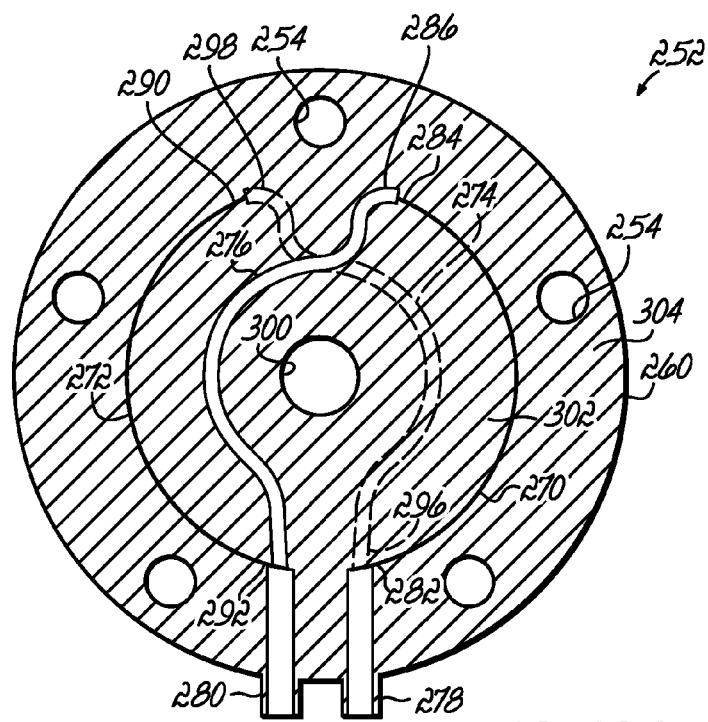
Figure 18B:
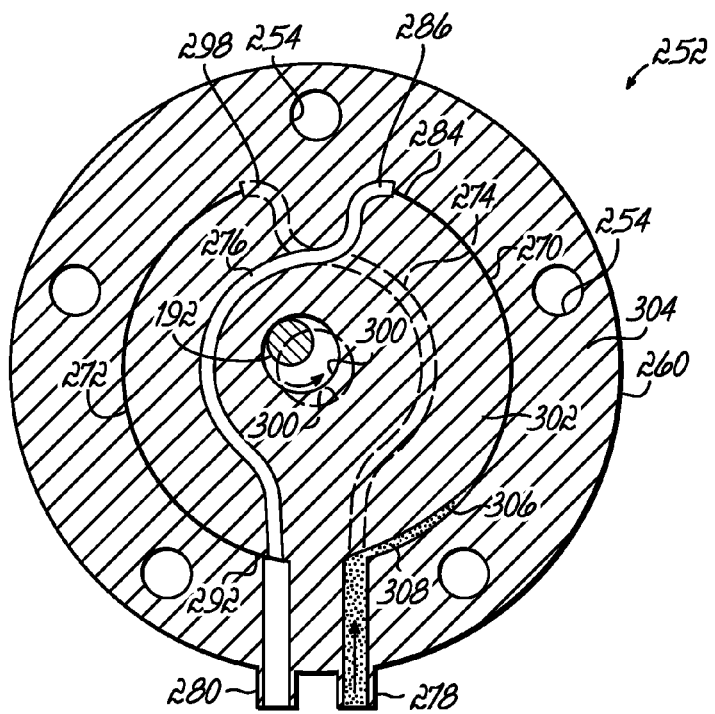
Figure 18C:
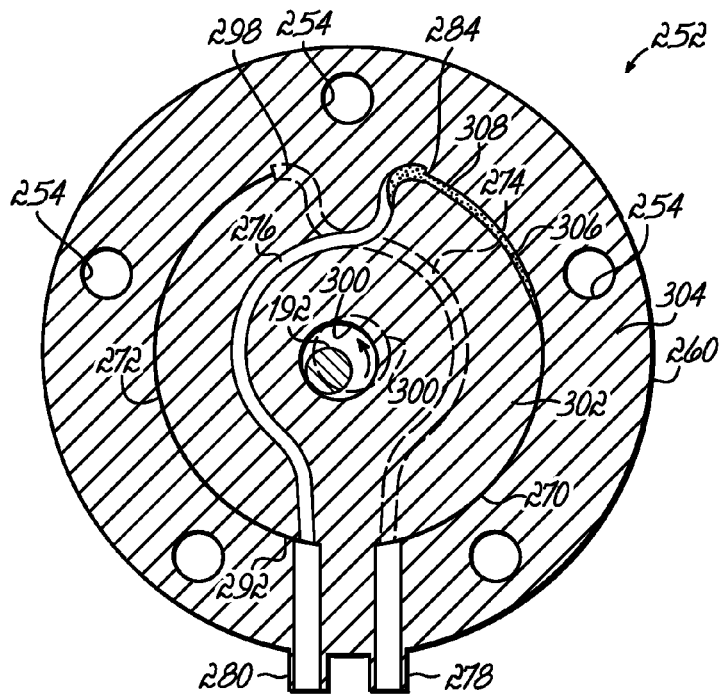
Figure 18D:
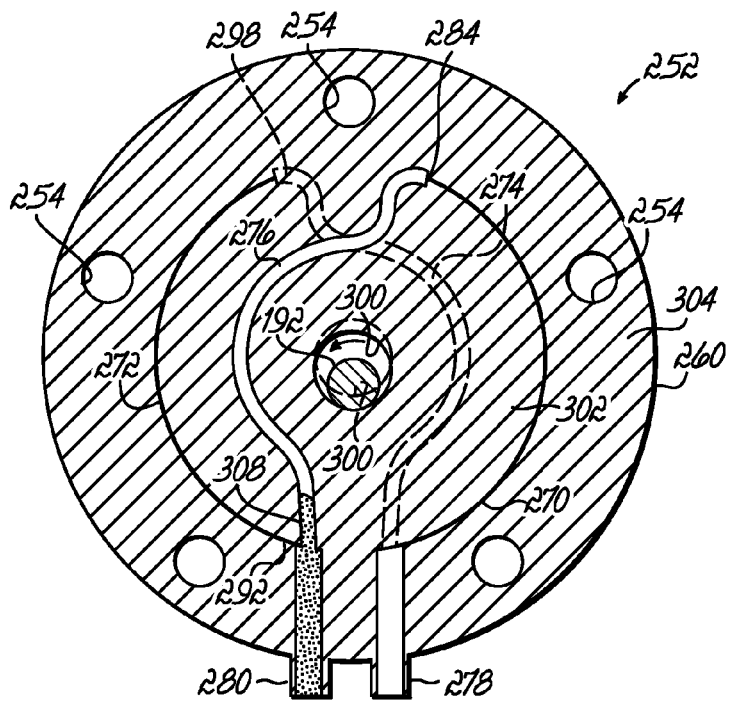
Figure 18E:
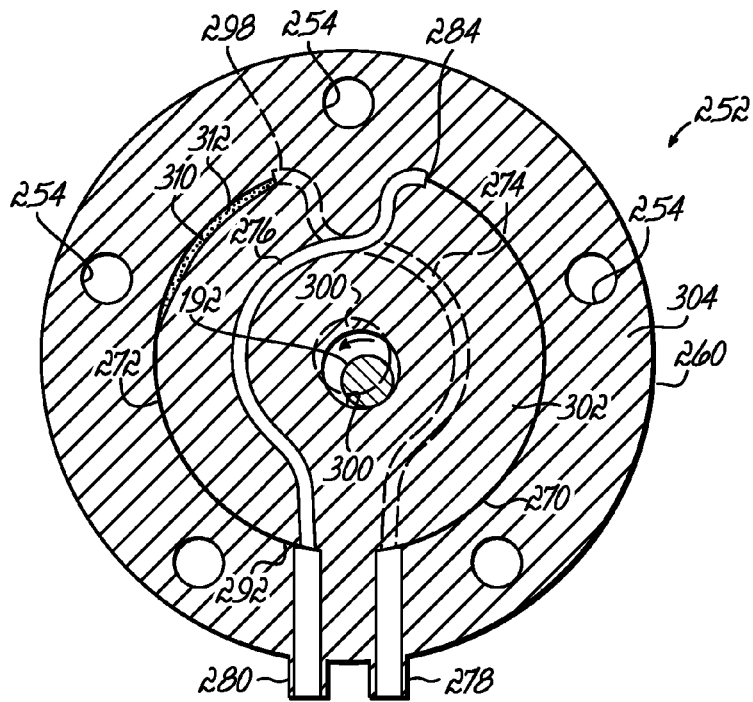
Figure 18F:
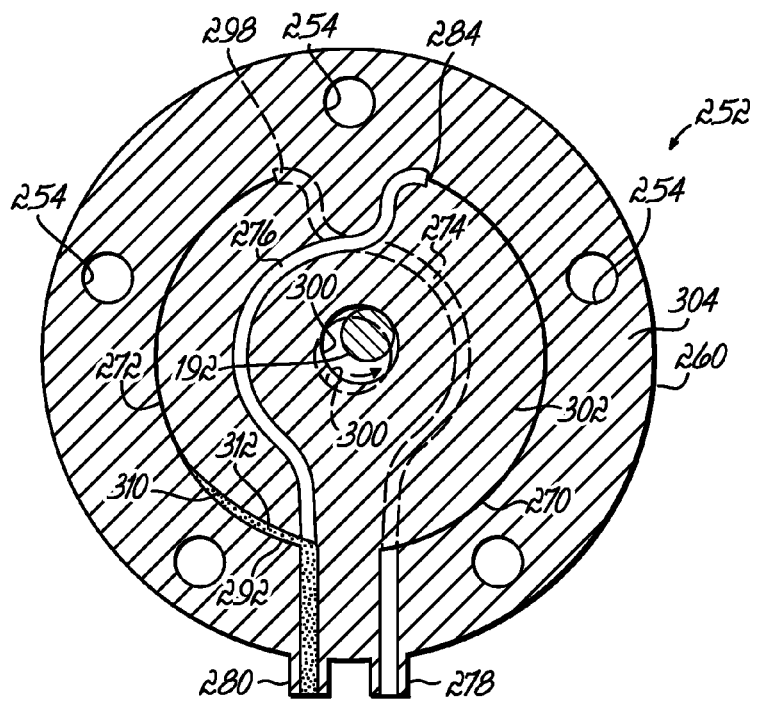
Figure 19:
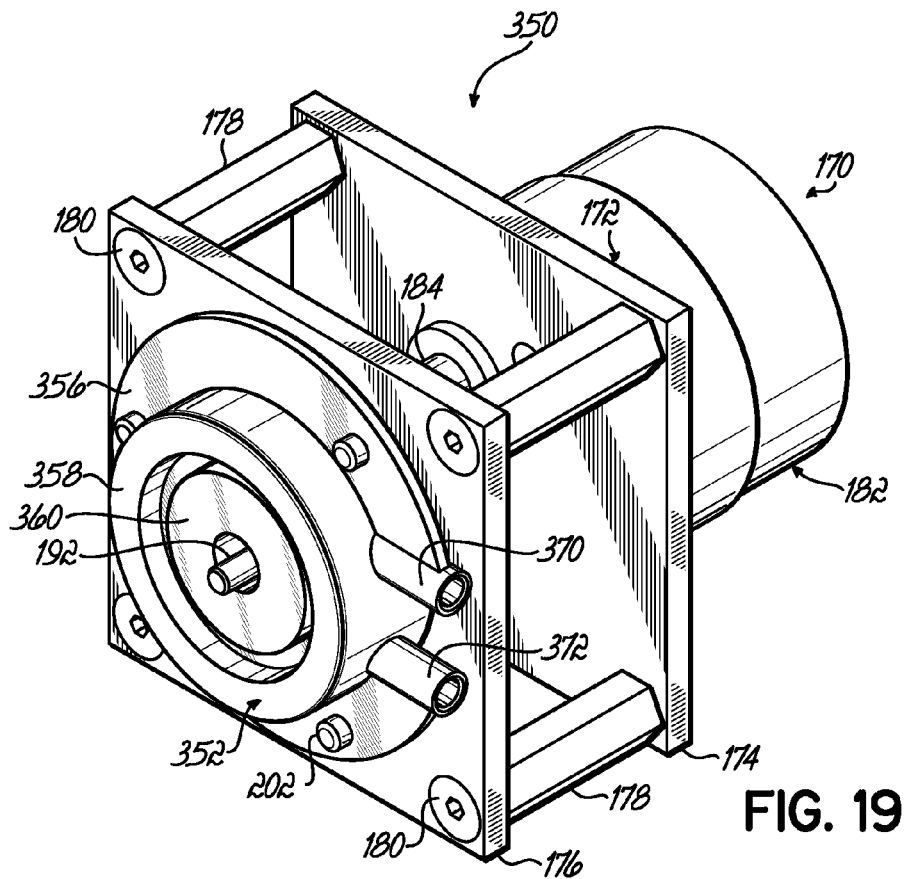
Figure 20:
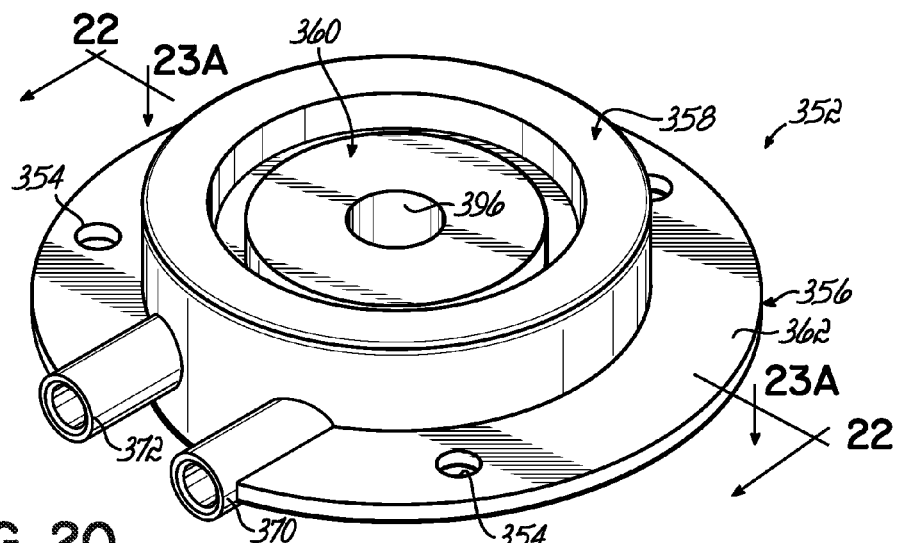
Figure 21:
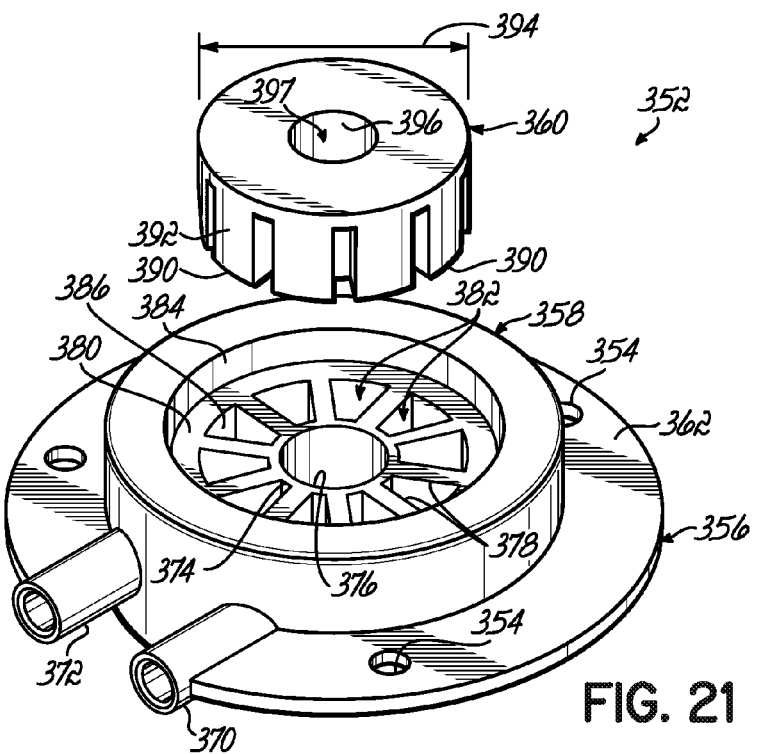
Figure 22:
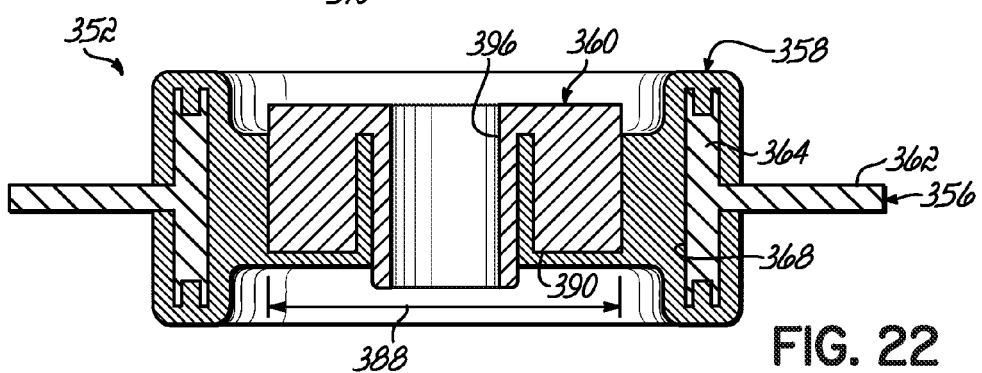
Figure 23A:
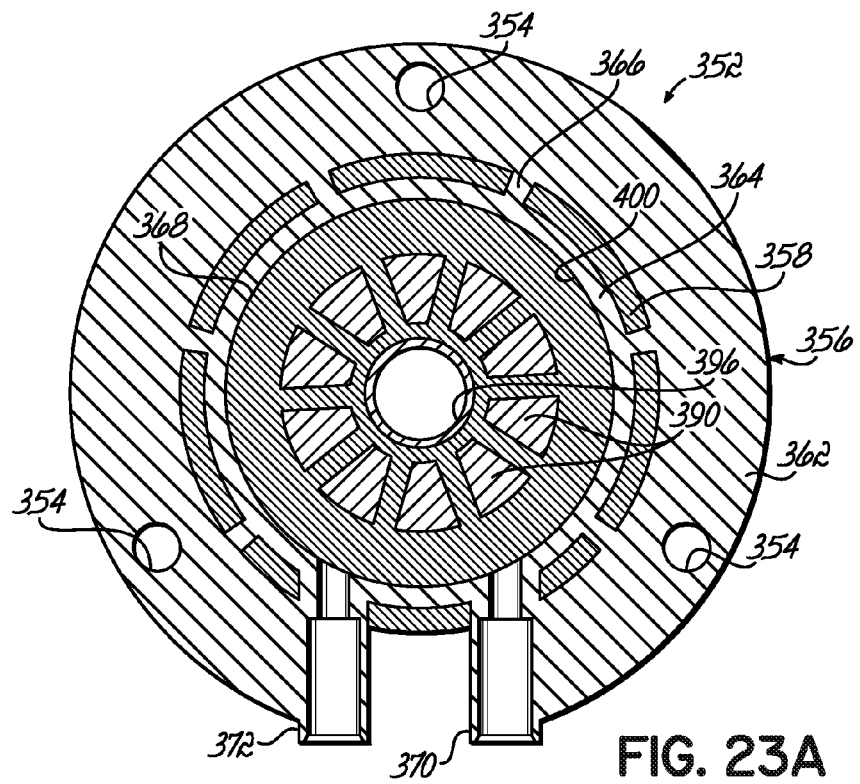
Figure 23B:
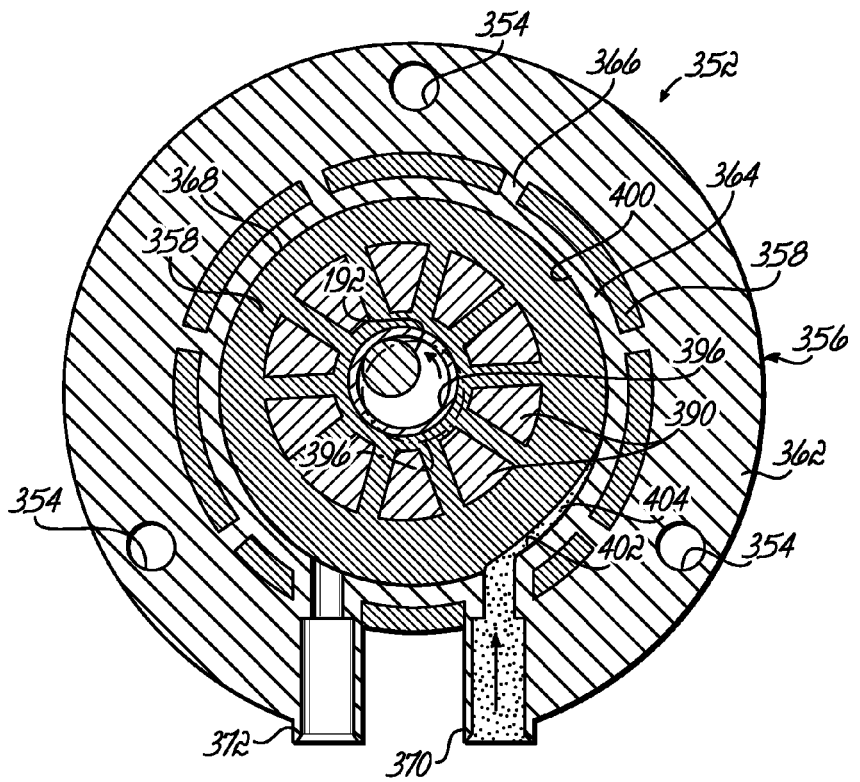
Figure 23C:
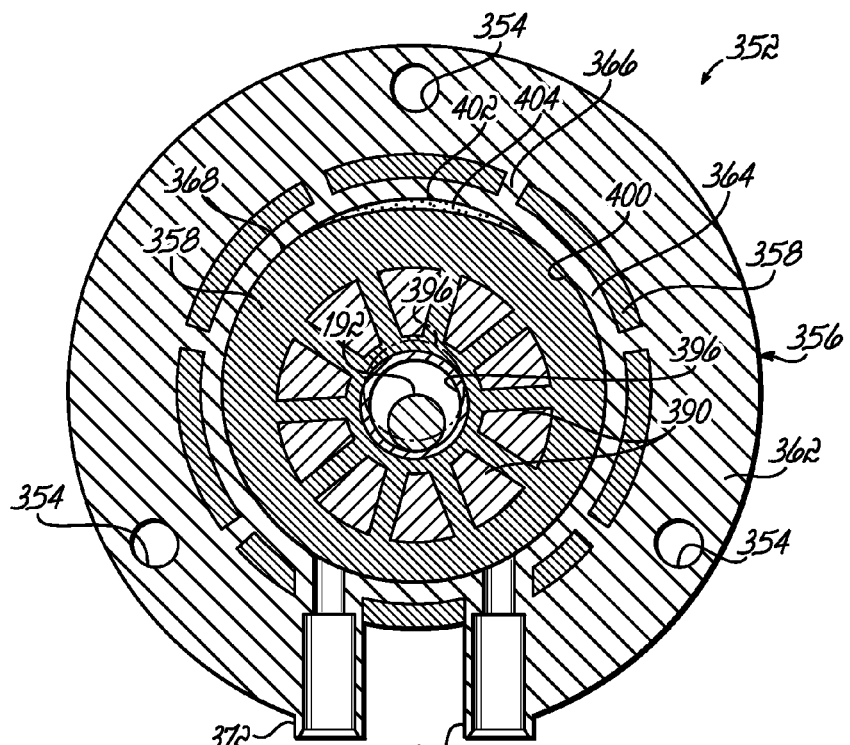
Figure 23D:
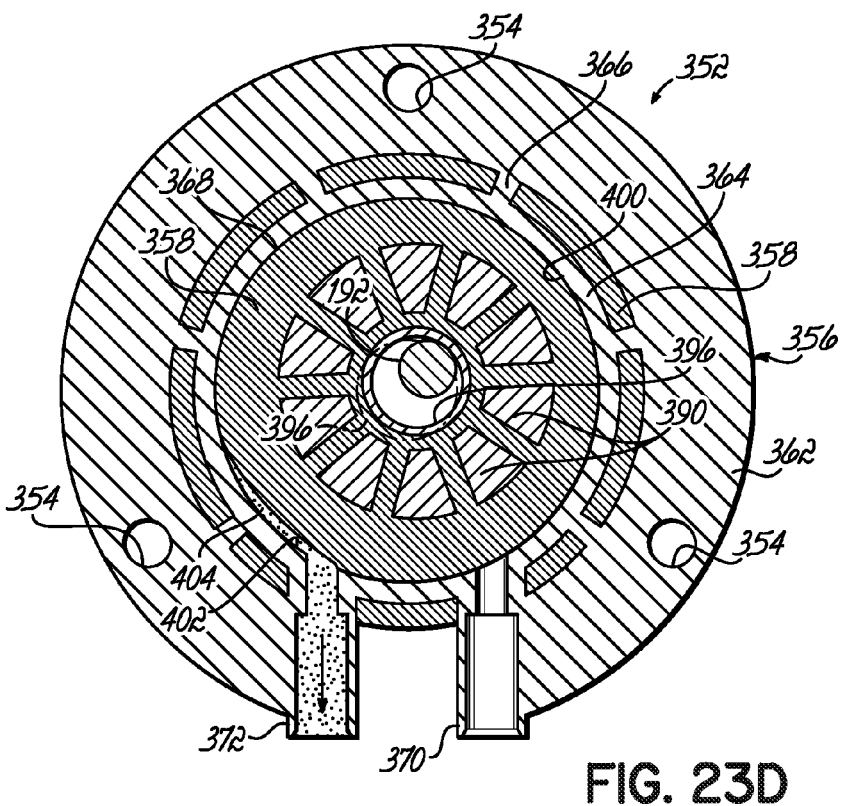
Figure 24:
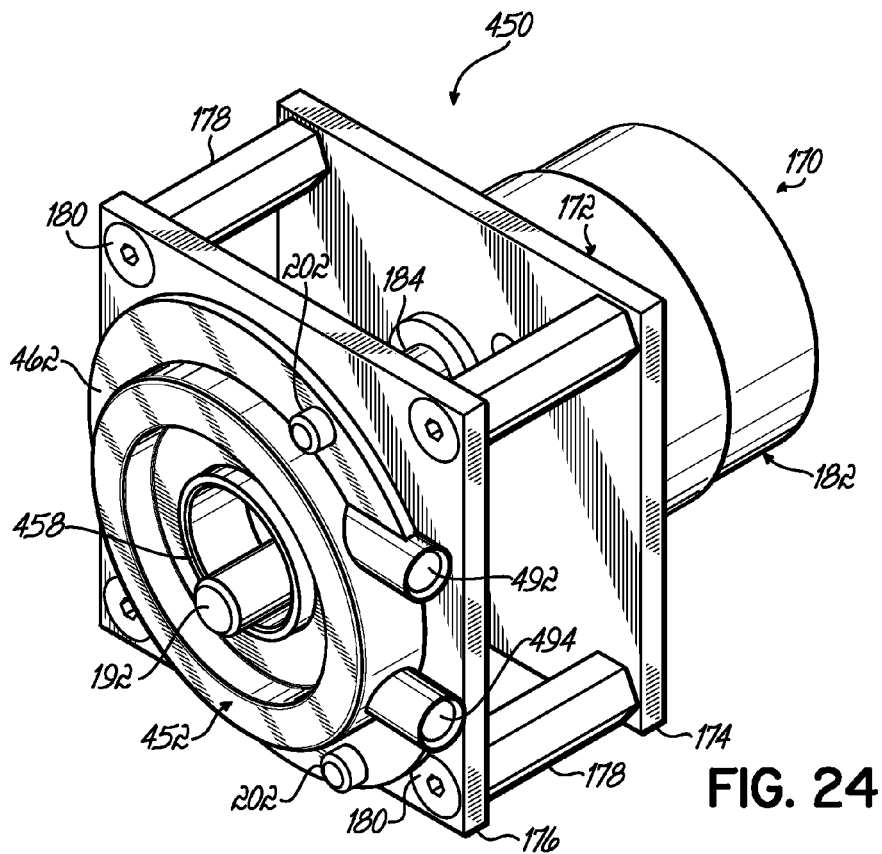
Figure 25:
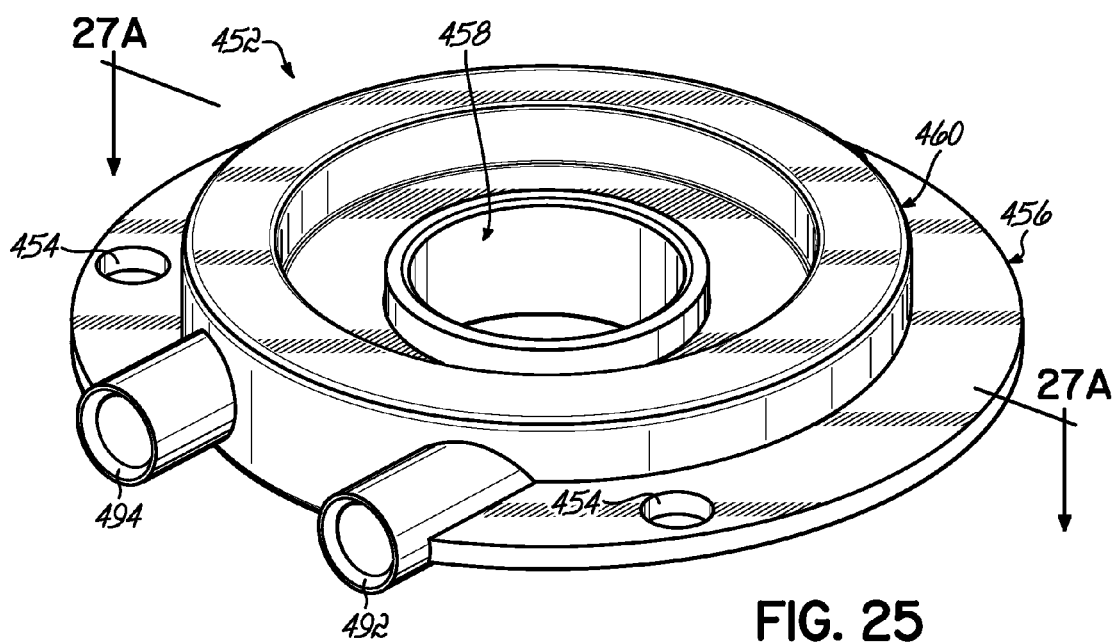
Figure 26:
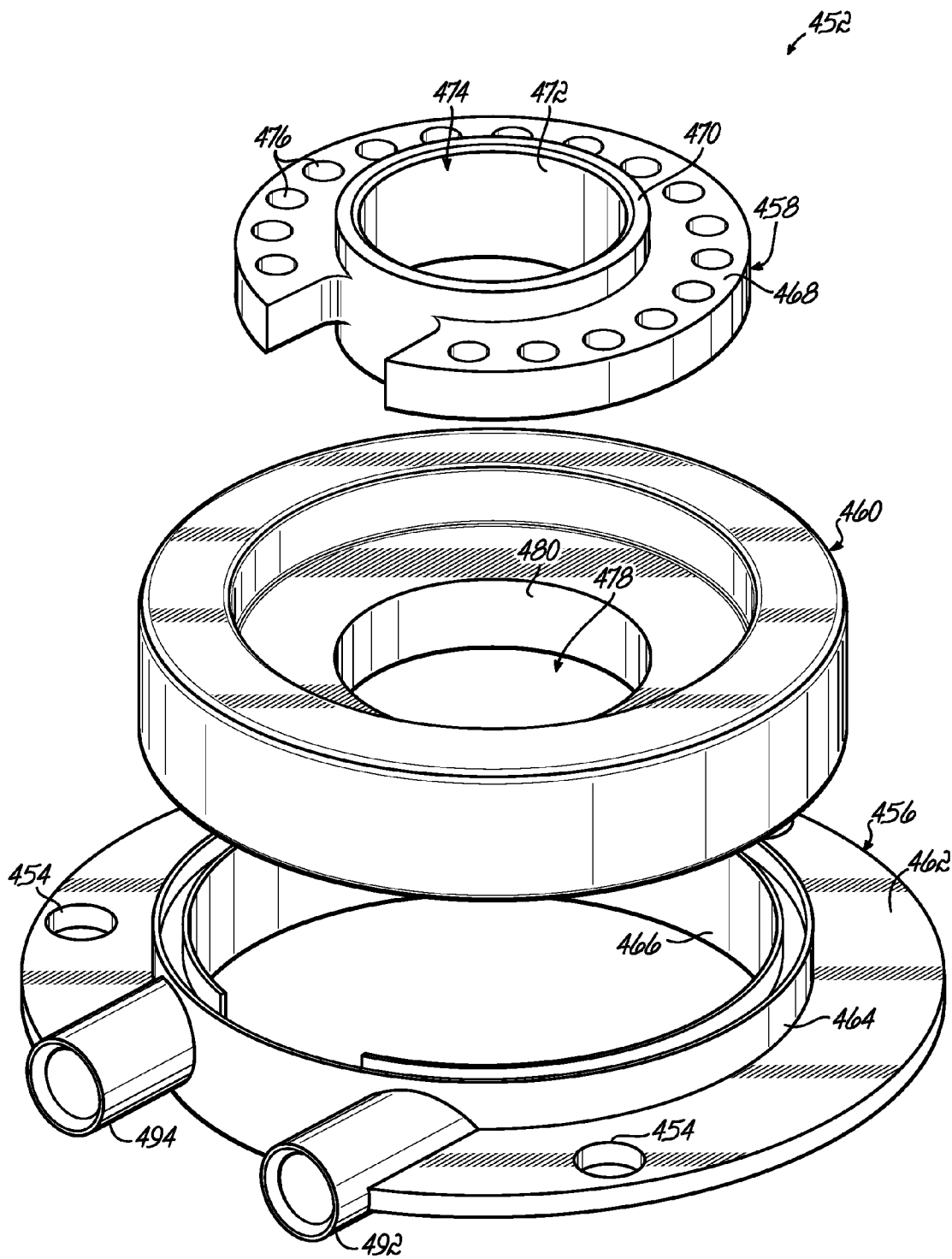
Figure 27A:
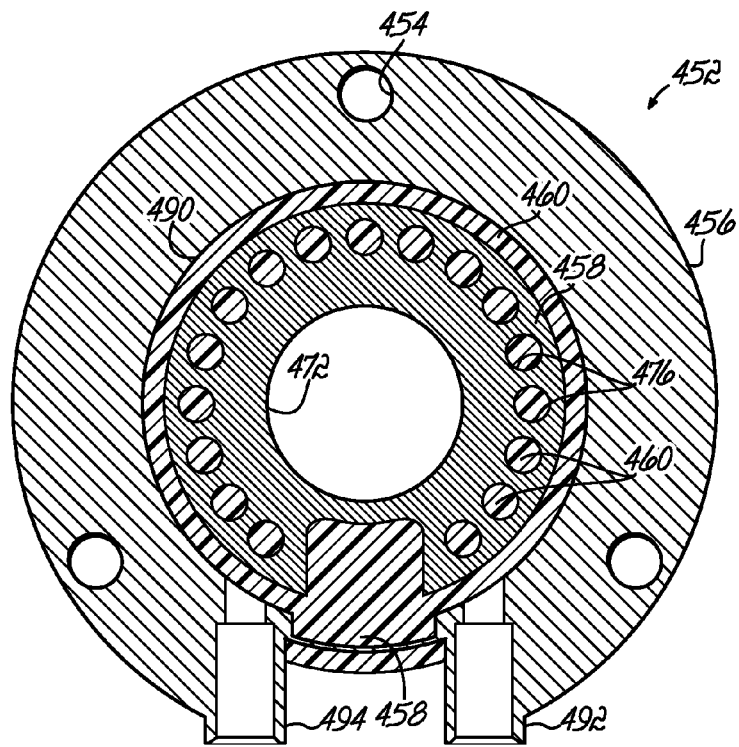
Figure 27B:
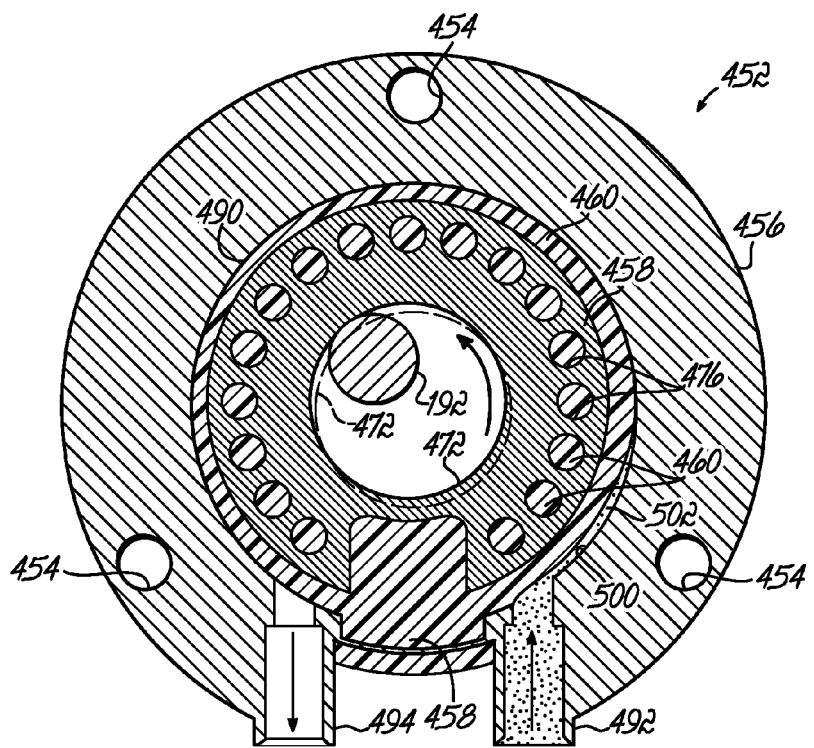
Figure 27C:
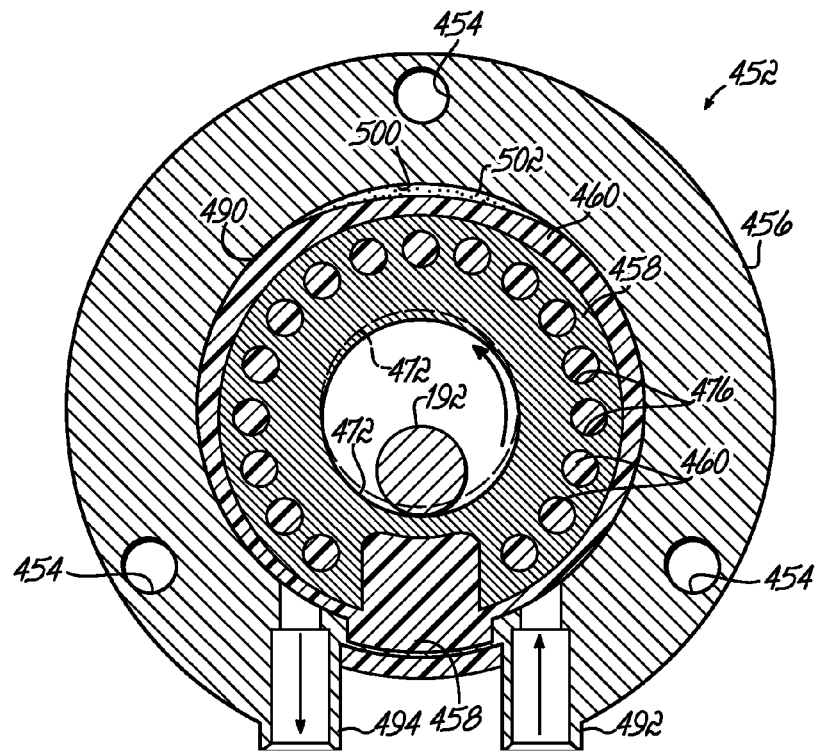
Figure 27D:
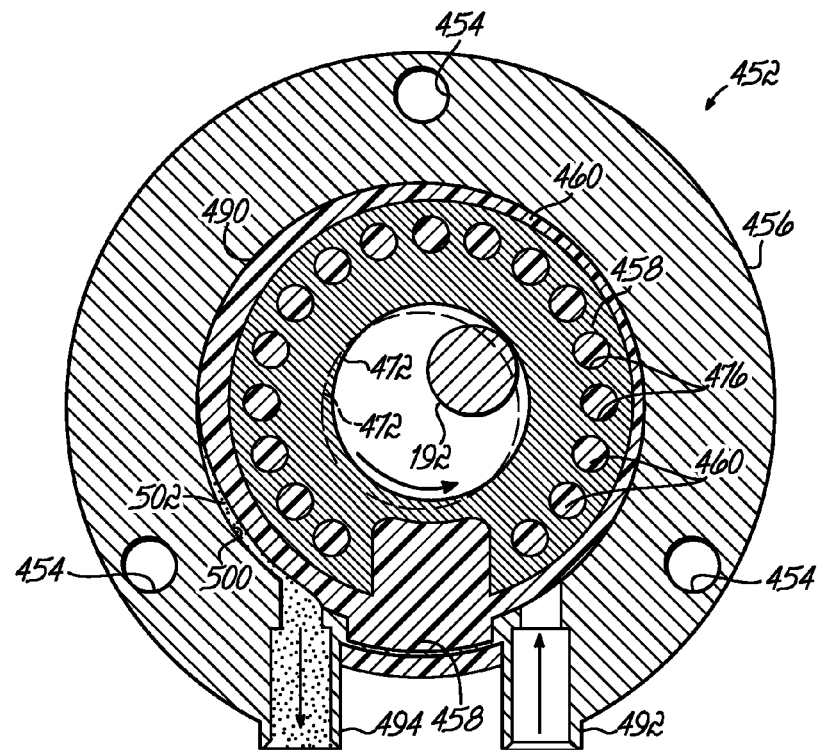
Figure 28:
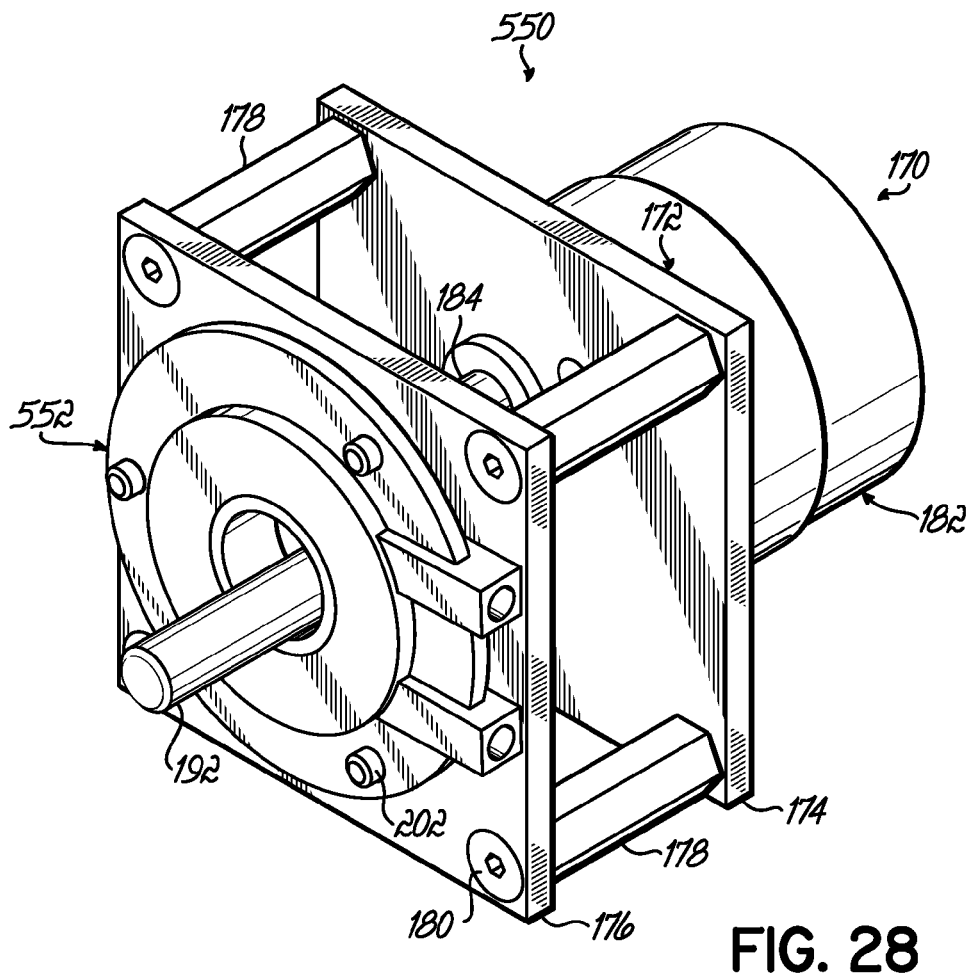
Figure 29:
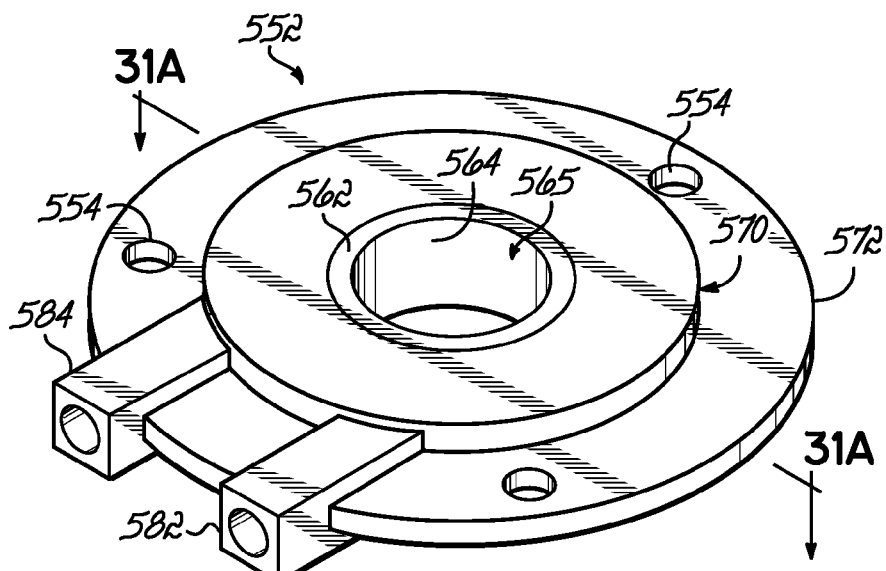
Figure 30:
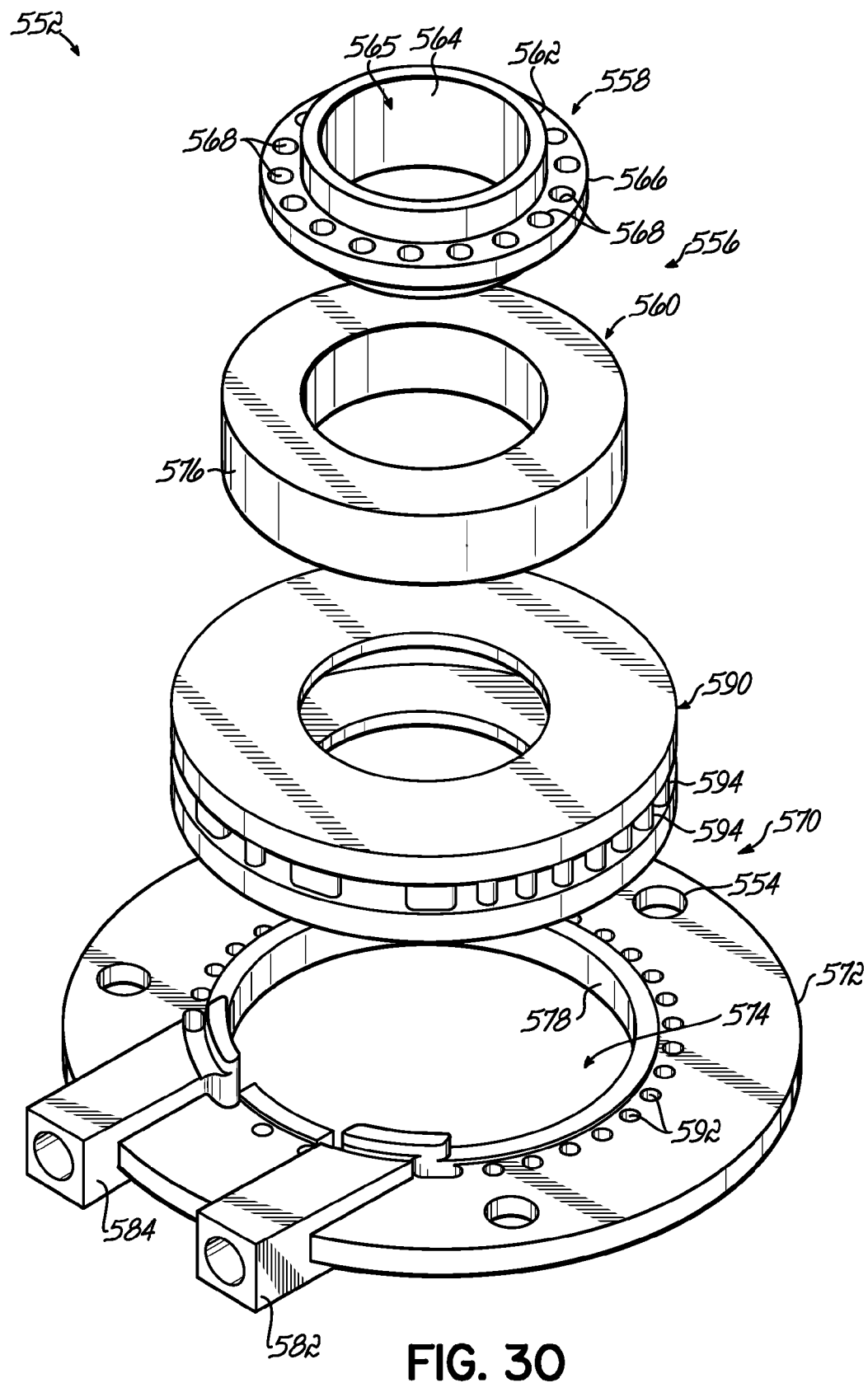
Figure 31A:
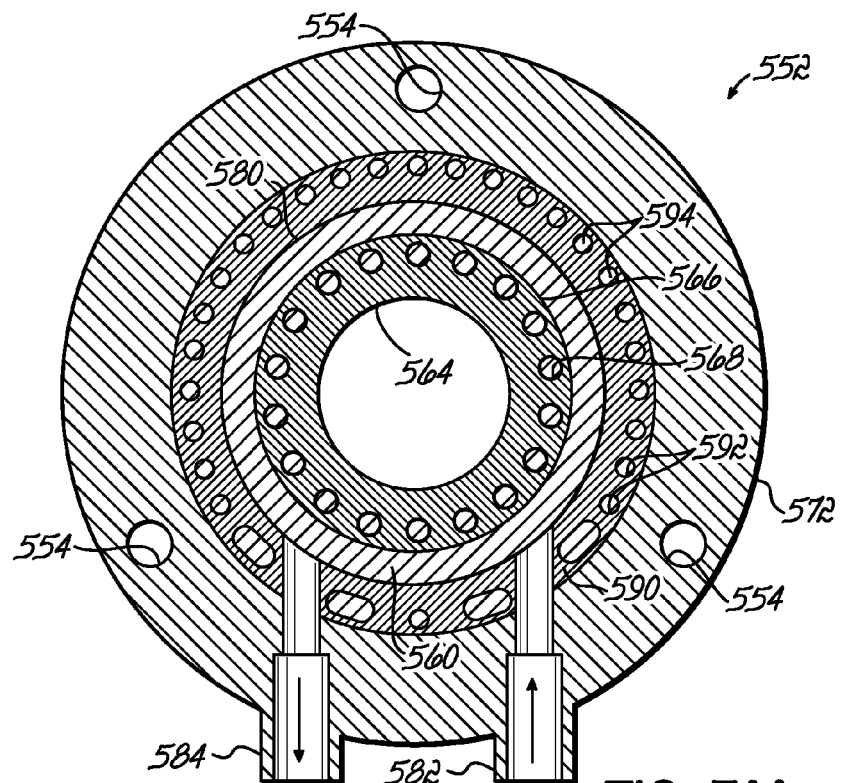
Figure 31B:
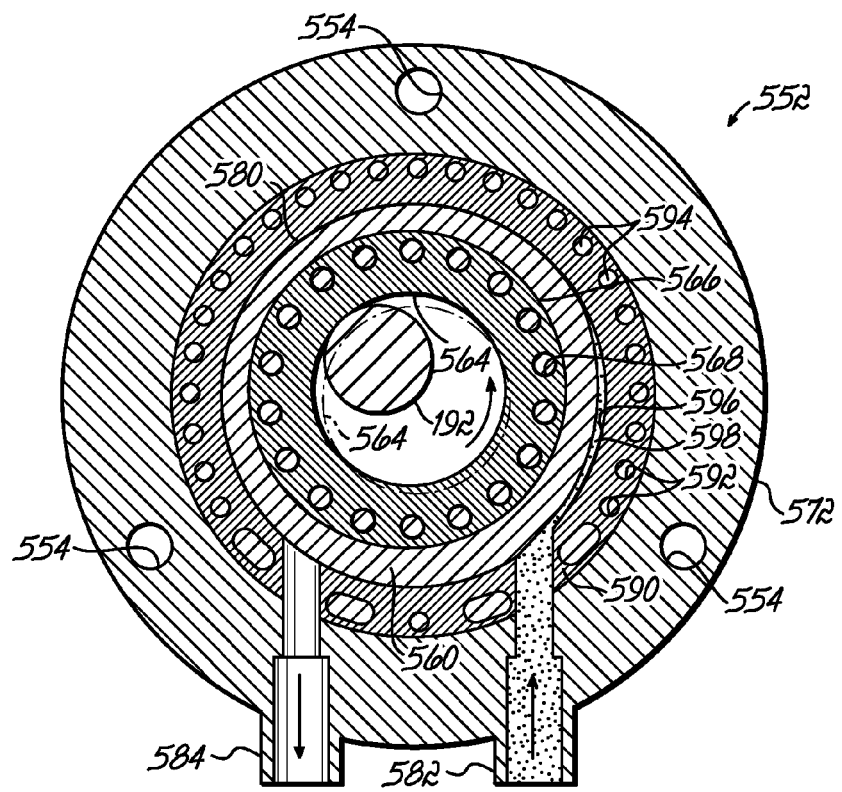
Figure 31C:
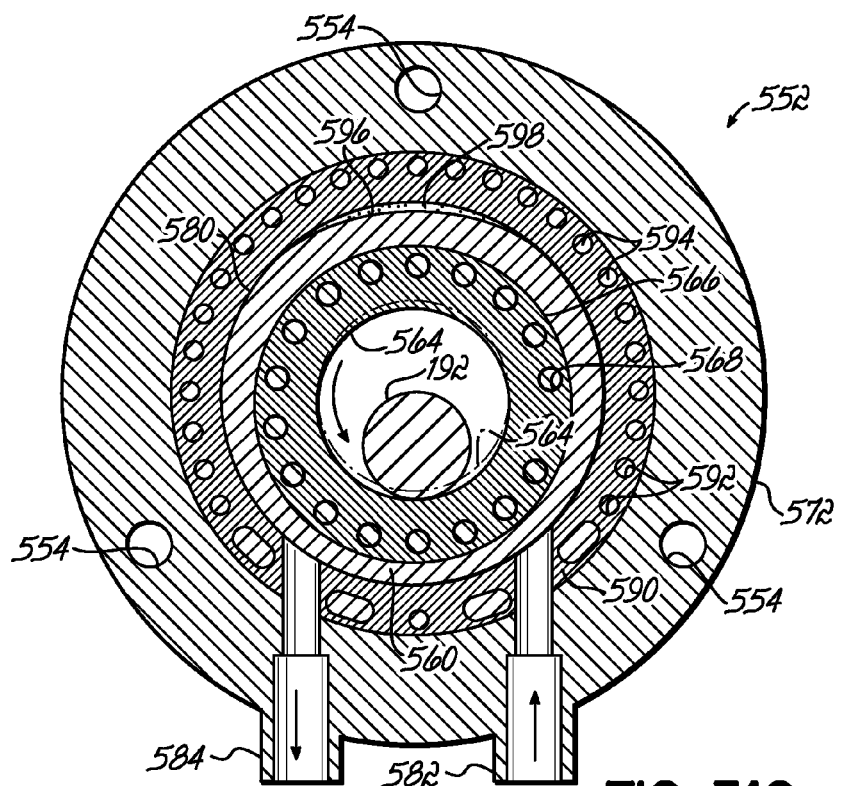
Figure 31D:
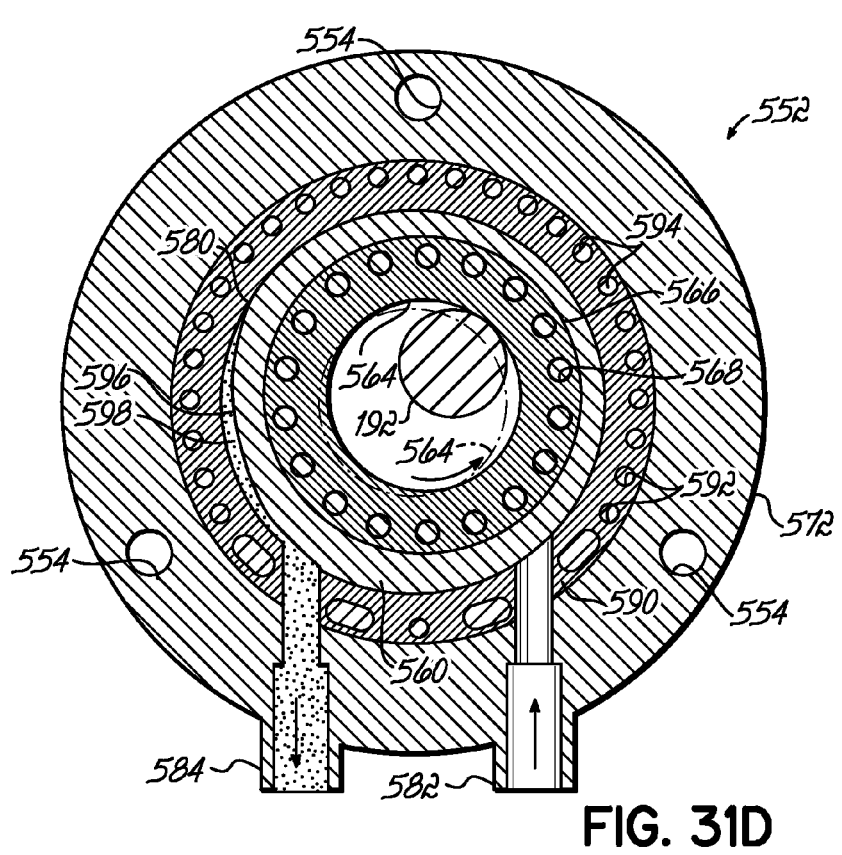
Figure 32:
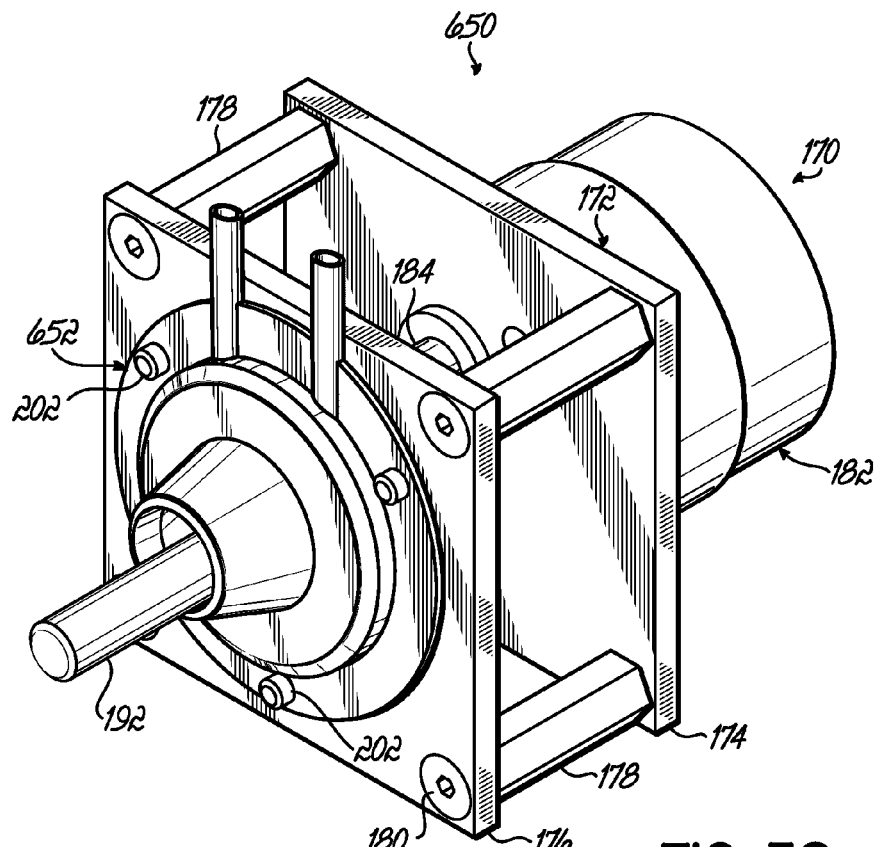
Figure 33:
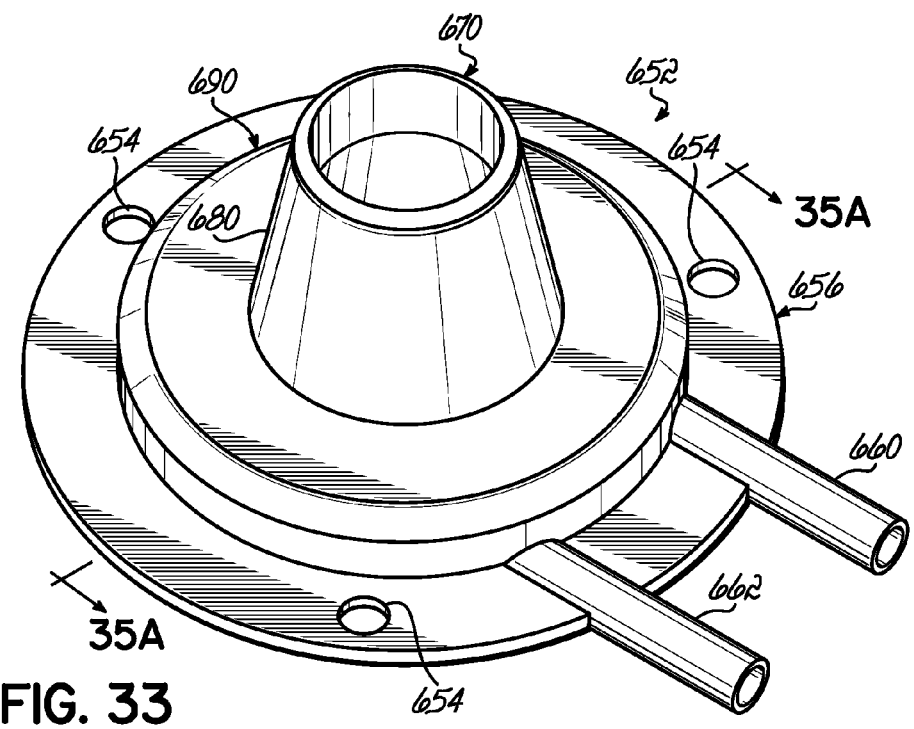
Figure 34:
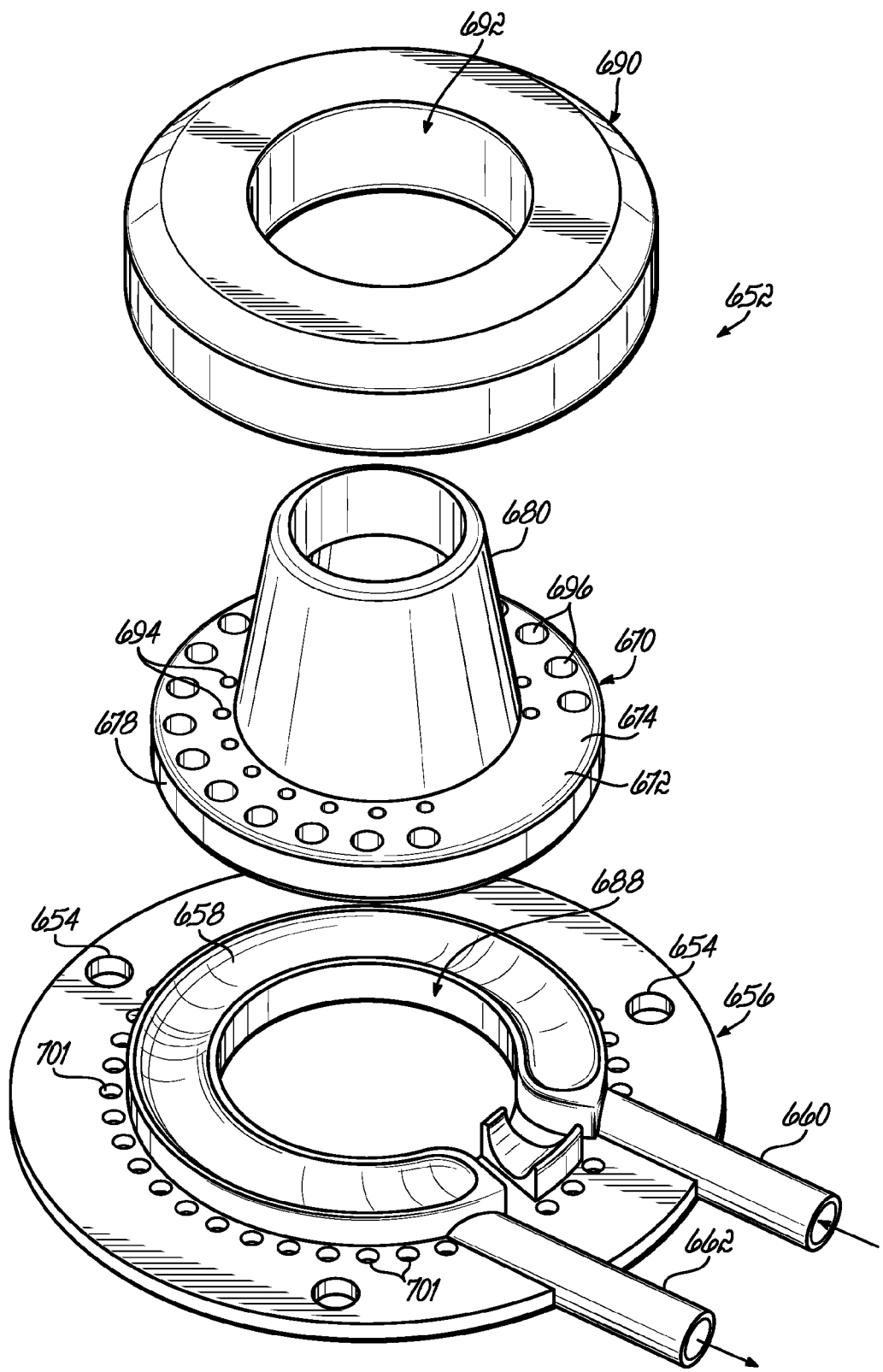
Figure 35A:
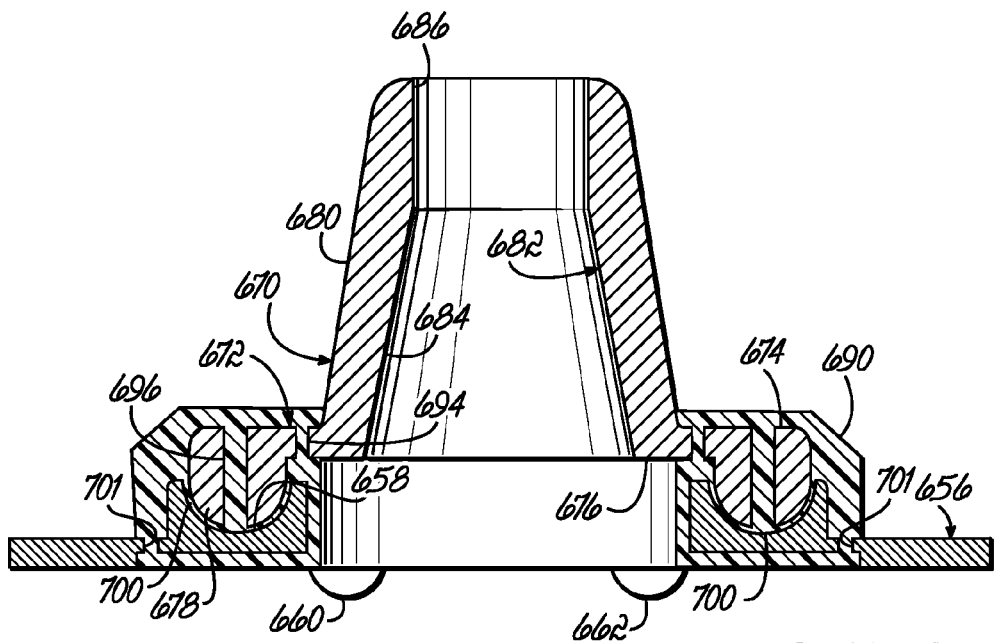
Figure 35B:
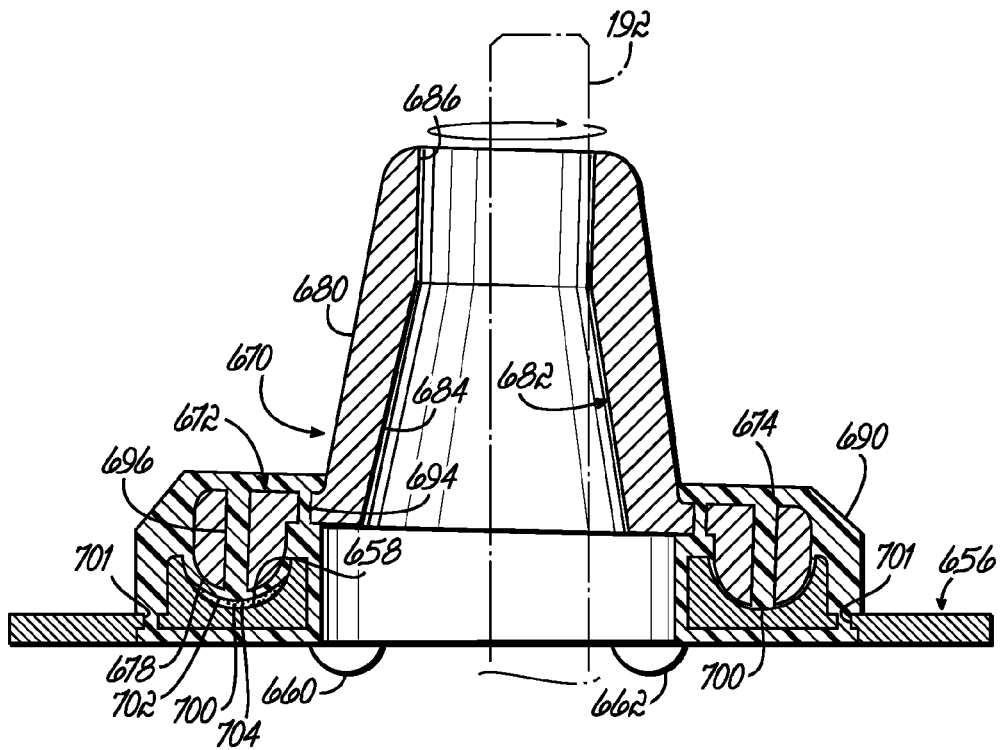
Figure 35C:
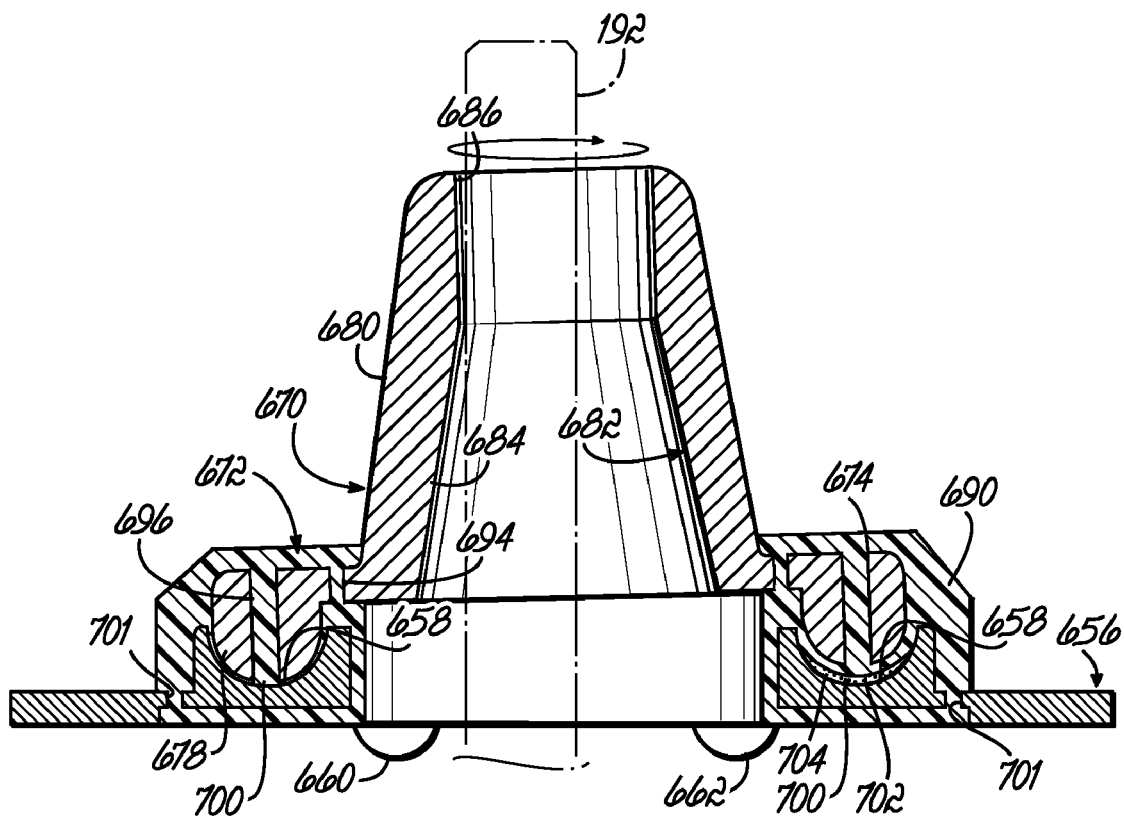

FIG. 4E is a cross-sectional view similar to FIGS. 4A-4D but with the cavity and the fluid therein shown initially in FIG. 4B propagated to the outlet port, the cavity and the fluid therein shown initially in FIG. 4C propagated to a position intermediate the inlet and outlet ports and a third cavity created proximate the inlet port, with fluid being drawn into the cavity, as a result of forces exerted by the actuator on the pump body;

FIG. 5 is a top plan view illustrating another embodiment of a pump in accordance with the principles of the present invention;

FIG. 6 is a perspective view of the pump body illustrated in FIG. 5;

FIG. 7A is a transverse cross-sectional view of the pump body shown in FIGS. 5 and 6 taken along line 7A-7A in FIG. 6, with the included flow passage shown in a closed position;

FIG. 7B is a cross-sectional view similar to FIG. 7A, but with the included flow passage shown in an open position;

FIG. 8A is a longitudinal cross-sectional view taken along line 8A-8A in FIG. 6, with the included flow passage closed;

FIG. 8B is a cross-sectional view similar to FIG. 8A, but with the pump body deformed to create a cavity in the flow passage at a location proximate the inlet port, with fluid drawn into the cavity, as a result of forces exerted by the actuating device on the pump body;

FIG. 8C is a cross-sectional view similar to FIGS. 8A-8B but with the cavity and the fluid therein shown in FIG. 8B propagated to a position intermediate the inlet and outlet ports as a result of forces exerted by the actuating device on the pump body;

FIG. 8D is a cross-sectional view similar to FIGS. 8A-8C, but with the cavity and the fluid therein shown in FIGS. 8B and 8C propagated to the outlet port and a second cavity created proximate the inlet port with fluid being drawn into the cavity, as a result of forces exerted by the actuating device on the pump body;

FIG. 9 is a perspective view of another embodiment of a pump in accordance with the principles of the present invention;

FIG. 10 is a perspective view of the pump body shown in FIG. 9;

FIG. 11A is a cross-sectional view taken along line 11A-11A in FIG. 10, with the included flow passage shown in a closed position;

FIG. 11B is a cross-sectional view similar to FIG. 11A, but with the pump body deformed to create a cavity in the flow passage at a location proximate the inlet port, with fluid drawn into the cavity, as a result of forces exerted by the actuating device on the pump body;

FIG. 11C is a cross-sectional view similar to FIGS. 11A-11B, but with the cavity and the fluid therein shown in FIG. 11B propagated toward the outlet port as a result of forces exerted by the actuating device on the pump body;

FIG. 11D is a cross-sectional view similar to FIGS. 11A-11C, but with the cavity and the fluid therein shown in FIGS. 11B-11C propagated to the outlet port as a result of forces exerted by the actuating device on the pump body;

FIG. 12 is a side elevation view of the pump shown in FIG. 9;

FIG. 13 is an exploded perspective view of the pump shown in FIGS. 9 and 12;

FIG. 14 is an end view of the pump shown in FIGS. 9, 12 and 13;

FIG. 15 is a perspective view of another embodiment of a pump in accordance with the principles of the present invention;

FIG. 16 is a perspective view of the pump body shown in FIG. 15;

FIG. 17 is a cross-sectional view taken along line 17-17 in FIG. 16;

FIG. 18A is a cross-sectional view taken along line 18A-18A in FIG. 16, with both of the included flow passages shown in a closed position;

FIG. 18B is a cross-sectional view similar to FIG. 18A but with the pump body deformed to create a cavity in one of the flow passages at a location proximate the inlet port, with fluid drawn into the cavity, as a result of forces exerted by the actuating device on the pump body;

FIG. 18C is a cross-sectional view similar to FIGS. 18A-18B, but with the cavity and the fluid therein shown in FIG. 18B propagated to a proximate end of a first open conduit in fluid communication with the outlet port;

FIG. 18D is a cross-sectional view similar to FIGS. 18A-18C, but with fluid shown discharging from the first conduit through the outlet port;

FIG. 18E is a cross-sectional view similar to FIGS. 18A-18D, but with the pump body deformed to create a cavity in the other flow passage proximate a distal end of a second open conduit in fluid communication with the inlet port, with fluid drawn into the cavity, as a result of forces exerted by the actuating device on the pump body;

FIG. 18F is a cross-sectional view similar to FIGS. 18A-18E, but with the cavity and the fluid therein shown in FIG. 18E propagated to the outlet port as a result of forces exerted by the actuating device on the pump body;

FIG. 19 is a perspective view of another embodiment of a pump in accordance with the principles of the present invention;

FIG. 20 is a perspective view of the pump body shown in FIG. 19;

FIG. 21 is an exploded perspective view of the pump body shown in FIGS. 19-20;

FIG. 22 is a cross-sectional view taken along line 22-22 in FIG. 20;

FIG. 23A is a cross-sectional view taken along line 23A-23A in FIG. 20, with the included flow passage shown in a closed position;

FIG. 23B is a cross-sectional view similar to FIG. 23A, but with the pump body deformed to create a cavity in the flow passage proximate the inlet port, with fluid drawn into the cavity, as a result of forces exerted by the actuating device on the pump body;

FIG. 23C is a cross-sectional view similar to FIGS. 23A-23B, but with the cavity and the fluid therein shown in FIG. 23B propagated to a position intermediate the inlet and outlet ports;

FIG. 23D is a cross-sectional view similar to FIGS. 23A-23C, but with the cavity and the fluid therein shown in FIGS. 23B-23C propagated to a position proximate the outlet port, with the cavity and the fluid therein being in fluid communication with the outlet port;

FIG. 24 is a perspective view of another embodiment of a pump in accordance with the principles of the presenting invention;

FIG. 25 is a perspective view of the pump body shown in FIG. 24;

FIG. 26 is an exploded perspective view of the pump body shown in FIGS. 24-25;

FIG. 27A is a cross-sectional view taken along line 27A-27A in FIG. 25, with the included flow passage shown in a closed position;

FIG. 27B is a cross-sectional view similar to FIG. 27A, but with the pump body deformed to create a cavity in the flow passage proximate the inlet port, with fluid drawn into the cavity, as a result of forces exerted by the actuating device on the pump body;

FIG. 27C is a cross-sectional view similar to FIGS. 27A-27B, but with the cavity and the fluid therein shown in FIG. 27B propagated to a position intermediate the inlet and outlet ports;

FIG. 27D is a cross-sectional view similar to FIGS. 27A-27C, but with the cavity and the fluid therein shown in FIGS. 27B-27C propagated to a position proximate the outlet port, with the cavity and the fluid therein being in fluid communication with the outlet port;

FIG. 28 is a perspective view of another embodiment of a pump in accordance with the principles of the present invention;

FIG. 29 is a perspective view of the pump body shown in FIG. 28;

FIG. 30 is an exploded perspective view of the pump body shown in FIGS. 28-29;

FIG. 31A is a cross-sectional view, taken along line 31A-31A in FIG. 29, with the included flow passage shown in a closed position;

FIG. 31B is a cross-sectional view similar to FIG. 31A, but with the pump body deformed to create a cavity in the flow passage proximate the inlet port, with fluid drawn into the cavity, as a result of forces exerted by the actuating device on the pump body;

FIG. 31C is a cross-sectional view similar to FIGS. 31A-31B, but with the cavity and the fluid therein shown in FIG. 31B propagated to a position intermediate the inlet and outlet ports;

FIG. 31D is a cross-sectional view similar to FIGS. 31A-31C, but with the cavity and the fluid therein shown in FIGS. 31B-31C propagated to a position proximate the outlet port, with the cavity and the fluid therein being in fluid communication with the outlet port;

FIG. 32 is a perspective view of another embodiment of a pump in accordance with the principles of the present invention;

FIG. 33 is a perspective view of the pump body shown in FIG. 32;

FIG. 34 is an exploded perspective view of the pump body shown in FIGS. 32-33;

FIG. 35A is a cross-sectional view taken along line 35A-35A in FIG. 33, with the included flow passage shown in a closed position;

FIG. 35B is a cross-sectional view similar to FIG. 35A, but with the pump body deformed to create a cavity in the flow passage proximate the inlet port, with fluid drawn into the cavity, as a result of forces exerted by the actuating device on the pump body; and FIG. 35C is a cross-sectional view similar to FIGS. 35A-35B, but with the cavity and the fluid therein shown in FIG. 35B propagated to a position proximate the outlet port, with the cavity and the fluid therein being in fluid communication with the outlet port.

DESCRIPTION

Figure 1:
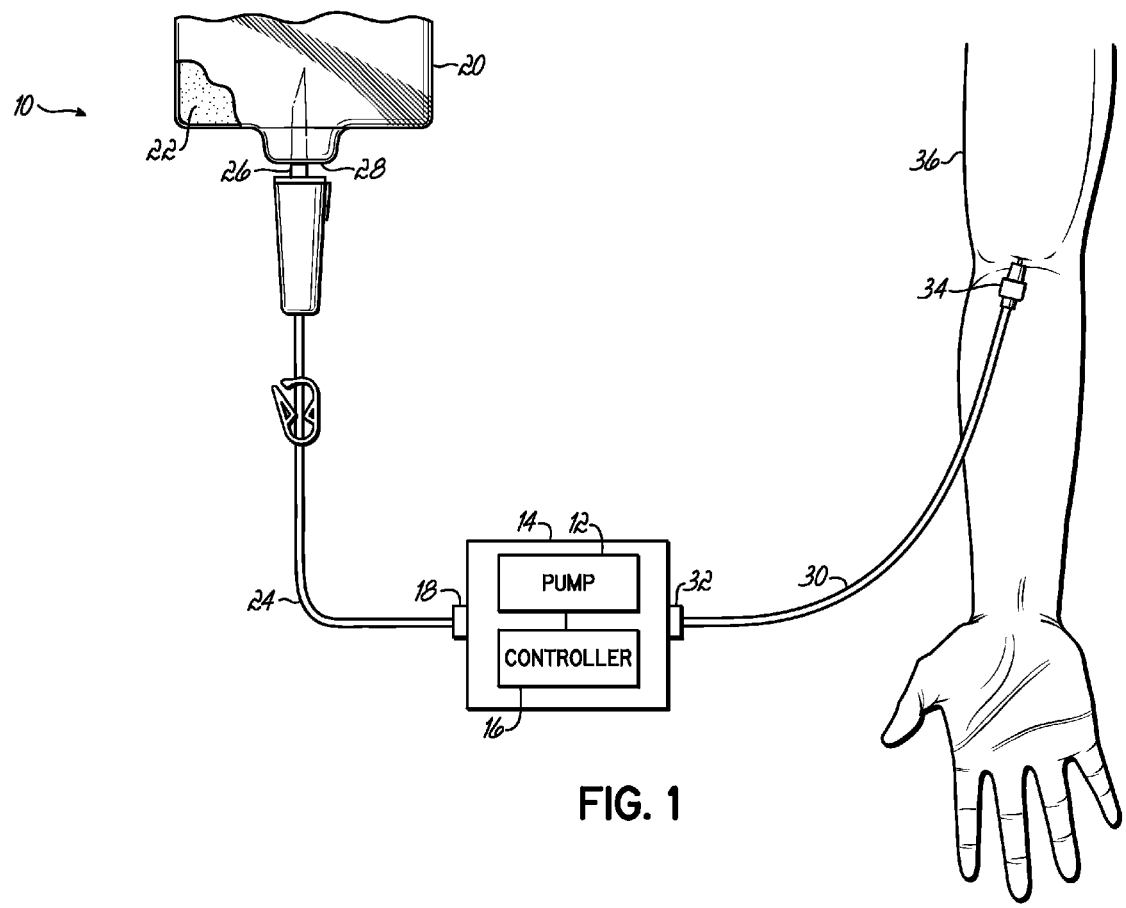
FIG. 1 is a schematic illustration of a medical dispensing system, for dispensing a fluid intravenously to a patient, that incorporates a progressive cavity propagation pump in accordance with the principles of the present invention.

Referring now to the drawings, FIG. 1 illustrates a system 10 for dispensing medical fluids intravenously to a patient, with system 10 incorporating a progressive cavity propagation pump, indicated schematically at 12, in accordance with the principles of the present invention. Any progressive cavity propagation pump in accordance with the principles of the present invention, including those that are subsequently described and illustrated, can be incorporated in system 10. Pump 12 can be disposed within a enclosure, illustrated schematically at 14, and can be electrically coupled to a controller 16 that is also disposed within the enclosure 14, and controls the operation of pump 12.

A fluid inlet (not shown) of pump 12 is fluidically coupled to a source of fluid to be dispensed which can comprise a bag 20, commonly referred to as an IV bag, containing a fluid 22 therein. The fluid 22 can comprise a variety of medications and can also include other fluids, such as saline solution, as known in the art. The system 10 further includes a first section of tubing 24 that can comprise a single piece of tubing or multiple pieces of interconnected tubing. Tubing 24 can pass through a tubing inlet 18 of enclosure 14, and be fluidicly coupled to a fluid inlet (not shown in FIG. 1) of pump 12 by one or more conduits and fluid connectors (not shown). The opposite end of tubing 24 can terminate in a spike 26 adapted to pierce a port 28 of the IV bag 22.

System 10 also includes a second section of tubing 30 that can comprise a single piece of tubing or multiple pieces of interconnected tubing. Tubing 30 can pass through a tubing outlet 32 of enclosure 14, and be fluidicly coupled to a fluid outlet (not shown in FIG. 1) of pump 12 by one or more conduits and fluid connectors (not shown). The opposite end of tubing 30 can terminate in a catheter 34 inserted intravenously into an arm 36 of a patient.

Figure 2:
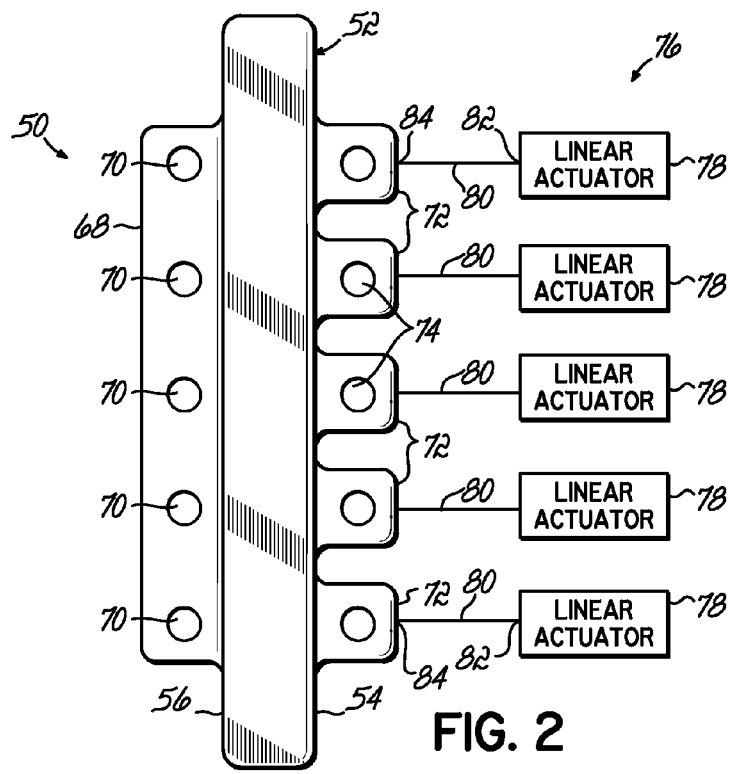
FIG. 2 is a top plan view of one embodiment of a pump in accordance with the principles of the present invention, with the included actuating device illustrated schematically.
Figure 3:
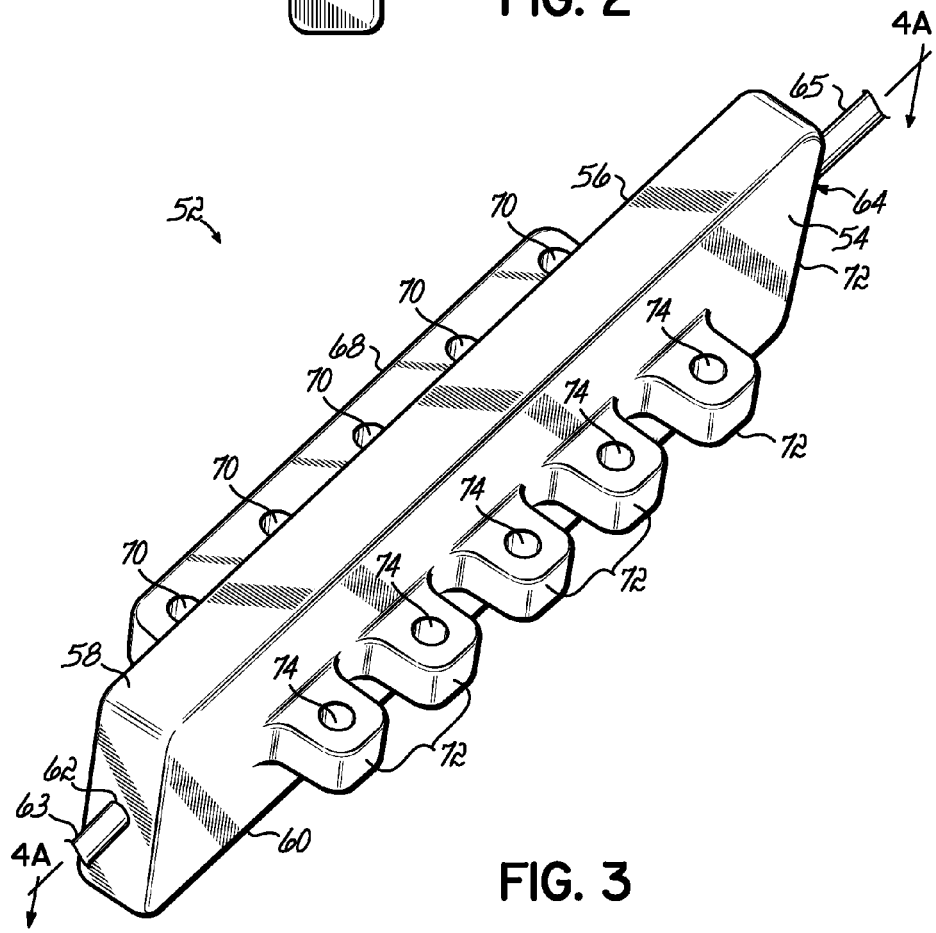
FIG. 3 is a perspective view of the body of the pump illustrated in FIG. 2.

FIGS. 2 and 3 illustrate a progressive cavity propagation pump 50 in accordance with the principles of the present invention. Pump 50 includes a body 52 having first 54 and second 56 longitudinally extending portions that are made of an elastomeric material, which can be silicone for example. The body 52 further includes upper 58 and lower 60 surfaces. Pump 50 also includes an inlet port 62 and an outlet port 64, with ports 62 and 64 coupled to body 52. Ports 62 and 64 can be integrally formed with body 52. However, in the illustrated embodiment, the inlet 62 and outlet 64 ports are one end of tubes 63 and 65 respectively which are inserted into body 52. A normally closed flow passage 66, shown closed in FIG. 4A, is formed in body 52 and extends between inlet port 62 and outlet port 64 along a substantially linear path. The inlet port 62 and outlet port 64 are fluidicly uncoupled when pump 50 is in a free state condition i.e., when pump 50 is not operated and pump body 52 is not deformed by the subsequently discussed actuating device.

As shown in FIGS. 4A-4E, the flow passage 66 is disposed laterally between the first 54 and second 56 portions of body 52. As shown in FIG. 4A, the first 54 and second 56 portions of body 52 are disposed in abutting relationship with one another when pump 50 is not operated and flow passage 66 is entirely closed. During operation of pump 50, portions 54 and 56 of body 52 are locally separable from one another as subsequently discussed. Flow passage 66 does not extend through the upper 58 and lower 60 surfaces of body 52 to prevent pump 50 from leaking fluid during operation.

Body 52 of pump 50 is adapted to be mounted to a stationary structure such as enclosure 14 shown in FIG. 1. In the illustrated embodiment, portion 56 of body 52 includes a flange 68. Flange 68 is adapted to be mounted to a stationary structure. More particularly, flange 68 includes a plurality of longitudinally spaced apertures 70 formed therein. Flange 68 can be mounted to a stationary structure, such as enclosure 14, with a plurality of fasteners (not shown) such as bolts extending through apertures 70, which can be round holes, and a second plurality of fasteners (not shown) such as nuts to retain the bolts in place and clamp flange 68 to the stationary structure.

Portion 54 of body 52 can include a plurality of tabs 72. Each of the tabs 72 can include an aperture 74 formed therein. Pump 50 further includes an actuating device, indicated generally at 76, that is coupled to the portion 54 of body 52, as shown in FIG. 3. The actuating device 76 includes a plurality of linear actuators 78, each coupled to the portion 54 of body 52. In the illustrated embodiment, the actuating device 76 includes a plurality of actuating members 80. The linear actuators 78 are coupled to portion 54 of body 52 by members 80 and tabs 72. Each of the actuating members 80 is coupled at an end 82 to one of the linear actuators 78 and is coupled at an opposite end 84 to one of the tabs 72.

Each of the linear actuators 78 can be a stepper motor, such as an electrically operated stepper motor. Alternatively, the linear actuators can be a cam or a block of electro-active polymer. Application of electric current to the electro-active polymers can cause the corresponding actuating members 80 to move. The linear actuators 78 can also be any other suitable type of actuator that causes the actuating members 80 to exert push and pull forces on the tabs 72. Each of the actuators 78 can be electrically coupled to a controller, such as controller 16 shown schematically in FIG. 1, that controls the operation of actuators 78.

The operation of pump 50 can be further understood with reference to FIGS. 4A-4E, where tabs 72 are identified as tabs 72a-72e. FIGS. 4A-4E illustrate pump 50 in a plurality of sequential stages of operation, i.e., the condition of pump 50 shown in FIG. 4C occurs after that shown in FIG. 4B, etc. While pump 50 is illustrated with five of the tabs 72, other numbers of tabs 72 can be used within the scope of the present invention. The linear actuators 78 and associated actuating members 80 are not shown in FIGS. 4A-4E.

FIG. 4A illustrates flow passage 66 in a closed condition, which is the free-state condition when pump 50 is not in operation. During operation, a controller such as controller 16, signals the linear actuator 78 that is coupled to tab 72a to exert a pulling force on tab 72a as indicated by arrow 86 in FIG. 4B. This causes portion 54 of body 52 to deform locally so that it pulls away from portion 56 of body 52 and creates a cavity 88a that is in fluid communication with inlet port 62, thereby opening flow passage 66 locally. This creates a vacuum and causes a packet 90a of fluid to be drawn, or sucked, into cavity 88a from the inlet port 62. During this initial operation, when a pulling force is exerted on tab 72a, a pushing force (indicated by flow arrows 92) is exerted on tabs 72b-72e such that the portions of flow passage 66 aligned with tabs 72b-72e remain closed.

Subsequently, the actuating device 76 sequentially deforms portion 54 of body 52, so that portion 54 is sequentially pulled away from portion 56 of body 52 locally, which causes the cavity 88a and the packet 90a of fluid within cavity 88a to propagate to the outlet port 64. Also, additional cavities 88 are created and propagated during this process. This is illustrated in FIGS. 4C-4E.

FIG. 4C illustrates pump 50 with a pulling force exerted on tab 72b, as indicated by arrow 86, and pushing forces exerted on tabs 72a and 72C-72E as indicated by arrows 92. As a result, cavity 88a and packet 90a of fluid contained therein are propagated toward the outlet port 64.

FIG. 4D illustrates pump 50 with pull forces exerted on tabs 72a and 72c as indicated by arrows 86 and push forces exerted on tabs 72b, 72d and 72e, as indicated by arrows 92. With pump 50 in this stage of operation, cavity 88a has propagated farther along flow passage 66 toward the outlet port 64 to a position that is generally aligned with tab 72c. Additionally, another cavity, identified as cavity 88b, is created proximate the inlet port 62 and communicates with inlet port 62, causing a packet 90b of fluid to be drawn into cavity 88b from inlet port 62.

FIG. 4E illustrates pump 50 with pulling forces exerted on tabs 72a, 72c and 72e, as indicated by arrows 86, and push forces exerted on tabs 72b and 72d, as indicated by arrows 92. In this stage of operation of pump 50, cavity 88a and the packet 90a of fluid contained therein, have propagated to outlet port 64, cavity 88b has propagated to a longitudinal position generally aligned with tab 72c and a third cavity, identified as cavity 88c, has been created proximate inlet port 62 and in fluid communication with inlet port 62, drawing a packet 90c of fluid into cavity 88c. An intermediate stage of the operation of pump 50, where cavity 88a and the packet 90a of fluid are aligned generally with tab 72d, has not been illustrated. After discharging from the outlet port 64 of pump 50, the fluid can flow through a tubing system, such as tubing 30 shown in FIG. 1, and into a patient intravenously.

FIGS. 5-8D illustrate a progressive cavity propagation pump 100 according to another embodiment of the present invention. Pump 100 includes a body 102 and the actuating device 76 shown in FIG. 5 and discussed previously with respect to pump 50. Body 102 includes an elastomeric member 103 and a frame 104 made of a thermoplastic material. An example of a suitable elastomeric material, for elastomeric member 103, is silicone and an example of a suitable thermoplastic material for frame 104 is a polycarbonate material.

Pump 100 also includes an inlet port 106 fluidically coupled to body 102 and an outlet port 108 that is also fluidicly coupled to body 102. A normally closed and substantially linear flow passage 110 extends between the inlet port 106 and the outlet port 108. The inlet port 106 and the outlet port 108 are fluidically uncoupled when pump 100 is in a free state condition, i.e., is not operating, wherein the pump body 102 is not deformed by the actuating device 76 discussed previously and shown in FIG. 5. As best seen in FIGS. 7B and 8A-8D, flow passage 110 is disposed laterally between the elastomeric member 103 and frame 104 of body 102.

As best seen in FIGS. 7A and 7B, frame 104 includes first 112 and second 114 laterally spaced flanges and a connecting member 116 that interconnects flanges 112 and 114. Flanges 112 and 114 and connecting member 116 can be integrally formed with one another. The connecting member 116 defines a cavity 118.

Flange 112 includes a plurality of longitudinally spaced tabs, identified as tabs 120a, 120b and 120c in FIGS. 8A-8D. The elastomeric member 103 includes first 124 and second 126 laterally spaced flanges and a central portion 128 integral with and disposed laterally between flanges 124 and 126. The central portion 128 extends away from flanges 124 and 126 and into cavity 118 of frame 104. Flange 124 of elastomeric member 103 is disposed in surrounding relationship with flange 112 of frame 104 and flange 126 is disposed in surrounding relationship with flange 114 of frame 104.

Flange 124 of elastomeric member 103 includes a plurality of longitudinally spaced tabs, identified as tabs 130a, 130b and 130c with each of the tabs 130 being disposed in surrounding relationship with a corresponding one of tabs 120 of frame 104. Pump 100 includes a plurality of apertures 132, that can be round holes, which extend through flange 126 of elastomeric member 103 and flange 114 of frame 104. Apertures 132 can be used, with conventional fasteners (not shown), to mount pump 100 to a stationary structure such as enclosure 14 shown in FIG. 1.

Pump 100 also includes a plurality of apertures 134, which can be round holes, that extend through flange 124 of elastomeric member 103 and flange 112 of frame 104. Each of the linear actuators 78 can be mechanically coupled to one of the tabs 120 of frame 104 and a corresponding one of the tabs 130 of elastomeric member 103 with one of the actuating members 80, which can be secured to tabs 102 using apertures 134 and conventional fasteners (not shown). Accordingly, actuating device 76 can be used to sequentially deform elastomeric member 103 and frame 104 as subsequently discussed in conjunction with FIGS. 8A-8D.

When pump 100 is not operating, flow passage 110 is closed as shown in FIG. 8A. During initial operation, one of the linear actuators 78 and the associated actuating member 80 exert a pulling force on tab 120a of frame 104 and tab 130a of elastomeric member 103 of body 102, as shown by arrow 136 in FIG. 8B. This causes body 102 to deform locally so that the central portion 128 of body 102 pulls away from the connecting member 116 of frame 104 locally in a position generally aligned with tabs 120a and 130. This deformation of elastomeric member 103 creates a cavity 138a that is in fluid communication with the inlet port 106 and is generally aligned with tabs 120a and 130a. As a result, a vacuum is created and a packet 140a of fluid is drawn into cavity 138a. During this stage of operation of pump 100, pushing forces are exerted of tabs 120b, 130b and 120c, 130c as indicated by arrows 142. Accordingly, flow passage 110 remains closed in the longitudinal positions aligned generally with tabs 120b, 130b and 120c, 130c.

FIG. 8C illustrates pump 100 with a pulling force exerted by actuating device 76 on tabs 120b and 130b, as indicated by arrow 136. Pushing forces are exerted by actuating device 76 on tabs 120a, 130a and 120c, 130c, as indicated by arrows 142. As a result, cavity 138a and the packet 140a of fluid contained within cavity 138a, are propagated toward outlet 108 to a position aligned generally with tabs 120b, 130b.

FIG. 8D illustrates pump 100 with pulling forces exerted on tabs 120a, 130a and 120c, 130c, as indicated by flow arrows 136 and a pushing force exerted on tabs 120b, 130b as indicated by arrow 142. As a result, cavity 138a and the packet 140a of fluid within cavity 138a have propagated to the outlet port 108 and a second cavity 138b is formed at a location proximate the inlet port 106 and in fluid communication with inlet port 106. A vacuum is created within cavity 138b, which causes a packet 140b of fluid to be drawn into cavity 138b from inlet port 106. After discharging from pump 50, the fluid can flow through a suitable section of tubing, such as tubing 30 in FIG. 1, to a catheter, such as catheter 34 in FIG. 1 inserted into a patient.

FIGS. 9-14 illustrate a progressive cavity propagation pump 150 according to another embodiment of the present invention. Pump 150 is similar to pumps 50 and 100 since the included flow passage 152 of pump 150, shown in FIGS. 11A-11D, is normally closed. However, pump 150 differs from pumps 50 and 100 since flow passage 152 extends along an arcuate path, whereas the flow passages 66 and 110 of pumps 50 and 100, respectively, extend along substantially linear paths.

The body 154 of pump 150 is made of an elastomeric material, such as silicone, and includes opposite exterior surfaces 156 and 158 and an edge surface 160 extending between surfaces 156 and 158 around the perimeter of body 154. The normally closed flow passage 152 is disposed within body 154 between opposite surfaces 156 and 158 and inward of edge surface 160. While edge surface 160 is cylindrical in the illustrated embodiment, it can have other shapes within the scope of the present invention. Body 154 includes an inner cylindrical surface 162 that defines a centrally disposed aperture 163 formed therein and extending through body 154. Body 154 also includes an inner portion 164 and an outer portion 166 and flow passage 152 is disposed between portions 164 and 166.

Pump 150 includes an inlet port 167 and an outlet port 168 that are coupled to body 154. The ports 167 and 168 can be integrally formed with body 154. As shown in FIGS. 11A-11D, ports 167 and 168 extend inwardly to the normally closed flow passage 152. The inner portion 164 and outer portion 166 are disposed in abutting relationship with one another along flow passage 152 when flow passage 152 is closed as shown in FIG. 11A. Accordingly, inlet port 167 and outlet port 168 are fluidicly uncoupled when flow passage 152 is closed. The inner portion 164 and the outer portion 166 are separable from one another along flow passage 152 to permit the creation of a cavity within flow passage 152 and the propagation of the cavity, and a packet of fluid contained therein, from the inlet port 167 to the outlet port 168 as illustrated and subsequently discussed in conjunction with FIGS. 11B-11D.

Pump 150 includes an actuating device 170 illustrated in FIGS. 9 and 12-14. FIG. 9 illustrates the body 154 of pump 150 and the actuating device 170 mounted to a stationary structure 172. The actuating device 170 is coupled to body 154 as subsequently discussed and is operable, during operation of pump 150, for sequentially deforming body 154 to create a cavity within the normally closed flow passage 152 thereby drawing a packet of fluid into the cavity from the inlet port 167 and propagating the cavity and the packet of fluid contained therein to the outlet port 168. This is subsequently described in conjunction with FIGS. 11A-11D.

As shown in FIGS. 9 and 12, the mount structure 172 includes first 174 and second 176 mount flanges and a plurality of connecting members 178 that extend between mount flanges 174 and 176. Flanges 174 and 176 and connecting members 178 can be secured to one another by a plurality of conventional fasteners such as bolts 180 shown in FIG. 9.

The actuating device 170 includes a motor 182, that can be an electric motor. Motor 182 includes an output shaft 184 that is rotatable about a longitudinal centerline axis 186. Motor 182 also includes a stationary housing 188 that is mounted to the mount structure 172, as shown in FIGS. 9 and 12, by a plurality of conventional fasteners (not shown).

The actuating device 170 also includes a coupling member 190 that is coupled to the output shaft 184 for rotation with shaft 184. A driven axle 192, which can be cylindrical, has a longitudinal centerline axis 194 and is mounted to coupling member 190. The driven axle 192 extends into, and can extend through, the aperture 163 formed in body 154. The longitudinal centerline axis 194 of driven axle 192 is offset from the longitudinal centerline axis 186 of the output shaft 184 of motor 182 by a distance 196 shown in FIG. 13. The driven axle 192 is stationary relative to coupling member 190 and does not rotate about longitudinal centerline axis 194. Driven axle 192 orbits about the longitudinal centerline axis 186 due to the offset 196 and since the longitudinal centerline axis 186 of output shaft 184 is also the longitudinal centerline axis of coupling member 190 when these parts are assembled.

Body 154 has a plurality of spaced apertures 200 formed therein and extending therethrough and can be mounted to the stationary mount structure 172 with a plurality of conventional fasteners, such as bolts 202 (best seen in FIG. 9), each extending through one of the apertures 200 into a threaded hole (not shown) formed in mount flange 176. Alternately, bolts 202 can extend through flange 176 and can be secured with conventional nuts (not shown).

The longitudinal centerline axis 186 of the output shaft 184 of motor 182 passes through aperture 163 formed in body 154 at a location substantially coincident with the center of aperture 163. Accordingly, the driven axle 192 is offset with respect to the cylindrical surface 162 and aperture 163 as shown in FIGS. 11B-11D and 14, due to the offset 196 between axes 186 and 194. The driven axle 192 has a diameter 204 shown in FIG. 14. The magnitude of diameter 204 can vary with the various embodiments of progressive cavity propagation pumps according to the present invention. The magnitude of offset 196 is selected, in conjunction with the magnitude of diameter 204, so that the driven axle 192 contacts the inner cylindrical surface 162 of body 154 and exerts a force on the inner portion 164 of body 154, thereby deforming the inner portion 164, as axle 192 orbits about the longitudinal centerline axis 186 of the output shaft 184 of motor 182. This causes the creation and propagation of a cavity in flow passage 152, as well as the propagation of a packet of fluid drawn into the cavity. The magnitude of offset 196 and the rotational speed of output shaft 184 affect the volumetric flow rate through passage 152.

FIG. 11A illustrates pump 150 in a free state, or non-operating condition. The flow passage 152 is closed and extends along a circular path between inlet port 167 and outlet port 168. During operation of pump 150, the driven axle 192 pushes the inner portion 164 outward as it orbits around centerline axis 186. At any given time, this outward compression of inner portion 164 pulls the inner portion 164 away from the outer portion 166 of body 154 at a location approximately 180° from the center of the outward deflection of inner portion 164 as shown in FIGS. 11B-11D. For purposes of illustration, the steady state position of the inner cylindrical surface 162 of body 154 is shown in dashed line in FIGS. 11B-11D, while the operating position is shown in solid line. Also, for purposes of illustration, surface 162 is shown to be cylindrical in FIGS. 11B-11D, although it may be appreciated that the shape of surface 162 may be deformed due to the action of driven axle 192.

FIG. 11B illustrates pump 150 with the driven axle 192 in a position that causes flow passage 152 to open locally and create a cavity 206 that is in fluid communication with the inlet port 167. This creates a vacuum that causes a packet 208 of fluid to be drawn into cavity 206 in flow passage 152 from the inlet port 167. FIG. 11C illustrates pump 150 with the driven axle 192 in a position that results in cavity 206 and the packet 208 of fluid in cavity 206 being propagated to a position approximately midway between the inlet port 167 and the outlet port 168. FIG. 11D illustrates pump 150 with the driven axle 192 in a position that results in cavity 206 and the packet 208 of fluid therein propagated to outlet port 168, in fluid communication with the outlet port 168.

FIGS. 15-18F illustrate a progressive cavity propagation pump 250 according to another embodiment of the present invention. As shown in FIG. 15, pump 250 includes a body 252 and the actuating device 170 discussed previously, with body 252 and actuating device 170 mounted to the stationary structure 172. Body 252 includes a plurality of spaced apertures 254 formed therein and extending therethrough. Body 252 can be mounted to the stationary mount structure 172 shown in FIG. 15 with a plurality of conventional fasteners, such as bolts 202, each extending through one of the apertures 254 and into a threaded hole in flange 176. Alternately, bolts 202 can extend through holes in flange 176 and be secured with conventional nuts (not shown).

Body 252 is made of an elastomeric material, such as silicone, and includes opposite exterior surfaces 256 and 258 and an edge surface 260 extending between surfaces 256 and 258 around the perimeter of body 252. Pump 250 further includes first 270 and second 272 normally closed flow passages disposed within body 252 between opposite exterior surfaces 256 and 258 and inward of edge surface 260. The flow passages 270, 272 extend along arcuate paths. In the illustrated embodiment, passages 270, 272 extend along paths that each describes a portion of a circle. First 274 and second 276 open conduits are also disposed within body 252 between opposite exterior surfaces 256 and 258 and inward of edge surface 260. Pump 250 includes an inlet port 278 and an outlet port 280, each coupled to body 252.

The normally closed flow passage 270 has a proximal end 282 disposed proximate inlet port 278 and a distal end 284 disposed proximate a proximal end 286 of the open conduit 276. Proximal end 282 can be disposed immediately adjacent input port 278 and distal end 284 of flow passage 270 can be disposed immediately adjacent proximal end 286 of conduit 276. The normally closed flow passage 272 has a proximal end 290 and a distal end 292 disposed proximate outlet port 280. The open conduit 274 has a proximal end 296 disposed proximate inlet port 278 and a distal end 298 disposed proximate the proximal end 290 of the normally closed flow passage 272. Proximal end 296 of conduit 274 can be immediately adjacent inlet port 278 and distal end 298 of conduit 274 can be disposed immediately adjacent the proximal end 290 of flow passage 272. The distal end 292 of flow passage 272 can be disposed immediately adjacent the outlet port 280.

Body 252 of pump 250 includes an inner cylindrical surface 300 that defines a centrally disposed aperture 301 formed therein and extending therethrough. The driven axle 192 of actuating device 170 extends into aperture 301, as shown in FIGS. 15 and 18A-18F, and can extend through aperture 301. Body 252 includes an inner portion 302 that exists between aperture 301 and flow passages 270 and 272. Body 252 also includes an outer portion 304 that exists between flow passages 270, 272 and edge surface 260 of body 252. Inner portion 302 and outer portion 304 are integral with one another intermediate the proximal end 282 of flow passage 270 and the distal end 292 of flow passage 272.

The operation of pump 250 can be further understood with reference to FIGS. 18A-18F. FIG. 18A illustrates pump 250 in a free state, or non-operating condition with flow passages 270 and 272 closed. The driven axle 192 is offset with respect to cylindrical surface 300 and aperture 301, i.e., it is not concentrically disposed with respect to surface 300 and aperture 301. The driven axle 192 exerts an outward pushing force on the inner portion 302 of body 252 during operation of pump 250 as the driven axle 192 orbits around the longitudinal centerline axis 186 of output shaft 184 of motor 182 of actuating device 170 shown in FIG. 13. At any given time, this outward compression of inner portion 302 pulls the inner portion 302 away from the outer portion 304 at a location approximately 180° from the center of the outward deflection of inner portion 302, except in those circumferential locations where neither of the passages 270, 272 exist, as shown in FIGS. 18B-18F. This opens one of the normally closed flow passages 270, 272, creating a cavity therein, while the other of flow passages 270, 272 remains closed. For purposes of illustration, the steady state position of the inner cylindrical surface 300 is shown in dashed line in FIGS. 18B-18F, while the operating position, caused by driven axle 192, is shown in solid line. Driven axle 192 is shown in a plurality of positions as it orbits around the centerline axis 186 of output shaft 184 as shown in FIGS. 18B-18F.

FIG. 18B illustrates the driven axle 192 in a position that causes the flow passage 270 to open locally and create a cavity 306 in flow passage 270 that is in fluid communication with inlet port 278. This creates a vacuum that causes a packet 308 of fluid to be drawn into cavity 306 in flow passage 270. As shown in FIG. 18B, flow passage 272 is closed at this stage of operation of pump 250. FIG. 18C illustrates pump 250 with the driven axle 192 in a position that results in cavity 306 and the packet 308 of fluid therein, being propagated to the distal end 284 of flow passage 270, in fluid communication with the open conduit 276. The fluid is then pumped through conduit 276 to outlet port 280 as shown in FIG. 18D.

FIG. 18E illustrates pump 250 with the driven axle 192 in a position that causes flow passage 272 to open locally and create a cavity 310 that is in fluid communication with the distal end 298 of the open conduit 274. Since conduit 274 is in fluid communication with inlet port 278, conduit 274 remains filled with the fluid (not shown in FIG. 18E due to the position of conduit 274 that is shown in dashed line) that is supplied to inlet port 278. The creation of cavity 310 in flow passage 272 creates a vacuum that causes a packet 312 of fluid to be drawn into cavity 310. As shown in FIG. 18E, flow passage 270 is closed at this stage of operation of pump 250.

FIG. 18F illustrates pump 250 with the driven axle 192 in a position that causes the cavity 310 and the packet 312 of fluid therein to be propagated to the distal end 292 of flow passage 274 and through outlet port 280.

As may be appreciated with reference to FIGS. 18B-18F, during a first portion of any revolution of driven axle 192 about centerline axis 186, cavity 306 is created and cavity 306 and the packet 308 of fluid therein are propagated to the outlet port 280. During a second portion of any revolution of driven axle 192 about axis 186, cavity 310 is created and cavity 310 and the packet 312 of fluid therein are propagated to the outlet port 280. Accordingly, during one complete revolution of driven axle 192 about axis 186, two packets of fluid are propagated to the outlet port. As a result pump 250 has twice the output of a pump configured as pump 150 discussed previously, if the pumps are otherwise the same, i.e., the speed of rotation of output shaft 184 of motor 182, and other parameters, are the same.

FIGS. 19-23D illustrate a progressive cavity propagation pump 350 according to another embodiment of the present invention. Pump 350 includes a body 352 and actuating device 170 discussed previously, each mounted to a stationary structure, such as structure 172 as shown in FIG. 19. Body 352 includes a plurality of spaced apertures 354 formed therein and can be mounted to the stationary mount structure 172 shown in FIG. 19 with a plurality of conventional fasteners, such as bolts 202, that pass through apertures 354 into mating apertures (not shown) in mount flange 176.

Body 352 includes an outer frame 356 made of a thermoplastic material and an elastomeric member 358, made of an elastomeric material that can be silicone, overmolded onto the outer frame 356 as best seen in FIG. 22 and further understood with reference to FIGS. 20 and 21. Body 352 further includes an inner frame 360 made of a thermoplastic material that engages the elastomeric member 358. The outer frame 356 and inner frame 360 can be made of the same, or different, thermoplastic materials. An example of a suitable thermoplastic material for frames 356 and 360 is a polycarbonate material.

The outer frame 356 includes an annular outer flange 362 and an inner hub 364 (shown in FIGS. 22 and 23A-23D) that is connected to the outer flange 362. An annular gap exists between flange 362 and hub 364, except at locations where flange 362 and hub 364 are connected by a plurality of circumferentially spaced struts 366. Hub 364 includes an inner cylindrical surface 368. Pump 350 further includes an inlet port 370 and an outlet port 372. Ports 370, 372 are coupled to body 352 of pump 350 and extend through the inner cylindrical surface 368 of hub 364 of outer frame 356.

As best seen in FIG. 21, the elastomeric member 358 includes an inner hub 374 that defines a centrally disposed aperture 376 that extends through the elastomeric member

358. The elastomeric member 358 further includes a plurality of circumferentially spaced spokes 378 that extend radially outwardly from hub 374 to a rim 380. The hub 374, spokes 378 and rim 380 define a plurality of circumferentially spaced cavities 382. The elastomeric member 358 further includes an outer portion 384 that is integral with rim 380. The rim 380 includes an inner cylindrical surface 386 that has a diameter 388 as shown in FIG. 22.

The inner frame 360 includes a plurality of circumferentially spaced engaging members 390 that have a shape that is complimentary with the shape of the circumferentially spaced cavities 382 of elastomeric member 358, as may be appreciated by a comparison of the shape of cavities 382 shown in FIG. 21 and the shape of the engaging members 390 shown in FIGS. 23A-23D. The engaging members 390 of inner frame 360 define a discontinuous cylindrical surface 392 having a diameter 394, as shown in FIG. 21. The diameter 394 of inner frame 360 is greater than the diameter 388 (shown in FIG. 22) of the rim 380 of elastomeric member 358. Accordingly, the inner frame 360 engages the inner cylindrical surface 386 of the elastomeric member 358 in an interference fit. The inner frame 360 further includes an inner cylindrical surface 396 that defines a centrally disposed aperture 397, with aperture 397 extending through inner frame 360 and being effective for receiving the driven shaft 192 of the actuating device 170.

Pump 350 further includes a normally closed flow passage 400 (as seen in FIGS. 23A-23D), that is disposed between the inner cylindrical surface 368 of outer frame 356 and the elastomeric member 358 and extends along an arcuate path between the inlet port 370 and the outlet port 372. In the illustrative embodiment, the arcuate path is a circular path. The inlet port 370 and the outlet port 372 extend through the inner cylindrical surface 368 of outer frame 356.

The operation of pump 350 can be further understood with reference to FIGS. 23A-23D. FIG. 23A illustrates pump 350 in a free state, or non-operating condition with flow passage 400 closed. The driven axle 192 is offset with respect to the inner cylindrical surface 396 and aperture 397 formed in the inner frame 360, i.e., it is not concentrically disposed with respect to surface 396 and aperture 397. The driven axle 192 exerts an outward pushing force on the inner frame 360 during operation of pump 350 as the driven axle 192 orbits around the longitudinal centerline axis 186 of output shaft 184 of motor 182 of actuating device 170 shown in FIG. 13. At any given time, this outward force acting on inner frame 360 pushes the elastomeric member 358 outward so as to locally compress elastomeric member 358. This results in elastomeric member 358 being pulled away from the inner cylindrical surface 368 of outer frame 356 at a location approximately 180 degrees from the center of the outward deflection of the elastomeric member 358. This opens flow passage 400 locally, creating a cavity therein.

FIG. 23B illustrates the driven axle 192 in a position that causes the flow passage 400 to open locally and create a cavity 402 that is in fluid communication with the inlet port 370. This creates a vacuum that causes a packet 404 of fluid to be drawn into cavity 402 in flow passage 400. In FIGS. 23B-23D, the steady state position of the inner cylindrical surface 396 of inner frame 360 is shown in dashed line, while the operating position, caused by driven axle 192, is shown in solid line. FIG. 23C illustrates pump 350 with the driven axle 192 in a position that results in cavity 402 and the packet 404 of fluid therein, being propagated to a position approximately midway between the inlet port 370 and the outlet port 372. FIG. 23D illustrates pump 350 with the driven axle 192 in a position that results in cavity 402 and the packet 404 of fluid therein, being propagated to the outlet port 372, with the cavity 402 and the packet 404 of fluid in fluid communication with the outlet port 372.

FIGS. 24-27D illustrate a progressive cavity propagation pump 450 according to another embodiment of the present invention. Pump 450 includes a pump body 452 and actuating device 170 discussed previously, each mounted to a stationary structure, for example structure 172 shown in FIG. 24. The body 452 of pump 450 includes a plurality of spaced apertures 454 formed therein and can be mounted to the stationary mount structure 172 with a plurality of conventional fasteners, such as bolts 202, that pass through apertures 454 into mating apertures (not shown) in mount flange 176 of structure 172.

Body 452 includes an outer frame 456 and an inner frame 458. Frames 456 and 458 are made of a thermoplastic material, and an example of a suitable thermoplastic material is a polycarbonate material. The body 452 further includes an elastomeric member 460 that is overmolded onto the outer frame 456 and inner frame 458. An example of a suitable material for the elastomeric member 460 is silicone.

The outer frame 456 includes an annular flange 462 that is adapted to be mounted to a stationary structure, such as structure 172 shown in FIG. 24. As shown in FIG. 26, the apertures 454 of body 452 are formed in the annular flange 462 of outer frame 456. The outer frame 456 further includes an inner hub 464 connected to the outer flange 462. The inner hub 464 includes an inner cylindrical surface 466.

The inner frame 458 includes an annular flange 468 and a hub 470 having an inner cylindrical surface 472 that defines a centrally disposed aperture 474 formed in inner frame 458. The aperture 474 receives the driven axle 192 of the actuating device 170. Flange 468 of inner frame 458 includes a plurality of circumferentially spaced apertures 476 formed therein that have a substantially smaller diameter than aperture 474.

During the overmolding process, portions of the elastomeric member 460 extend into apertures 476, which helps to secure the elastomeric member 460 to inner frame 458. The elastomeric member 460 also includes a centrally disposed aperture 478 formed therein, defined by a cylindrical surface 480.

The elastomeric member 460 is disposed radially between the inner frame 458 and the outer frame 456. More particularly, the elastomeric member 460 is disposed radially between the annular flange 468 of the inner frame 458 and the inner cylindrical surface 466 of the inner hub 464 of outer frame 456.

Pump 450 includes a normally closed flow passage 490, shown in FIGS. 27A-27D, that is disposed between the elastomeric member 460 and the inner cylindrical surface 466 of the inner hub 464 of the outer frame 456. Pump 450 further includes an inlet port 492 and an outlet port 494, with each of the ports 492, 494 being coupled to the body 452 of pump 450. As shown in FIGS. 27A-27D, the normally closed flow passage 490 extends along an arcuate path, which is a circular path in the illustrated embodiment, between the inlet port 492 and the outlet port 494.

The operation of pump 450 can be further understood with reference to FIGS. 27A-27D. FIG. 27A illustrates pump 450 in a free state, or non-operating condition with flow passage 490 closed. The driven axle 192 is offset with respect to the inner cylindrical surface 472 of inner frame 458 and the aperture 474 formed in the inner frame 458, i.e., it is not concentrically disposed with respect to surface 472 and aperture 474, as shown in FIG. 24. The driven axle 192 exerts an outward pushing force on the inner frame 458 during operation of pump 450 as the driven axle 192 orbits around the longitudinal centerline axis 186 of output shaft 184 of motor 182 of actuating device 170 shown in FIG. 13. At any given time, this outward force acting on inner frame 458 pushes the elastomeric member 460 outward so as to locally compress the elastomeric member 460. This results in the elastomeric member 460 being pulled away from the inner cylindrical surface 466 of the outer frame 456 locally at a location approximately 180 degrees from the center of the radially outward deflection of the elastomeric member 460. This opens flow passage 490 locally, creating a cavity therein.

FIG. 27B illustrates the driven axle 192 in a position that causes the flow passage 490 to open locally and create a cavity 500 that is in fluid communication with the inlet port 492. This creates a vacuum that causes a packet 502 of fluid to be drawn into cavity 500 in flow passage 490. In FIGS. 27B-27D, the steady state position of the inner cylindrical surface 472 of inner frame 458 is shown in dashed line, while the operating position, caused by driven axle 192, is shown in solid line. FIG. 27C illustrates pump 450 with the driven axle 192 in a position that results in cavity 500 and the packet 502 of fluid therein, being propagated to a position approximately midway between the inlet port 492 and the outlet port 494. FIG. 27D illustrates pump 450 with the driven axle 192 in a position that results in cavity 500 and the packet 502 of fluid therein, being propagated to the outlet port 494, with the cavity 500 and the packet 502 of fluid in fluid communication with the outlet port 494.

FIGS. 28-31D illustrate a progressive cavity propagation pump 550 according to another embodiment of the present invention. Pump 550 includes a pump body 552 and actuating device 170 discussed previously, each mounted to a stationary structure, for example structure 172 as shown in FIG. 28. The body 552 includes a plurality of spaced apertures 554 formed therein and can be mounted to the stationary mount structure 172 with a plurality of conventional fasteners, such as bolts 202, that pass through apertures 554 into mating apertures (not shown) in mount flange 176 of structure 172.

Body 552 includes a first sub-assembly, indicated generally at 556 (shown in FIG. 30), which includes an inner frame 558 made of a thermoplastic material and a first elastomeric member 560 that is overmolded onto the inner frame 558 as may be appreciated with reference to FIGS. 30 and 31A-31D. An example of a suitable thermoplastic material for the inner frame 558 is a polycarbonate material. An example of a suitable elastomeric material for the first elastomeric member 560 is silicone. The inner frame 558 includes a hub 562 having an inner cylindrical surface 564 that defines a centrally disposed aperture 565 that extends through frame 558. The inner frame 558 also includes an annular flange 566 that is integral with and radially outward of the hub 562. Flange 566 includes a plurality of circumferentially spaced apertures 568 formed therein. During the overmolding process, portions of the elastomeric member 560 extend through the holes 568, which helps secure the elastomeric member 560 to the inner frame 558. As may be appreciated with reference to FIG. 30, the diameter of holes 568 is significantly smaller than the diameter of the centrally disposed aperture 565 extending through frame 558.

The body 552 of pump 550 further includes a second sub-assembly, indicated generally at 570, that includes an outer frame 572 having a centrally disposed aperture 574 formed therein and extending therethrough, and further including the first assembly 556 discussed previously. The first sub-assembly 556 is disposed within the aperture 574 such that the first sub-assembly 556 is disposed in contacting engagement with the outer frame 572. More particularly, in the illustrated embodiment, an outer edge surface 576 of the first elastomeric member 560 is disposed in contacting engagement with an inner cylindrical surface 578 of outer frame 572 when the pump 550 in a free state or non-operating condition. Pump 550 includes a normally closed flow passage 580 (shown in FIGS. 31A-31D) which is disposed between edge surface 576 of elastomeric member 560 and the inner cylindrical surface 578 of outer frame 572.

Pump 550 further includes an inlet port 582 and an outlet port 584, with each of the ports 582, 584 being coupled to the body 552 of pump 550. As shown in FIGS. 31A-31D, the normally closed flow passage 580 extends along an arcuate path, which is a circular path in the illustrated embodiment, between the inlet port 582 and the outlet port 584.

The body 552 of pump 550 further includes a second elastomeric member 590 that is overmolded onto the second sub-assembly 570, as may be appreciated with reference to FIGS. 28, 29 and 31A-31D. An example of a suitable material for the second elastomeric member 590 is silicone. The second elastomeric member 590 prevents fluid from leaking from the normally closed flow passage 580 exterior of the body 552 of pump 550. As best seen in FIG. 30, the outer frame 572 includes a plurality of circumferentially spaced apertures 592 which are disposed radially outward of aperture 574 and have a significantly smaller diameter than aperture 574. During the overmolding process, portions of the elastomeric member 590 extend into and through apertures 592 of outer frame 572. These portions of the second elastomeric member 590 are shaped as cylindrical posts 594. For purposes of illustration, these are shown in the exploded perspective view of FIG. 30 on elastomeric member 590, separate from outer frame 572. However, as may be appreciated, these posts 594 are not present until member 590 is overmolded onto 572 and they extend through apertures 592. The presence of posts 594 of elastomeric member 590 in the apertures 592 of outer frame 572, help secure the second elastomeric member 590 to the outer frame 572.

The operation of pump 550 can be further understood with reference to FIGS. 31A-31D. FIG. 31A illustrates pump 550 in a free state, or non-operating condition with flow passage 580 closed. The driven axle 192 is offset with respect to the inner cylindrical surface 564 and the aperture 565 formed in the inner frame 558, i.e., it is not concentrically disposed with respect to surface 564 and aperture 565, as shown in FIG. 28. The driven axle 192 exerts an outward pushing force on the inner cylindrical surface 564 of inner frame 558 during operation of pump 550 as the driven axle 192 orbits around the longitudinal centerline axis 186 of output shaft 184 of motor 182 of actuating device 170 shown in FIG. 13. At any given time, this outward force acting on inner frame 558 pushes the first elastomeric member 560 outward so as to locally compress the first elastomeric member 560. This results in the edge surface 576 of the first elastomeric member 560 being pulled away from the inner cylindrical surface 578 of outer frame 572 locally at a location approximately 180 degrees from the center of the outward deflection of the first elastomeric member 560. This opens flow passage 580 locally, creating a cavity therein.

FIG. 31B illustrates the driven axle 192 in a position that causes the flow passage 580 to open locally and create a cavity 596 that is in fluid communication with the inlet port 582. This creates a vacuum that causes a packet 598 of fluid to be drawn into cavity 596 in flow passage 580. In FIGS. 31B-31D, the steady state position of the inner cylindrical surface 564 formed in inner frame 558 is shown in dashed line, while the operating position, caused by driven axle 192, is shown in solid line. FIG. 31C illustrates pump 550 with the driven axle 192 in a position that results in cavity 596 and the packet 598 of fluid therein, being propagated to a position approximately midway between the inlet port 582 and the outlet port 584. FIG. 31D illustrates pump 550 with the driven axle 192 in a position that results in cavity 596 and the packet 598 of fluid therein, being propagated to the outlet port 584 with the cavity 596 and the packet of fluid 598 in fluid communication with the outlet port 584.

FIGS. 32-35C illustrate a progressive cavity propagation pump 650 according to another embodiment of the present invention. Pump 650 includes a body 652 and actuating device 170 discussed previously, each mounted to a stationary structure, for example structure 172 as shown in FIG. 32. Body 652 includes spaced apertures 654 in an outer frame 656, made of a thermoplastic material, having a channel 658 formed therein. Pump 650 further includes an inlet port 660 and an outlet port 662, with ports 660, 662 coupled to body 652. The inlet port 660 and outlet port 662 are in fluid communication with channel 658 and channel 658 extends along an arcuate path, which is a circular path in the illustrated embodiment, between the inlet port 660 and the outlet port 662.

Body 652 further includes an inner frame 670 made of a thermoplastic material. An example of a suitable material for inner frame 670 and outer frame 656 is a polycarbonate material. The inner frame 670 includes a base member 672 having a first surface 674 and a second, opposite surface 676, as shown in FIG. 35A. The inner frame 670 further includes a protruding portion 678 that is integral with base member 672. The protruding portion 678 extends away from surface 676 of base member 672 and is disposed within the channel 658 of the outer frame 656. The inner frame further includes a tower 680 that is integral with the base member 672 and extends away from surface 674 of base member 672. Tower 680 is hollow and includes an inner surface 682 that includes a first tapered portion 684 and a second, cylindrical portion 686 as shown in FIGS. 35A-35C. The cylindrical portion 686 receives the driven axle 192. As shown in FIG. 32, and with reference to FIG. 34, in the illustrated embodiment, the driven axle 192 passes through or extends through a centrally disposed aperture 688 formed in the outer frame 656 and into and through the hollow interior of tower 680, such that the axle 192 engages the cylindrical portion 686 of the inner surface 682 of tower 680. However, in another embodiment (not shown), the body 652 of pump 650 can be mounted to a stationary structure such as structure 172, and the motor 182 can be mounted to a second stationary structure, such that the driven axle 192 enters the tower 680 from a distal end, where the cylindrical portion 686 of the inner surface 682 exists, and may or may not pass through the remainder of the tower 680.

The body 652 of pump 650 further includes an elastomeric member 690 that is overmolded onto the inner frame 670 and the outer frame 656. Elastomeric member 690 can be an annular member defining a central aperture 692, as shown in FIG. 34. The inner frame 670 includes a first plurality of relatively smaller diameter apertures 694 formed in the base member 672 and a plurality of relatively larger diameter holes 696, also formed in base member 672. During the overmolding process, portions of the elastomeric member 690 enter into apertures 694 and 696, which help secure the elastomeric member 690 to the inner frame 670. Also, the apertures 696 pass through the protruding portion 678 of the inner frame 670, as shown in FIGS. 35A-35C, such that the elastomeric member 690 is disposed between the protruding portion 678 and the channel 658 formed in the outer frame 656.

The pump 650 includes a normally closed flow passage 700 disposed between the elastomeric member 690 and the channel 658 of the outer frame 656, and extends along an arcuate path, which is a circular path in the illustrated embodiment, between the inlet port 660 and the outlet port 662. As subsequently discussed, due to the action of the actuating device, the elastomeric member 670 and the protruding portion 678 can be pulled away from the channel 658 of the outer frame 656 locally, so as to create a cavity within flow passage 700 proximate the inlet port 660. This creates a vacuum that causes fluid to be drawn into the cavity. During the overmolding process, portions of the elastomeric member 690 also enter and extend through a plurality of apertures 701 formed in outer frame 656 outward of channel 658 as shown in FIGS. 35A-35C. This helps secure the elastomeric member 690 to the outer frame 656 and seals the flow passage 700 so fluid doesn't leak exterior of pump 650.

The operation of pump 650 can be further understood with reference to FIGS. 35A-35C. FIG. 35A illustrates pump 650 in a free state, or non-operating condition with flow passage 700 closed. The driven axle 192 is offset with respect to the cylindrical portion 686 of the inner surface 682 of tower 680 as shown in FIGS. 32 and 35B-35C. The driven axle 192 exerts an outward pushing force on the cylindrical surface 686 of tower 680 during operation of pump 650 as the driven axle 192 orbits around the longitudinal centerline axis 186 of output shaft 184 of motor 182 of actuating device 170 shown in FIG. 13. Tower 680 is cantilevered from base member 672. Accordingly, the force exerted by driven axle 192 on the cylindrical surface 686 creates a moment which causes the protruding portion 678 of base member 672 and the corresponding portion of the elastomeric member 690 that at least partially surrounds the protruding portion 678, to pull away from the channel 658 formed in the outer frame 656 locally. This opens flow passage 700 locally, creating a cavity therein. During operation of pump 650, the protruding portion 678 and the corresponding portion of elastomeric member 690 wobble within channel 658, such that the cavity created in flow passage 700, and the fluid therein, are propagated from the inlet port 660 to the outlet port 662.

FIG. 35B illustrates the driven axle 192 in a position that causes the flow passage 700 to open locally and create a cavity 702 that is in fluid communication with the inlet port 672. This creates a vacuum that causes a packet 704 of fluid to be drawn into cavity 702 of flow passage 700. For purposes of illustration, in FIGS. 35B-35C, the driven axle 192 is shown in dashed line. FIG. 35C illustrates pump 650 with the driven axle 192 in a position that results in cavity 702 and the packet 704 of fluid therein, being propagated to the outlet port 662, with the cavity 702 and the packet 704 of fluid in fluid communication with the outlet port 662.

While the foregoing description has set forth various embodiments of the present invention in particular detail, it must be understood that numerous modifications, substitutions and changes can be undertaken without departing from the true spirit and scope of the present invention as defined by the ensuing claims. The invention is therefore not limited to specific embodiments as described, but is only limited as defined by the following claims.

What is claimed is:

1. A progressive cavity propagation pump comprising:
   a body made at least partially of an elastomeric material, the body adapted to be mounted to a stationary structure and including a centrally disposed aperture formed therein;
   an inlet port and an outlet port, each port being coupled to the body;
   a flow passage formed in the body and extending along a circular path between the inlet port and the outlet port, a pair of confronting, normally contacting portions of the body defining a normally closed portion of the flow passage, the normally closed portion of the flow passage having a first end coupled to the inlet port and a second end coupled to the outlet port, the body being sequentially deformable so as to (a) selectively separate the confronting body portions along the normally closed portion of the flow passage whereby to selectively open a cavity at the first end of the normally closed portion of the flow passage, and (b) selectively separate the confronting body portions ahead of the cavity and re-close the confronting body portions behind the cavity to thereby propagate the cavity therealong toward the second end of the normally closed portion of the flow passage, the inlet port being fluidicly uncoupled with the outlet port when the pump is in a free state condition; and an actuating device coupled to the body, the actuating device including a driven axle disposed within the aperture of the body and operable to orbit in a circular motion to sequentially deform the body and create and propagate the cavity so as to draw a packet of fluid from the inlet port and propagate the packet of fluid toward the outlet port.

2. A progressive cavity propagation pump as recited in claim 1, wherein:

the confronting, normally contacting portions of the body being first and second longitudinally extending elastomeric portions of the body and defining the flow passage as normally closed and extending from the inlet port to the outlet port, the first and second portions of the body being disposed in abutting relationship with one another when the flow passage is closed and being locally separable from one another during operation of the pump to create and propagate the cavity.

3. A progressive cavity propagation pump as recited in claim 2, wherein:

one of the first and second body portions is adapted to be mounted to a stationary structure;

the actuating device is coupled to the other of the first and second portions of the body.

4. A progressive cavity propagation pump as recited in claim 1, wherein:

the driven axle includes a first longitudinal centerline axis;

the actuating device further includes a motor having an output shaft that is rotatable about a second longitudinal centerline axis;

the output shaft is coupled to the driven axle and the second longitudinal centerline axis is offset relative to the first longitudinal centerline axis, wherein the driven axle orbits around the second longitudinal centerline axis during operation of the pump thereby creating the cavity and propagating the cavity and the packet of fluid therein to the outlet port.

5. A progressive cavity propagation pump as recited in claim 4, wherein:

the actuating device further comprises a coupling member coupled to the output shaft for rotation therewith; and the driven axle is mounted to the coupling member and is stationary relative to the coupling member.

6. A progressive cavity propagation pump as recited in claim 1, wherein:

the body includes a first sub-assembly comprising an inner frame made of a thermoplastic material and a first elastomeric member overmolded onto the inner frame.

7. A progressive cavity propagation pump as recited in claim 6, wherein:

the body further includes a second sub-assembly comprising an outer frame having a centrally disposed aperture formed therein and extending therethrough, the second sub-assembly further comprising the first sub-assembly, wherein the first sub-assembly is disposed within the aperture formed in the outer frame and is in contacting engagement with the outer frame;

the flow passage is normally closed and extends between the first elastomeric member and the outer frame along an arcuate path between the inlet port and the outlet port.

8. A progressive cavity propagation pump as recited in claim 7, wherein:

the body further includes a second elastomeric member overmolded onto the second sub-assembly; wherein the second elastomeric member prevents fluid from leaking from the normally closed flow passage exterior of the body of the pump.

9. A progressive cavity propagation pump as recited in claim 8, wherein:

the outer frame includes a plurality of relatively smaller apertures disposed outward of the centrally disposed aperture;

the second elastomeric member extends into the plurality of relatively smaller apertures.

10. A progressive cavity propagation pump as recited in claim 7, wherein:

the inner frame includes a centrally disposed aperture extending therethrough;

the actuating device including the driven axle disposed within the aperture of the inner frame;

the driven axle orbits in a circular motion that is offset relative to the aperture of the inner frame and the driven axle is in contacting engagement with the inner frame during operation of the pump wherein the first elastomeric member is pulled away from the outer frame at a position proximate the inlet port creating the cavity and drawing the packet of fluid from the inlet port into the cavity, and wherein the cavity and the packet of fluid contained therein are propagated along a circular path to the outlet port.

11. A progressive cavity propagation pump comprising:

a body made at least partially of an elastomeric material;

an inlet port and an outlet port, each port being coupled to the body;

a flow passage formed in the body and extending between the inlet port and the outlet port, at least a portion of the flow passage being normally closed, the inlet port being fluidicly uncoupled with the outlet port when the pump is in a free state condition; and an actuating device coupled to the body, the actuating device operable for sequentially deforming the body to create a cavity within the normally closed portion of the flow passage, the cavity being in fluid communication with the inlet port, thereby drawing a packet of fluid from the inlet port into the cavity and propagating the cavity and the packet of fluid contained therein toward the outlet port, wherein the body comprises:

a frame made of a thermoplastic material; and an elastomeric member overmolded onto the frame, the flow passage being formed between the thermoplastic frame and the elastomeric member.

12. A progressive cavity propagation pump as recited in claim 11, wherein:

the flow passage is normally closed, is disposed laterally between the frame and the elastomeric member and extends along a substantially linear path from the inlet port to the outlet port; and the actuating device is coupled to the frame and the elastomeric member and is operably effective for sequentially pulling the elastomeric member away from the frame at a plurality of longitudinally spaced locations, wherein the cavity is created and the cavity and the packet of fluid therein are propagated to the outlet port.

13. A progressive cavity propagation pump as recited in claim 11, wherein:
the frame includes first and second laterally spaced flanges and a connecting member interconnecting the first and second flanges and defining a cavity.

14. A progressive cavity propagation pump as recited in claim 13, wherein:
the elastomeric member includes first and second laterally spaced flanges and a central portion disposed laterally between the first and second flanges of the elastomeric member and extending away from the first and second flanges of the elastomeric member, the central portion being integral with the first and second portions of the elastomeric member;
the first flange of the elastomeric member is disposed in surrounding relationship with the first flange of the frame, the second flange of the elastomeric member is disposed in surrounding relationship with the second flange of the frame and the central portion of the elastomeric member extends into the cavity defined by the connecting member of the frame.

15. A progressive cavity propagation pump as recited in claim 13, wherein:
the first flange of the frame comprises a plurality of longitudinally spaced tabs;
the first flange of the elastomeric member comprises a plurality of longitudinally spaced tabs, each of the tabs of the elastomeric member disposed in surrounding relationship with one of the tabs of the frame;
the actuating device comprises a plurality of linear actuators, each being coupled to one of the tabs of the frame and a corresponding one of the tabs of the body, the linear actuators being operable for locally deforming the elastomeric member wherein the flow passage is open locally.

16. A progressive cavity propagation pump as recited in claim 11, wherein:
the frame comprises an outer frame made of a first thermoplastic material, the elastomeric member being overmolded onto the outer frame;
the frame further comprises an inner frame made of a second thermoplastic material, the inner frame engaging the elastomeric member.

17. A progressive cavity propagation pump as recited in claim 16, wherein:
the flow passage is normally closed, is disposed between the elastomeric member and the outer frame and extends along an arcuate path between the inlet port and the outlet port.

18. A progressive cavity propagation pump as recited in claim 17, wherein:
the arcuate path is a circular path.

19. A progressive cavity propagation pump as recited in claim 16, wherein:
the outer frame includes an outer flange adapted to be mounted to a stationary structure and an inner hub connected to the outer flange, the inner hub including an inner cylindrical surface;
the flow passage is normally closed and extends between the inner cylindrical surface of the inner hub of the outer frame and the elastomeric member along an arcuate path between the inlet and outlet ports.

20. A progressive cavity propagation pump as recited in claim 19, wherein:
the inlet port and the outlet port are coupled to the outer frame and extend through the inner cylindrical surface of the inner hub of the outer frame.

21. A progressive cavity propagation pump as recited in claim 17, wherein:
the elastomeric member includes an inner hub defining a centrally disposed aperture extending through the elastomeric member;
the elastomeric member further includes a rim and a plurality of circumferentially spaced spokes that extend between the hub and the rim;
the hub, spokes and rim define a plurality of circumferentially spaced cavities having a first shape;
the inner frame includes a plurality of circumferentially spaced engaging members having a second shape that is complimentary with the first shape of the cavities, wherein each of the engaging members is disposed in one of the cavities.

22. A progressive cavity propagation pump as recited in claim 21, wherein:
the engaging members of the inner frame define a discontinuous cylindrical surface having a first diameter;
the rim includes a discontinuous inner surface having a second diameter;
the first diameter is greater than the second diameter.

23. A progressive cavity propagation pump as recited in claim 16, wherein:
the flow passage is normally closed, is disposed between the elastomeric member and the outer frame and extends along an arcuate path between the inlet port and the outlet port;
the inner frame includes a centrally disposed aperture formed therein;
the actuating device includes a driven axle disposed within the aperture of the inner frame;
the driven axle orbits in a circular motion that is offset relative to the aperture of the inner frame and the driven axle is in contacting engagement with the inner frame during operation of the pump, wherein the elastomeric member is pulled away from the outer frame at a position proximate the inlet port creating the cavity and drawing the packet of fluid from the inlet port into the cavity, and wherein the cavity and the packet of fluid contained therein are propagated along a circular path to the outlet port.

24. A progressive cavity propagation pump as recited in claim 11, wherein:
the frame comprises an outer frame made of a first thermoplastic material and an inner frame made of a second thermoplastic material, the outer frame disposed in surrounding relationship with the inner frame;
the elastomeric member overmolded onto the outer frame and the inner frame.

25. A progressive cavity propagation pump as recited in claim 24, wherein:
the elastomeric member is disposed between the inner frame and the outer frame; and
the flow passage is normally closed, is disposed between the elastomeric member and the outer frame and extends along an arcuate path between the inlet port and the outlet port.

26. A progressive cavity propagation pump as recited in claim 24, wherein:
the outer frame includes an annular outer flange adapted to be mounted to a stationary structure and an inner hub connected to the annular outer flange, the inner hub including an inner cylindrical surface;

the flow passage is normally closed and extends between the elastomeric member and the inner cylindrical surface of the hub of the outer frame along an arcuate path between the inlet and outlet ports.

27. A progressive cavity propagation pump as recited in claim 24, wherein:

the flow passage is normally closed, is disposed between the elastomeric member and the outer frame and extends along an arcuate path between the inlet port and the outlet port;

the inner frame includes a centrally disposed aperture formed therein;

the actuating device includes a driven axle disposed within the aperture of the inner frame;

the driven axle orbits in a circular motion that is offset relative to the aperture of the inner frame and the driven axle is in contacting engagement with the inner frame during operation of the pump wherein the elastomeric member is pulled away from the outer frame at a position proximate the inlet port creating the cavity and drawing the packet of fluid from the inlet port into the cavity, and wherein the cavity and the packet of fluid contained therein are propagated along a circular path to the outlet port.

28. A progressive cavity propagation pump as recited in claim 24, wherein:

the outer frame includes an annular flange adapted to be mounted to a stationary structure and an inner hub connected to the annular outer flange, the inner hub including an inner cylindrical surface;

the inner frame includes an annular flange;

the elastomeric member is disposed between the annular flange of the inner frame and the inner cylindrical surface of the inner hub of the outer frame;

the flow passage is normally closed and extends between the elastomeric member and the inner cylindrical surface of the inner hub of the outer frame along an arcuate path between the inlet and outlet ports.

29. A progressive cavity propagation pump as recited in claim 28, wherein:

the annular flange of the inner frame includes a plurality of apertures formed therein and extending therethrough;

the elastomeric member extends into at least some of the plurality of apertures of the annular flange of the inner frame.

30. A progressive cavity propagation pump as recited in claim 11, wherein the frame comprises:

an outer frame made of a first thermoplastic material, the outer frame having a channel formed therein, the inlet port and the outlet port being in fluid communication with the channel, the channel extending along a circular path between the inlet port and the outlet port;

an inner frame made of a second thermoplastic material, the inner frame including a base member, a tower integral with the base member and extending longitudinally away from the base member and a protruding portion integral with and extending away from the base member, the protruding portion being disposed within the channel of the outer frame; wherein the elastomeric member overmolded onto the inner and outer frames, wherein the elastomeric member is disposed between the protruding portion of the inner frame and the channel of the outer frame; wherein the flow passage is normally closed, is disposed between the elastomeric member and the channel of the outer frame and extends along a circular path between the inlet port and the outlet port.

31. A progressive cavity propagation pump as recited in claim 30, wherein:

the tower is hollow and includes an inner surface;

the actuating device includes a driven axle extending into the tower and engaging the inner surface of the tower;

the engagement of the driven axle with the inner surface of the tower during operation of the pump causes the protruding portion to wobble within the channel of the outer frame and causes the elastomeric member disposed between the protruding portion and the channel to pull away from the channel, wherein the cavity is created and the cavity and the packet of fluid contained therein are propagated to the outlet port.

32. A progressive cavity propagation pump as recited in claim 31, wherein:

the inner surface of the tower includes a cylindrical portion receiving the driven axle.

33. A progressive cavity propagation pump as recited in claim 32, wherein:

the inner surface of the tower further includes a tapered portion extending away from the cylindrical portion.

34. A progressive cavity propagation pump as recited in claim 30, wherein:

the base member includes first and second surfaces, the tower extending away from the first surface and the protruding portion extending away from the second surface.

35. A progressive cavity propagation pump as recited in claim 30, wherein:

the base member of the inner frame includes a plurality of apertures formed therein;

the elastomeric member extends into at least a portion of the apertures.

36. A progressive cavity propagation pump as recited in claim 31, wherein:

the elastomeric member is an annular member defining a central aperture;

the driven axle extends through the central aperture of the elastomeric member and into the tower of the inner frame.

37. A progressive cavity propagation pump comprising:

a body made at least partially of an elastomeric material and including a pair of confronting portions;

an inlet port and an outlet port, each port being coupled to the body;

a flow passage formed in the body and extending between the inlet port and the outlet port, the pair of confronting portions of the body defining a normally closed portion of the flow passage, the inlet port being fluidicly uncoupled with the outlet port when the pump is in a free state condition;

an actuating device coupled to the body, the actuating device operable for sequentially deforming the body to create a cavity within the normally closed portion of the flow passage, the cavity being in fluid communication with the inlet port, thereby drawing a packet of fluid from the inlet port into the cavity and propagating the cavity and the packet of fluid contained therein toward the outlet port;

a first open conduit disposed within the body between the pair of confronting portions of the body, the first open conduit having proximal and distal ends; wherein the flow passage comprises a first normally closed flow passage having a proximal end disposed proximate the inlet port and a distal end disposed proximate the proximal end of the first open conduit;

the distal end of the first open conduit is disposed proximate the outlet port.

38. A progressive cavity propagation pump as recited in claim 37, further comprising:

a second normally closed flow passage having a proximal end and a distal end, the distal end being disposed proximate the outlet port;

a second open conduit disposed within the body and having a proximal end and a distal end, the proximal end of the second open conduit being disposed proximate the inlet port and the distal end being disposed proximate the proximal end of the second normally closed flow passage.

39. A progressive cavity propagation pump as recited in claim 38, wherein:

the body is adapted to be mounted to a stationary structure, the body including a centrally disposed aperture formed therein;

the actuating device includes a driven axle disposed within the aperture;

the cavity comprises a first cavity disposed within the first normally closed flow passage;

the driven axle orbits in a circular motion that is offset relative to the aperture during operation of the pump, wherein during a first portion of any revolution of the driven axle the first cavity is created and propagated, with the packet of fluid contained therein to the outlet port, and wherein during a second portion of any revolution of the driven axle a second cavity is created within the second normally closed flow passage, drawing a second packet of fluid into the second cavity, and the second cavity and the second packet of fluid contained therein are propagated, to the outlet port.

40. The progressive cavity propagation pump as recited in claim 38, wherein:

the first and second normally closed flow passages extend along arcuate paths.

41. A progressive cavity propagation pump as recited in claim 38, wherein:

the first and second normally closed flow passages each extend along a path describing a portion of a circle.

42. A progressive cavity propagation pump comprising:

a body made at least partially of an elastomeric material, the body adapted to be mounted to a stationary structure and including a centrally disposed aperture formed therein;

an inlet port and an outlet port, each port being coupled to the body;

a flow passage formed in the body and extending along a circular path between the inlet port and the outlet port, a pair of confronting, normally contacting portions of the body defining a normally closed portion of the flow passage, the normally closed portion of the flow passage having a first end coupled to the inlet port and a second end coupled to the outlet port, the body being sequentially deformable so as to (a) selectively separate the confronting body portions along the normally closed portion of the flow passage whereby to selectively open a cavity at the first end of the normally closed portion of the flow passage, and (b) selectively separate the confronting body portions ahead of the cavity and re-close the confronting body portions behind the cavity to thereby propagate the cavity therealong toward the second end of the normally closed portion of the flow passage, the inlet port being fluidicly uncoupled with the outlet port when the pump is in a free state condition; and means for sequentially deforming the body and including a driven axle disposed within the aperture of the body and operable to orbit in a circular motion to create and propagate the cavity so as to draw a packet of fluid from the inlet port and propagate the fluid packet toward the outlet port.

43. A progressive cavity propagation pump as recited in claim 42, wherein:

the confronting, normally contacting portions of the body being first and second longitudinally extending elastomeric portions of the body and defining the flow passage as normally closed and extending from the inlet port to the outlet port, the first and second portions of the body being disposed in abutting relationship with one another when the flow passage is closed and being locally separable from one another during operation of the pump to create and propagate the cavity to the outlet port.

44. A progressive cavity propagation pump as recited in claim 43, wherein:

one of the first and second body portions is adapted to be mounted to a stationary structure;

the means for sequentially deforming the body is coupled to the other of the first and second portions of the body.

45. A progressive cavity propagation pump as recited in claim 42, wherein:

the driven axle includes a first longitudinal centerline axis;

the means for sequentially deforming the body further includes a motor having an output shaft that is rotatable about a second longitudinal centerline axis;

the output shaft is coupled to the driven axle and the second longitudinal centerline axis is offset relative to the first longitudinal centerline axis, wherein the driven axle orbits around the second longitudinal centerline axis during operation of the pump thereby creating the cavity and propagating the cavity and the packet of fluid therein to the outlet port.

46. A progressive cavity propagation pump as recited in claim 42, wherein:

the body includes a first sub-assembly comprising an inner frame made of a thermoplastic material and a first elastomeric material overmolded onto the inner frame.

47. A progressive cavity propagation pump as recited in claim 46, wherein:

the body further includes a second sub-assembly comprising an outer frame having a centrally disposed aperture formed therein and extending therethrough, the second sub-assembly further comprising the first sub-assembly, wherein the first sub-assembly is disposed within the aperture formed in the outer frame and is in contacting engagement with the outer frame;

the flow passage is normally closed and extends between the first elastomeric member and the outer frame along an arcuate path between the inlet port and the outlet port.

48. A progressive cavity propagation pump as recited in claim 47, wherein:

the body further includes a second elastomeric member overmolded onto the second sub-assembly; wherein the second elastomeric member prevents fluid from leaking from the normally closed flow passage exterior of the body of the pump.

49. A progressive cavity propagation pump as recited in claim 47, wherein:

the inner frame includes a centrally disposed aperture formed therein and extending therethrough;

the means for sequentially deforming the body including the driven axle disposed within the aperture of the inner frame;

the driven axle orbits in a circular motion that is offset relative to the aperture of the inner frame and the driven axle is in contacting engagement with the inner frame during operation of the pump wherein the first elastomeric member is pulled away from the outer frame at a position proximate the inlet port creating the cavity and drawing the packet of fluid from the inlet port into the cavity, and wherein the cavity and the packet of fluid contained therein are propagated along a circular path to the outlet port.

50. A progressive cavity propagation pump comprising:

a body made at least partially of an elastomeric material;

an inlet port and an outlet port, each port being coupled to the body;

a flow passage formed in the body and extending between the inlet port and the outlet port, at least a portion of the flow passage being normally closed, the inlet port being fluidicly uncoupled with the outlet port when the pump is in a free state condition;

means for sequentially deforming the body to create a cavity within the normally closed portion of the flow passage, the cavity being in fluid communication with the inlet port, thereby drawing a packet of fluid from the inlet port into the cavity and propagating the cavity and the fluid packet contained therein toward the outlet port, wherein the body comprises:

a frame made of a thermoplastic material; and an elastomeric member overmolded onto the frame, the flow passage being formed between the thermoplastic frame and the elastomeric member.

51. A progressive cavity propagation pump as recited in claim 50, wherein:

the flow passage is normally closed, is disposed laterally between the frame and the elastomeric member and extends along a substantially linear path between the inlet port and the outlet port; and the means for sequentially deforming the body is coupled to the frame and the elastomeric member and is operably effective for sequentially pulling the elastomeric member away from the frame at a plurality of longitudinally spaced locations, wherein the cavity is created and the cavity and the packet of fluid therein are propagated to the outlet port.

52. A progressive cavity propagation pump as recited in claim 50, wherein:

the frame comprises an outer frame made of a first thermoplastic material, the elastomeric member being overmolded onto the outer frame;

the frame further comprises an inner frame made of a second thermoplastic material, the inner frame engaging the elastomeric member.

53. A progressive cavity propagation pump as recited in claim 52, wherein:

the flow passage is normally closed, is disposed between the elastomeric member and the outer frame and extends along an arcuate path between the inlet port and the outlet port.

54. A progressive cavity propagation pump as recited in claim 53, wherein:

the arcuate path is a circular path.

55. A progressive cavity propagation pump as recited in claim 53, wherein:

the elastomeric member includes an inner hub defining a centrally disposed aperture extending through the elastomeric member;

the elastomeric member further includes a rim and a plurality of circumferentially spaced spokes that extend between the hub and the rim;

the hub, spokes and rim define a plurality of circumferentially spaced cavities having a first shape;

the inner frame includes a plurality of circumferentially spaced engaging members having a second shape that is complimentary with the first shape of the cavities, wherein each of the engaging members is disposed in one of the cavities.

56. A progressive cavity propagation pump as recited in claim 55, wherein:

the engaging members of the inner frame defines a discontinuous cylindrical surface having a first diameter;

the rim includes a discontinuous inner surface having a second diameter;

the first diameter is greater than the second diameter.

57. A progressive cavity propagation pump as recited in claim 50, wherein:

the frame comprises an outer frame made of a first thermoplastic material and an inner frame made of a second thermoplastic material, the outer frame disposed in surrounding relationship with the inner frame;

the elastomeric member overmolded onto the outer frame and the inner frame.

58. A progressive cavity propagation pump as recited in claim 57, wherein:

the flow passage is normally closed, is disposed between the elastomeric member and the outer frame and extends along an arcuate path between the inlet port and the outlet port, the inner frame includes a centrally disposed aperture formed therein;

the means for sequentially deforming the body includes a driven axle disposed within the aperture of the inner frame;

the driven axle orbits in a circular motion that is offset relative to the aperture of the inner frame and the driven axle is in contacting engagement with the inner frame during operation of the pump wherein the elastomeric member is pulled away from the outer frame at a position proximate the inlet port creating the cavity and drawing the packet of fluid from the inlet port into the cavity, and wherein the cavity and the packet of fluid contained therein are propagated along a circular path to the outlet port.

59. A progressive cavity propagation pump as recited in claim 50, wherein the frame comprises:

an outer frame made of a first thermoplastic material, the outer frame having a channel formed therein, the inlet port and the outlet port being in fluid communication with the channel, the channel extending in a circular path between the inlet port and the outlet port;

an inner frame made of a second thermoplastic material, the inner frame including a base member, a tower integral with the base member and extending longitudinally away from the base member and a protruding portion integral with and extending away from the base member, the protruding portion being disposed within the channel of the outer frame; and the elastomeric member overmolded onto the inner and outer frames, wherein the elastomeric member is disposed between the protruding portion of the inner frame and the channel of the outer frame; wherein the flow passage is normally closed, is disposed between the elastomeric member and the channel of the outer frame and extends along a circular path between the inlet port and the outlet port.

60. A progressive cavity propagation pump as recited in claim 59, wherein:
the tower is hollow and includes an inner surface;
the means for sequentially deforming the body includes a driven axle extending into the tower and engaging the inner surface of the tower;
the engagement of the driven axle with the inner surface of the tower during operation of the pump causes the protruding portion to wobble within the channel of the outer frame and causes the elastomeric member disposed between the protruding portion and the channel to pull away from the channel, wherein the cavity is created and the cavity and the packet of fluid contained therein are propagated to the outlet port.

61. A progressive cavity propagation pump as comprising:
a body made at least partially of an elastomeric material and including a pair of confronting portions;
an inlet port and an outlet port, each port being coupled to the body;
a flow passage formed in the body and extending between the inlet port and the outlet port, the pair of confronting portions of the body defining a normally closed portion of the flow passage, the inlet port being fluidicly uncoupled with the outlet port when the pump is in a free state condition;
means for sequentially deforming the body to create a cavity within the normally closed portion of the flow passage, the cavity being in fluid communication with the inlet port, thereby drawing a packet of fluid from the inlet port into the cavity and propagating the cavity and the fluid packet contained therein toward the outlet port;
a first open conduit disposed within the body between the pair of confronting portions of the body, the first open conduit having proximal and distal ends; wherein
the flow passage comprises a first normally closed flow passage having a proximal end disposed proximate the inlet port and a distal end disposed proximate the proximal end of the first open conduit;
the distal end of the first open conduit is disposed proximate the outlet port.

62. A progressive cavity propagation pump as recited in claim 61, further comprising:
a second normally closed flow passage having a proximal end and a distal end, the distal end being disposed proximate the outlet port;
a second open conduit disposed within the body and having a proximal end and a distal end, the proximal end of the second open conduit being disposed proximate the inlet port and the distal end being disposed proximate the proximal end of the second normally closed flow passage.

63. A progressive cavity propagation pump as recited in claim 62, wherein:
the body is adapted to be mounted to a stationary structure, the body including a centrally disposed aperture formed therein;
the means for sequentially deforming the body includes a driven axle disposed within the aperture;
the cavity comprises a first cavity disposed within the first normally closed flow passage;
the driven axle orbits in a circular motion that is offset relative to the aperture during operation of the pump, wherein during a first portion of any revolution of the driven axle the first cavity is created and propagated, with the packet of fluid contained therein to the outlet port, and wherein during a second portion of any revolution of the driven axle a second cavity is created within the second normally closed flow passage, drawing a second packet of fluid into the second cavity, and the second cavity and the second packet of fluid contained therein are propagated, to the outlet port.

64. The progressive cavity propagation pump as recited in claim 62, wherein:
the first and second normally closed flow passages extend along an arcuate path.

65. A progressive cavity propagation pump comprising:
a body made at least partially of an elastomeric material, the body adapted to be mounted to a stationary structure and including a centrally disposed aperture formed therein;
an inlet port and an outlet port, each port being coupled to the body;
a flow passage formed in the body and extending along a circular path between the inlet port and the outlet port, a pair of confronting, normally contacting portions of the body defining a normally closed portion of the flow passage, the inlet port being fluidicly uncoupled with the outlet port when the pump is in a free state condition;
the body being sequentially deformable by a driven axle disposed within the aperture of the body, the driven axle operable to orbit in a circular motion so as to (a) selectively separate the confronting body portions along the normally closed portion of the flow passage whereby to selectively open a cavity at one end of the normally closed portion of the flow passage in fluid communication with the inlet port, and (b) selectively separate the confronting body portions ahead of the cavity and re-close the confronting body portions behind the cavity to thereby propagate the cavity therealong toward a second end of the normally closed portion of the flow passage in fluid communication with the outlet port, whereby to draw a packet of fluid from the inlet port and propagate the packet of fluid contained therein toward the outlet port.

66. A method of pumping a fluid comprising the steps of:
obtaining a pump body having fluid inlet and fluid outlet ports, a flow passage coupled between the fluid inlet and fluid outlet ports, and a pair of confronting, normally contacting portions defining a normally closed portion of the flow passage;
drawing fluid from the inlet port and propagating the fluid toward the outlet port by sequentially deforming the pump body so as to selectively separate the confronting body portions along the normally closed portion of the flow passage whereby to selectively open a cavity at a first end of the normally closed portion of the flow passage in fluid communication with the inlet port, and selectively separate the confronting body portions ahead of the cavity and re-close the confronting body portions behind the cavity to thereby propagate the cavity therealong toward a second end of the normally closed portion of the flow passage in fluid communication with the outlet port; and
sequentially separating an elastomeric portion of the body from a thermoplastic portion of the body to create the cavity and to propagate the cavity and the fluid contained therein toward the outlet port.

67. A method as recited in claim 66, wherein the confronting, normally contacting portions of the body defining the flow passage as normally closed and extending along a substantially linear path, further comprising:
propagating the cavity through the normally closed flow passage along the substantially linear path from the inlet port to the outlet port.

68. A method as recited in claim 66, wherein the confronting, normally contacting portions of the body define the flow passage as normally closed and extend along an arcuate path, further comprising:
propagating the cavity through the normally closed flow passage along the arcuate path from the inlet port to the outlet port.

69. A method as recited in claim 66, further comprising:
fluidicly coupling a source of fluid to the inlet port;
fluidicly coupling the output port to a tubing system coupled to a patient; and pumping the fluid to the patient.

70. A progressive cavity propagation pump comprising:
a body made at least partially of an elastomeric material and including a pair of confronting portions;
an inlet port and an outlet port, each port being coupled to the body;
a flow passage formed in the body and extending between the inlet port and the outlet port, the pair of confronting portions of the body defining a normally closed portion of the flow passage, the inlet port being fluidicly uncoupled with the outlet port when the pump is in a free state condition;
an actuating device coupled to the body, the actuating device operable for sequentially deforming the body to create a cavity within the normally closed portion of the flow passage, the cavity being in fluid communication with the inlet port, thereby drawing a packet of fluid from the inlet port into the cavity and propagating the cavity and the packet of fluid contained therein toward the outlet port;
a first open conduit disposed within the body between the pair of confronting portions of the body, the first open conduit having proximal and distal ends; wherein
the flow passage comprises a first normally closed flow passage having a distal end disposed proximate the outlet port and a proximal end disposed proximate the distal end of the first open conduit;
the proximal end of the first open conduit is disposed proximate the inlet port.

71. A progressive cavity propagation pump as comprising:
a body made at least partially of an elastomeric material and including a pair of confronting portions;
an inlet port and an outlet port, each port being coupled to the body;
a flow passage formed in the body and extending between the inlet port and the outlet port, the pair of confronting portions of the body defining a normally closed portion of the flow passage, the inlet port being fluidicly uncoupled with the outlet port when the pump is in a free state condition;
means for sequentially deforming the body to create a cavity within the normally closed portion of the flow passage, the cavity being in fluid communication with the inlet port, thereby drawing a packet of fluid from the inlet port into the cavity and propagating the cavity and the fluid packet contained therein toward the outlet port;
a first open conduit disposed within the body between the pair of confronting portions of the body, the first open conduit having proximal and distal ends; wherein
the flow passage comprises a first normally closed flow passage having a distal end disposed proximate the outlet port and a proximal end disposed proximate the distal end of the first open conduit;
the proximal end of the first open conduit is disposed proximate the inlet port.

* * * * *